(12) United States Patent
Spellberg et al.

(10) Patent No.: US 11,306,137 B2
(45) Date of Patent: Apr. 19, 2022

(54) **ANTIBODY BINDING AGENTS THAT BIND *ACINETOBACTER* AND USES THEREOF**

(71) Applicant: LOS ANGELES BIOMEDICAL RESEARCH INSTITUTE AT HARBOR-UCLA MEDICAL CENTER, Torrance, CA (US)

(72) Inventors: Brad Spellberg, Torrance, CA (US); Kevin Bruhn, Torrance, CA (US); Travis Nielsen, Torrance, CA (US)

(73) Assignee: Los Angeles BioMedical Research Institute at Harbor-UCLA Medical Center, Torrance, CA (US)

( * ) Notice: Subject to any disclaimer, the term of this patent is extended or adjusted under 35 U.S.C. 154(b) by 519 days.

(21) Appl. No.: 15/743,775

(22) PCT Filed: Jul. 13, 2016

(86) PCT No.: PCT/US2016/042124
§ 371 (c)(1),
(2) Date: Jan. 11, 2018

(87) PCT Pub. No.: WO2017/011572
PCT Pub. Date: Jan. 19, 2017

(65) Prior Publication Data
US 2018/0215811 A1    Aug. 2, 2018

Related U.S. Application Data

(60) Provisional application No. 62/192,029, filed on Jul. 13, 2015.

(51) Int. Cl.
| | | |
|---|---|---|
| C07K 16/12 | (2006.01) | |
| A61P 31/04 | (2006.01) | |
| G01N 33/569 | (2006.01) | |
| A61K 39/00 | (2006.01) | |

(52) U.S. Cl.
CPC .......... *C07K 16/1217* (2013.01); *A61P 31/04* (2018.01); *G01N 33/56911* (2013.01); *A61K 2039/505* (2013.01); *C07K 2317/21* (2013.01); *C07K 2317/24* (2013.01); *C07K 2317/54* (2013.01); *C07K 2317/55* (2013.01); *C07K 2317/56* (2013.01); *C07K 2317/565* (2013.01); *C07K 2317/567* (2013.01); *C07K 2317/622* (2013.01); *C07K 2317/76* (2013.01); *G01N 2333/22* (2013.01)

(58) Field of Classification Search
None
See application file for complete search history.

(56) References Cited

FOREIGN PATENT DOCUMENTS

| WO | 2012158529 A2 | 11/2012 |
|---|---|---|
| WO | 2013040478 A2 | 3/2013 |
| WO | 2013079207 A1 | 6/2013 |
| WO | 2016029079 A2 | 2/2016 |
| WO | 2016075305 A2 | 5/2016 |

OTHER PUBLICATIONS

Schroeder et al, J. Allergy Clin. Immunol. 125:S41-52, 2010.*
Harlow et al Antibodies:A Laboratory Manual, Chapter 14, pp. 553-615, 1989.*
Liou et al., American Journal of Infection Control, 45:723-7, 2017.*
Dorland's Medical Dictionary for Healthcare Consumers.*
Stedmans's Online Medical Dictionary.*
The American Heritage Dictionary.*
Colman (Res Immunology 145:33-36, 1994).*
Kussie et al (Journal of Immunology 152:146-152, 1994).*
Chen e tal (The EMBO Journal, 14(12):2784-2794, 1995).*
Written Opinion of the International Searching Authority PCT/US2016/042124 dated Sep. 28, 2016.
International Search Report PCT/US2016/042124 dated Sep. 28, 2016.
S. Singh et al., "A Monoclonal Antibody against Hcp, the Type Six Secretion System needle, protects mice from Acinetobacter baumannii infection", Presentation Abstract No. 1-314a, Proceedings of the 54th Interscience Conference on Antimicrobial Agents and Chemotherapy (ICAAC 2014), Washington DC 2014; [online] [retrieved on Sep. 21, 2016] http://www.abstractsonline.com/Plan/ViewAbstract.aspx?sKey=cc719b39-91b9-42ff-98ce-142d2b39c702&cKey=e6869521-e089-427d-bff0-0a9c8d434508&mKey=5d6b1802.
Akeel Baag et al., "Development and Characterization of Monoclonal Antibodies for Rapid Detection of Acinetobacter baumannii", Monoclonal antibodies in immunodiagnosis and immunotherapy, Aug. 29, 2014, 33/4"291-298 [online] [retrieved on Sep. 21, 2016] http://online.liebertpub.com/doi/full/10.1089/mab.2013.0073<DOI:10.1089/mab.2013.0073>.
Thomas A. Russo et al., "The K1 capsular polysaccharide from Acinetobacter baumannii is a potential therapeutic target via passive immunization", Infection and immunity, 2013, 81.3: 915-922 [online] [retrieved on Sep. 21, 2016] http://iai.asm.org/content/81/3/915.short><doi: 10.1128/IAI.01184-12>.
European Patent Office, Extended European Search Report for EP Application No. 16825122.1, dated Feb. 14, 2019, pp. 1-13.
Nielsen et al., Monoclonal Antibody Protects Against Acinetobacter baumannii Infection by Enhancing Bacterial Clearance and Evading Sepsis, The Journal of Infectious Diseases, Jul. 5, 2017, pp. 489-501, vol. 216, No. 4.
Spellberg, Brad J., Humanized Monoclonal Antibodies to Treat Acinetobacter Infections, Grantome, Jul. 1, 2013, pp. 1-5, retrieved from the Internet: URL:http://grantome.com/grant/NIH/R4I-AI106375-01AI, on Jan. 31, 2019.
Baig et al., Development and Characterization of Monoclonal Antibodies for Rapid Detection of Acinetobacter baumannii, Monoclonal antibodies in immunodiagnosis and immunotherapy, retrieved from the Internet: URL: https://www.liebertpub.com/doi/full/10.1089/mab.2013.0073, on Aug. 29, 2014.

* cited by examiner

*Primary Examiner* — Patricia Duffy
(74) *Attorney, Agent, or Firm* — Pillsbury Winthrop Shaw Pittman LLP

(57) ABSTRACT

Presented herein, in certain embodiments, are compositions comprising antibody binding agents that specifically bind to *A. baumannii* and inhibit and/or block *A. baumannii* infection, and uses thereof.

18 Claims, 16 Drawing Sheets

Specification includes a Sequence Listing.

DAPI + Isotype Control-AF488    DAPI + C8 MAb-AF488

40,000x

FIG. 9C
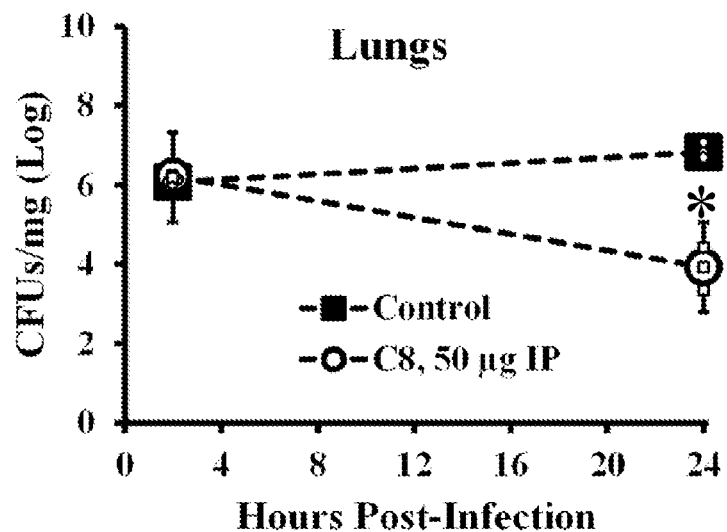
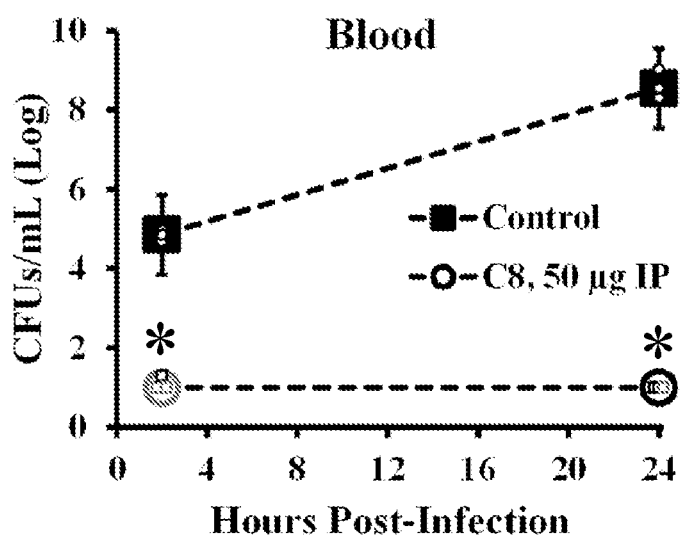

ANTIBODY BINDING AGENTS THAT BIND *ACINETOBACTOR* AND USES THEREOF

GOVERNMENT SUPPORT

This invention was made with government support under contract/grant number R41 AI106375, R01 AI1081719, R21 AI101750, R56 AI104751 and R41 AI106375 to BS and R01 AI072219 to RAB awarded by NIH/NIAD and in part by funds and/or facilities provided by the Cleveland Department of Veterans Affairs, the Veterans Affairs Merit Review Program [Award 1I01BX001974]; and the Geriatric Research Education and Clinical Center [VISN 10 to R.A.B.]. The government has certain rights in the invention. Electron microscopy was performed at the USC Norris Cell and Tissue Imaging Core, supported by NCI grant 5 P30 CA014089.

RELATED APPLICATIONS

This application is a U.S. National Stage of International Patent Application No. PCT/US2016/042124, filed Jul. 13, 2016, entitled ANTIBODY BINDING AGENTS THAT BIND *ACINETOBACTER* AND USES THEREOF, and naming inventors Brad Spellberg, Kevin Bruhn and Travis Neilsen, which published as International Patent Publication No. WO/2017/011572 on Jan. 19, 2017, and claims the benefit of U.S. Provisional Patent Application No. 62/192,029 filed on Jul. 13, 2015, entitled ANTIBODY BINDING AGENTS THAT BIND *ACINETOBACTER* AND USES THEREOF, naming as inventors Brad Spellberg, Kevin Bruhn and Travis Neilsen. The entire content of the foregoing applications are incorporated herein by reference, including all text, tables and drawings.

SEQUENCE LISTING

The instant application contains a Sequence Listing which has been submitted electronically in ASCII format and is hereby incorporated by reference in its entirety. Said ASCII copy, created on May 20, 2021, is named 022098-0456416-Sequence_Listing.txt and is 17,516 bytes in size.

FIELD OF THE INVENTION

Embodiments of the invention relate to compositions comprising antibody binding agents that specifically bind to *A. baumannii* and inhibit and/or block *A. baumannii* infection, and uses thereof.

INTRODUCTION

The genus *Acinetobacter* is divided into at least 21 species based on 16S ribosomal sequence analysis. *Acinetobacter* are gram-negative, oxidase-negative, non-motile, nitrate-negative, nonfermentative rods. The glucose-oxidizing, non-hemolytic *Acinetobacter baumannii* (*A. baumannii*, often including spelling variants *A. baumanii* and *A. baumanni*), formerly known as *Acinetobacter calcoaceticus* var. *anitratus*, is the most frequently isolated species in this genus.

*A. baumannii* is commonly found in the environment as well as in hospitals where it is recognized as a nosocomial pathogen. The ability of *A. baumannii* to survive on dry surfaces for long periods of time has contributed to outbreaks in hospitals. Such outbreaks are often traced to the presence of *A. baumannii* on various hospital equipment such as reusable pressure transducers, room humidifiers, mattresses, pillows, intravascular access devices, and components of ventilation and respiratory therapy equipment. *A. baumannii* is often associated with bacteremia, septicemia, pneumonia, meningitis, and infections of burns, the urinary tract and surgical wounds. *A. baumannii* is thought to be responsible for 1-2% of all nosocomial infections. It is estimated that the number of *A. baumannii* infections per year in the United States is about 45,900 and the number of infections per year globally (in developed nations) is about 1,000,000. The mortality rate of nosocomial infections by *A. baumannii* can be quite high. For example, the mortality rate of meningitis caused by *A. baumannii* is estimated at about 20% to 27%, and bacteremia mortality ranges from about 19% to 44%. The mortality of bacteremia caused by carbapenem-resistant *Acinetobacter* has been described to exceed 50%.

Resistance to antibiotics by the genus *Acinetobacter* has increased over time, with *A. baumannii* usually being the most resistant. *A. baumannii* is becoming resistant to many compounds that it was previously susceptible to, such as fluoroquinolones, aminoglycosides, ceftazidime, ticarcillin, and imipenem. In one study, at least 82% of the *A. baumannii* isolates were resistant to piperacillin, gentamicin, amikacin, netrilaicin, ceftazidime, cefotaxime, and norfloxacin. Resistance to ciprofloxacin in *A. baumannii* isolated from ICU patients increased from 4% in 1986 to 34% in 1993. *Acinetobacter* clinical isolates may be resistant to any of the therapeutically relevant antibiotics and resistance is influenced by selection pressure of the preferred antibiotic.

National surveillance data from 2009-2012 demonstrated that an astonishing 50% of *A. baumannii* isolates from US intensive care units were extremely drug-resistant (XDR) (i.e., resistant to carbapenems and all other antibiotics except colistin or tigecycline). One of the antibiotic-resistant strains of *A. baumannii* of considerable concern is carbapenem-resistant *Acinetobacter baumannii* (CRAB). Up to half of ICU *A. baumannii* isolates in the US are carbapenem-resistant. It is estimated that 22,950 cases of CRAB infection occur annually in the United States and 75,000 globally (in developed nations). Based on the number of cases and the cost per case, carbapenem resistance costs health-care systems an annual excess of 389 million and 4,590 deaths in the United States, and an annual excess of 742 million and 15,000 deaths globally.

Presented herein are monoclonal antibodies that can bind to *A. baumannii* and method of using the same for the treatment, prevention and diagnosis of *A. baumannii* infection.

BRIEF DESCRIPTION OF THE FIGURES

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 5. demonstrates surface binding of *A. baumannii* by purified C8 MAb.

FIG. 6. C8 MAb opsonizes bacteria for uptake by macrophages.

FIG. 7. The C8 MAb markedly improved survival with otherwise lethal bloodstream infection caused by the XDR strain, *A. baumannii* HUMC1.

FIG. 8. C8 MAb lowered bacterial density and ameliorated the sepsis response to iv *A. baumannii* infection. Mice (n=3 per group) were infected i.v. with 1.5×10$^7$ *A. baumannii* HUMC1 and treated i.v. with 5 µg of C8 MAb or IgG isotype control in 250 µL PBS.

FIG. 9. The C8 MAb also markedly improved survival during aspiration pneumonia. FIG. 9C shows bacterial density of *A. baumannii* in the lungs and blood of infected mice with, or without C8 monoclonal treatment. Three mice per group were euthanized at 2 hr and 24 hr post-infection, and lung homogenates and blood were diluted and plated on agar to determine bacterial burdens.

SUMMARY OF THE INVENTION

Figure 1:
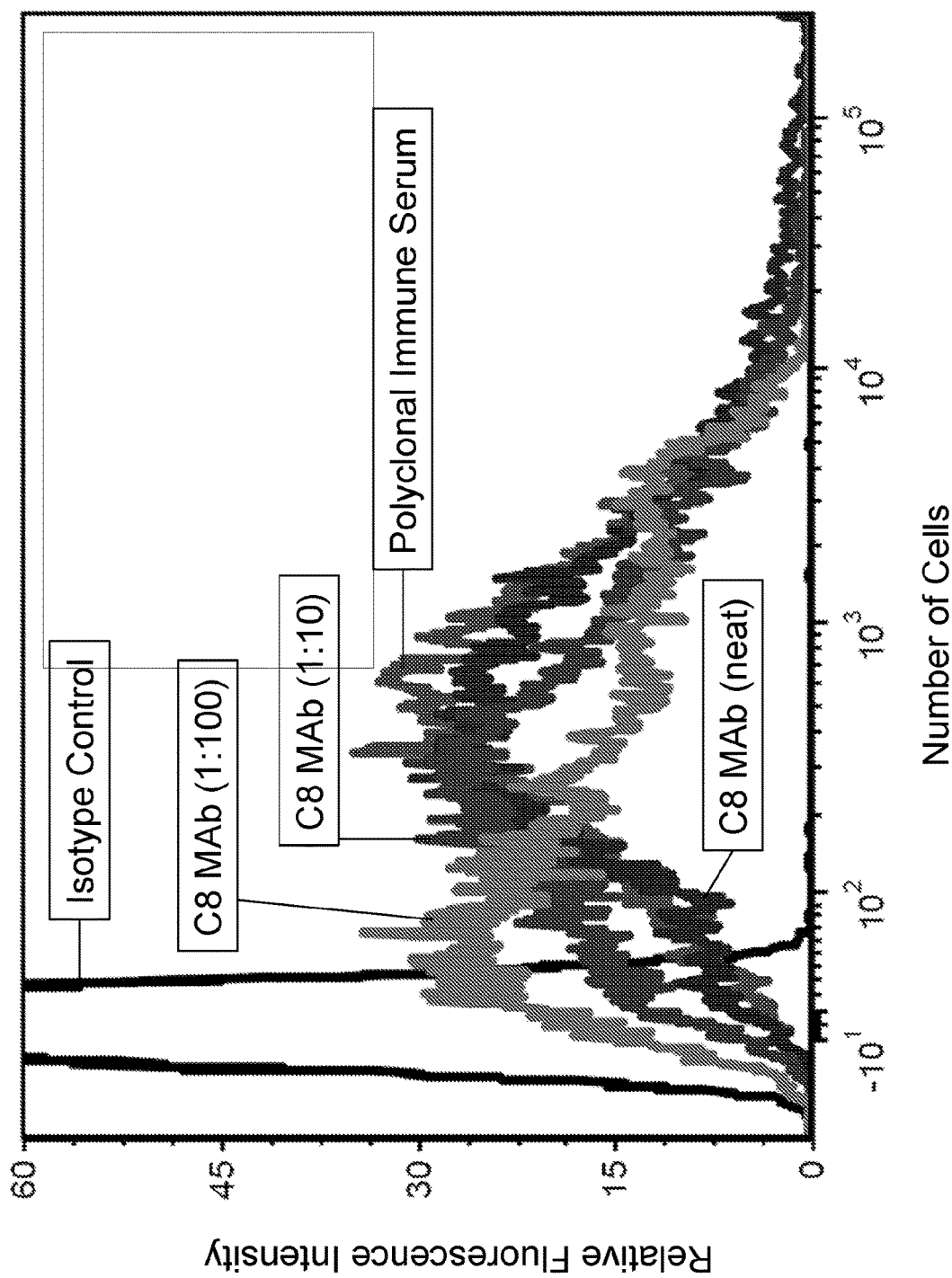
FIG. 1 shows a flow cytometry histogram of *A. baumannii* cells (HUMC1 strain) stained with C8 monoclonal antibody (C8 mAb) at the indicated dilutions, polyclonal immune sera or an isotype control antibody (Isotype Control) followed by anti-mouse IgG-APC (secondary antibody). Fluorescence intensity is indicated on the y-axis. Results shown are representative of 5 other strains: HUMC6, C14, ATCC 17978, AB0071, UH7007 (Table 7). Similar results were observed with virulent strain LAC-4.

In some aspects, presented herein are compositions comprising antibody binding agents that specifically bind to *A. baumannii*. In some aspects, presented herein are compositions comprising monoclonal antibodies, and in some aspects humanized monoclonal antibodies, or binding fragments thereof, that bind specifically to *A. baumannii*. In certain aspects, monoclonal antibodies, or binding fragments thereof, that bind *A. baumannii* can be used to treat or prevent an *A. baumannii* infection in a mammal. In some embodiments, provided herein is a pharmaceutical composition comprising an antibody binding agent that specifically binds to *A. baumannii* where the antibody binding agent comprises one to three CDRs of a light chain variable region selected from Table 1, 2 and 3, or one to three CDRs with at least 75% identity to a CDR selected from Table 1, 2 and 3. In some embodiments, provided herein is a pharmaceutical composition comprising an antibody binding agent that specifically binds to *A. baumannii* where the antibody binding agent comprises one to three CDRs of a heavy chain variable region selected from Table 4, 5 and 6, or one to three CDRs with at least 75% identity to a CDR selected from Table 4, 5 and 6. In certain embodiments, provided herein is a pharmaceutical composition comprising an antibody binding agent that specifically binds to *A. baumannii* wherein the antibody binding agent comprises three CDRs of a light chain variable domain of SEQ ID NO:2 or SEQ ID NO:28. In certain embodiments, provided herein is a pharmaceutical composition comprising an antibody binding agent that specifically binds to *A. baumannii* wherein the antibody binding agent comprises three CDRs of a heavy chain variable domain of SEQ ID NO:3 or SEQ ID NO:29. In some embodiments, provided herein is a pharmaceutical composition comprising an antibody binding agent that specifically binds to *A. baumannii* wherein the antibody binding agent comprises three CDRs of a light chain variable domain of SEQ ID NO:2 or SEQ ID NO:28 and three CDRs of a heavy chain variable domain of SEQ ID NO:3 or SEQ ID NO:29. In certain embodiments an antibody binding agent is a monoclonal antibody binding agent or a humanized monoclonal antibody binding agent. An antibody binding agent can be an antibody or binding fragment thereof.

In some embodiments, provided herein is a humanized antibody binding agent comprising a light chain variable domain comprising at least two CDRs chosen from a CDR-L1 of Table 1, a CDR-L2 of Table 2 and a CDR-L3 of Table 3, wherein the humanized antibody binding agent specifically binds to *A. baumannii*. In some embodiments, provided herein is a humanized antibody binding agent comprising a heavy chain variable domain comprising at least two CDRs chosen from a CDR-H1 of Table 4, a CDR-H2 of Table 5 and a CDR-H3 of Table 6, wherein the humanized antibody binding agent specifically binds to *A. baumannii*. In some embodiments, provided herein is a humanized antibody binding agent comprising a light chain variable domain comprising at least two CDRs chosen from a CDR-L1 of Table 1, a CDR-L2 of Table 2, a CDR-L3 of Table 3, and a heavy chain variable domain comprising at least two CDRs chosen from a CDR-H1 of Table 4, a CDR-H2 of Table 5 and a CDR-H3 of Table 6; wherein the humanized antibody binding agent specifically binds to *A. baumannii*. In certain embodiments provided herein is a humanized antibody binding agent comprising a light chain variable domain comprising CDR-L1 of SEQ ID NO:4, CDR-L2 of SEQ ID NO:8 and CDR-L3 of SEQ ID NO:12 and a heavy chain variable domain comprising CDR-H1 of SEQ ID NO:16, CDR-H2 of SEQ ID NO:20 and CDR-H3 of SEQ ID NO:24; wherein the humanized antibody binding agent specifically binds to *A. baumannii*. In certain embodiments provided herein is a humanized antibody binding agent comprising a light chain variable domain comprising CDR-L1 of SEQ ID NO:30, CDR-L2 of SEQ ID NO:35 and CDR-L3 of SEQ ID NO:38 and a heavy chain variable domain comprising CDR-H1 of SEQ ID NO:44, CDR-H2 of SEQ ID NO:46 and CDR-H3 of SEQ ID NO:50; wherein the humanized antibody binding agent specifically binds to *A. baumannii*.

In some embodiments, provided herein is a method of preventing or treating an *A. baumannii* infection comprising a) identifying a subject having, or at risk of having, an *A. baumannii* infection and b) administering to the subject a therapeutically effective amount of a pharmaceutical composition comprises an antibody binding agent that specifically binds to *A. baumannii*, wherein the antibody binding agent comprises one to three CDRs of a light chain variable region selected from Table 1, 2 and 3, or one to three CDRs with at least 75% identity to a CDR selected from Table 1, 2 and 3. In some embodiments, provided herein is a method of preventing or treating an *A. baumannii* infection comprising a) identifying a subject having, or at risk of having, an *A. baumannii* infection and b) administering to the subject a therapeutically effective amount of a pharmaceutical composition comprises an antibody binding agent that specifically binds to *A. baumannii*, wherein the antibody binding agent comprises one to three CDRs of a heavy chain variable region selected from Table 4, 5 and 6, or one to three CDRs with at least 75% identity to a CDR selected from Table 4, 5 and 6.

In some embodiments, provided herein is a method of detecting the presence of absence of *A. baumannii* in a sample obtained from a subject comprising contacting the sample with an antibody binding agent that specifically binds to *A. baumannii*, wherein the antibody binding agent comprises one to three CDRs of a light chain variable region selected from Table 1, 2 and 3, or one to three CDRs with at least 75% identity to a CDR selected from Table 1, 2 and 3, and detecting the presence or absence of a bound complex comprising the antibody binding agent and a fungus of the species *A. baumannii*, or a portion thereof. In some embodiments, provided herein is a method of detecting the presence of absence of *A. baumannii* in a sample obtained from a subject comprising contacting the sample with an antibody binding agent that specifically binds to *A. baumannii*, wherein the antibody binding agent comprises one to three CDRs of a heavy chain variable region selected from Table 4, 5 and 6, or one to three CDRs with at least 75% identity to a CDR selected from Table 4, 5 and 6, and detecting the presence or absence of a bound complex comprising the antibody binding agent and a fungus of the species *A. baumannii*, or a portion thereof. In certain embodiments, the presence of a bound complex indicates the presence of *A. baumannii* in the sample.

Also presented herein are kits comprising an antibody binding agent described herein.

DETAILED DESCRIPTION

Presented herein, in some embodiments, are antibodies and antibody binding agents that bind the cell surface of *A. baumannii*. Presented herein, in some embodiments, are pharmaceutical compositions comprising antibodies and/or antibody binding agents that bind the cell surface of *A. baumannii*. In certain embodiments antibodies and antibody binding agents that bind the cell surface of *A. baumannii* can prevent, inhibit and/or block an *A. baumannii* infection, and/or the progression thereof, in a subject. In some embodiments, the antibodies presented herein can be used for the treatment, prevention and diagnosis of *A. baumannii* infection. In some embodiments, the antibodies presented herein can be used for treating or preventing an infection of a subject by an antibiotic resistant strain or isolate of *A. baumannii*.

Subjects

The term "subject" refers to animals, typically mammalian animals. Any suitable mammal can be treated by a method or composition described herein. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In some embodiments a mammal is a human. A mammal can be any age or at any stage of development (e.g., an adult, teen, child, infant, or a mammal in utero). A mammal can be male or female. A mammal can be a pregnant female. In certain embodiments a mammal can be an animal disease model, for example, animal models used for the study of bacteria infection.

In some embodiments a subject or mammal is "at risk" of acquiring an *A. baumannii* infection. A mammal that is at risk may have increased risk factors for acquiring a bacterial infection, non-limiting examples of which include immuno-compromised individuals or immune deficient subjects (e.g., bone marrow transplant recipients, irradiated individuals, subjects having certain types of cancers, particularly those of the bone marrow and blood cells (e.g., leukemia, lymphoma, multiple myeloma), subjects with certain types of chronic infections (e.g., HIV, e.g., AIDS), subjects treated with immunosuppressive agents, subjects suffering from malnutrition and aging, subjects taking certain medications (e.g. disease-modifying anti-rheumatic drugs, immunosuppressive drugs, glucocorticoids), subjects undergoing chemotherapy, the like or combinations thereof). In some embodiments a subject at risk is, will be, or has been in a location or environment suspected of containing *A. baumannii*. For example, a subject at risk can be a medical professional that is providing care to another who is suspected of being infected with, or known to be infected with *A. baumannii*. In certain embodiments, a subject at risk is any subject that has been exposed to *A. baumannii*. In certain embodiments, a subject at risk is any patient who is, will be, or has been in a hospital or medical care facility suspected of containing *A. baumannii*. In certain embodiments, a subject at risk is any patient who is, will be, or has recently been (e.g., within 1 day to 1 year, or within 3 months to 6 months), in an intensive care unit, long term acute care hospital, rehabilitation hospital or facility, or skilled nursing facility. In certain embodiments, a subject at risk is on mechanical ventilation. In certain embodiments, a subject at risk is any patient who has, will have, or has had a central venous catheter, including a peripherally inserted central catheter. In certain embodiments, a subject at risk is on mechanical ventilation. In certain embodiments, a subject at risk is any patient who has undergone an invasive medical treatment or procedure.

In some embodiments a subject in need of a treatment or composition described herein is a subject at risk of an *A. baumannii* infection and/or a subject that has an *A. baumannii* infection. In some embodiments a subject in need of a treatment or composition described herein is infected with, or is suspected of being infected with *A. baumannii*. In certain embodiments an antibody binding agent (e.g., an antibody or the like) or composition described herein is used to treat or prevent an *A. baumannii* infection in a subject or a subject at risk of acquiring an *A. baumannii* infection.

In some embodiments a subject in need of a treatment or composition described herein is a donor. In some embodiments a donor is healthy subject or a moderately healthy subject. In some embodiments a donor is free of an *A. baumannii* infection. A donor may or may not be at risk of acquiring an *A. baumannii* infection. In some embodiments a donor is an organ donor. In some embodiments a donor is preselected or predetermined to donate an organ, blood, bone marrow, serum, or the like to a subject who is at risk, or will become at risk of acquiring an *A. baumannii* infection. Thus a donor is sometimes a subject in need of treatment or a composition described herein.

Samples

Provided herein are methods and compositions for analyzing samples. In some embodiments, the presence or absence of *A. baumannii* in a subject is determined by analyzing a sample obtained from the subject. In some embodiments, the presence or absence of an *A. baumannii* infection in a subject is determined by analyzing a sample obtained from a subject. In some embodiments, a sample is analyzed for the presence or absence of *A. baumannii*. In certain embodiments, an amount of *A. baumannii* in a sample is determined.

A sample can be any specimen that is isolated or obtained from a subject or part thereof (e.g., a human subject). A test sample is often obtained from a subject (e.g., a subject suspected of having an *A. baumannii* infection, e.g., a subject at risk of having an *A. baumannii* infection). In some embodiments, a sample (e.g., a sample obtained from a subject) is suspected of comprising *A. baumannii*). Non-limiting examples of specimens include fluid or tissue from a subject, including, without limitation, blood or a blood product (e.g., serum, plasma, or the like), umbilical cord blood, chorionic villi, amniotic fluid, cerebrospinal fluid, spinal fluid, lavage fluid (e.g., broncho alveolar, gastric, peritoneal, ductal, ear, arthroscopic), a biopsy sample, urine, feces, sputum, saliva, nasal mucous, prostate fluid, lavage, semen, lymphatic fluid, bile, tears, sweat, breast milk, breast fluid, any secretion or discharge (e.g., from a wound, surgical lesion, abscess cysts, or the like), the like or combinations thereof.

Collection of a sample is often performed in accordance with a standard protocol that medical practitioners, hospitals and/or clinics generally follow. An appropriate amount of a sample can be between about 1 µl and 200 ml, between about 100 µl and 50 ml or between about 0.5 ml and 50 ml. A sample can be collected and may be stored according to standard procedure prior to further preparation. Blood samples may be collected, stored or transported in a manner that minimizes degradation or the quality of proteins and/or nucleic acids present in the sample.

In certain embodiments a sample is prepared and/or processed prior to, or during analysis of a sample. For example, a sample may be centrifuged and/or washed to isolate or concentrate micro-organisms (e.g., *A. baumannii*) that may be present in a sample. In some embodiments, a sample is subjected to a lysis procedure. In certain embodiments, certain materials of a sample (e.g., whole bacteria, membranes, mitochondria, membrane-bound proteins) are isolated or concentrated using a suitable method, non-limiting examples of which include immunoprecipitation, column chromatography (e.g., affinity chromatography), centrifugation, lysis, extraction, precipitation, heat denaturation, detergent treatment, filtering, sonication, the like or combinations thereof. In some embodiments, micro-organisms of a sample, or portions thereof, are resuspended in a buffer suitable for analysis.

*A. baumannii*

In some embodiments *A. baumannii* refers to any pathogenic or potentially pathogenic strain or isolate of *A. baumannii* capable of causing an infection in a subject. For diagnostic embodiments, *A. baumannii* may refer to any pathogenic, potentially pathogenic or non-pathogenic strain or isolate of *A. baumannii*. In some embodiments *A. baumannii* refers to any strain or isolate of *A. baumannii* that displays resistance to one or more drugs (e.g., anti-bacteria drugs) or anti-bacteria treatments. In certain embodiments *A. baumannii* is a strain or isolate that is resistant to multiple drugs (e.g., a multi-drug resistant strain). Non-limiting examples of strains or isolates of *A. baumannii* include HUMC1, LAC-4, C14, and any drug resistant or multi-drug resistant strain or isolate of *A. baumannii* (e.g., any strain or isolate of *A. baumannii* that is resistant to one or more anti-bacterial medications). In some embodiments *A. baumannii* is a carbapenem-resistant *A. baumannii*. In some embodiments *A. baumannii* is a strain or isolate of *A.* baumannii that does not display resistance to a drug (e.g., an anti-bacteria medication) or anti-bacteria treatment.

Any suitable *A. baumannii* infection can be prevented or treated by a method or composition herein. *A. baumannii* infections can be systemic and/or local. Non-limiting examples of local *A. baumannii* infections include infections of the skin (epidermis, dermis, hypodermis, subcutaneous tissue), epithelial membranes, sinus membranes, ears, eyes, nose, throat, mouth, scalp, feet, nails, vagina, endometrium, urinary tract (e.g., bladder, urethra), the like, portions thereof or combinations thereof. Non-limiting examples systemic *A. baumannii* infections include infection of one or more tissues or organs, non-limiting examples of which include liver, kidney, heart, muscle, lung, stomach, large intestine, small intestine, testis, ovaries, brain, nervous tissue, blood, lymph, lymph nodes, salivary glands, the like or combinations thereof.

Antibody Binding Agents

An antibody binding agent sometimes comprises or consists of a suitable antibody, an antibody fragment and/or an antigen binding portion thereof (e.g., a binding fragment). In some embodiments an antibody binding agent is an antibody or an antigen binding portion thereof. An antibody can refer to a natural antibody, monoclonal antibody, recombinant antibody, a chimeric antibody, an antibody binding fragment (e.g., an antigen binding portion of an antibody), a CDR-grafted antibody, a humanized antibody, a human antibody, or portions thereof. In certain embodiments, an antibody binding agent is not polyclonal and does not refer to polyclonal antibodies. In some embodiments, an antibody is derived, obtained, isolated, or purified from a suitable species. In some embodiments an antibody is derived, obtained, isolated, or purified from a bird (e.g., a chicken, or chicken egg). In some embodiments an antibody is derived, obtained, isolated, or purified from a suitable mammal. In certain embodiments a suitable mammal is a genetically altered mammal (e.g., a trans chromosomal or transgenic mammal) engineered to produce antibodies comprising human heavy chains and/or human light chains or portions thereof. In some embodiments, an antibody is derived, obtained, isolated, or purified from a rabbit, goat, horse, cow, rat, mouse, fish, bird, or llama, for example.

In some embodiments, a monoclonal antibody or monoclonal binding agent is a substantially homogeneous population of antibody binding agents, or binding fragments thereof, where each individual binding agent in the population are substantially identical and/or bind the same epitope, with the except of possible variants that may arise during production of a monoclonal binding agent. In some embodiments, such variants generally are absent or may be present in minor amounts. In contrast to polyclonal antibody preparations which typically include different antibodies directed against different determinants (epitopes), each monoclonal antibody of a population often binds a single determinant on an antigen. Monoclonal antibodies are often uncontaminated by other immunoglobulins. The modifier "monoclonal" is not to be construed as requiring production of the antibody by any particular method. For example, in certain embodiments, a monoclonal antibody is made by the hybridoma method (e.g., as described by Kohler et al, Nature, 256:495 (1975)), or a variation thereof. In some embodiments a monoclonal binding agent is made by recombinant DNA method. For example, a monoclonal binding agent can be made by screening a recombinant library using a suitable expression system (e.g., a phage display expression system). In some embodiments, a monoclonal binding agent is isolated from a phage library of binding agents, for example by using a technique described in Clackson et al, Nature, 352:624-628 (1991) and/or Marks et al, J. Mol Biol, 222: 581-597 (1991), or a variation thereof.

In mammals an antibody can have two types of immunoglobulin light chains, lambda (λ) and kappa (κ), which are often defined by the C-terminal constant regions of the light chain polypeptides (light chain constant regions). An antibody binding agent can have any suitable light chain constant region, or portion thereof. In some embodiments an antibody binding agent comprises a lambda light chain constant region or a portion thereof. In some embodiments an antibody binding agent comprises a kappa light chain constant region or a portion thereof. In some embodiments an antibody binding agent does not have a light chain constant region. In mammals, an antibody can have five types/classes of Ig heavy chains denoted as IgA, IgD, IgE, IgG, and IgM, which are determined by the presence of distinct heavy chain constant regions, or portion thereof (e.g., CH1, CL, CH2, CH3 domains). An antibody binding agent can have any suitable heavy chain constant region, or portion thereof. In some embodiments an antibody binding agent comprises a heavy chain constant region of an $IgG_1$, $IgG_2$, $IgG_3$ or $IgG_4$, or a portion thereof. In some embodiments an antibody binding agent comprises a heavy chain constant region of an IgM, IgD, IgA, or IgE isotype or a portion thereof. In some embodiments an antibody binding agent does not have a heavy chain constant region. Methods of modifying (e.g., adding, removing, modifying) heavy chain and light chain constant regions to modify the class and/or isotype of an antibody binding agent are well known in the art.

In certain embodiments, an antibody heavy chain, heavy chain variable region or antigen binding portion thereof, binds to an antigen in the absence of an antibody light chain, light chain variable region or antigen binding portion thereof. In certain embodiments, an antibody light chain, light chain variable region or antigen binding portion thereof, binds to an antigen in the absence of an antibody heavy chain, heavy chain variable region or antigen binding portion thereof. In certain embodiments, an antibody binding agent does not comprise an antibody light chain, or portion thereof. In certain embodiments, an antibody binding agent does not comprise an antibody heavy chain, or portion thereof. In certain embodiments, an antigen binding portion of an antibody variable region (e.g., a heavy chain or light chain variable region) specifically binds to an antigen in the absence of the other variable region.

In some embodiments an antibody binding agent comprises or consists of one or more suitable antigen binding portions of an antibody. In some embodiments an antibody binding agent comprises or consists of one or more variable regions of an antibody, or a portion thereof. In some embodiments an antibody binding agent comprises a Fab, Fab', F(ab')2, Fv fragment, single-chain Fv (scFv), diabody (Dab), synbody, the like and/or a combination or portion thereof. In some embodiments an antibody binding agent is a Fab, Fab', F(ab')2, Fv fragment, single-chain Fv (scFv), diabody (Dab), synbody, the like and/or a combination, or portion thereof (see, e.g., U.S. Pat. Nos. 6,099,842 and 5,990,296). In some embodiments, an antibody binding agent comprises a single-chain polypeptide comprising one or more antigen binding portions of an antibody. For example, a single-chain antibody binding agent can be constructed by joining a heavy chain variable region, or antigen binding portion thereof, with a light chain variable region, or antigen binding portion thereof, with a polypeptide linker (e.g., the linker is often attached at the C-terminus or N-terminus of each chain)

using recombinant molecular biology processes. Such single chain antibody binding agents often exhibit specificities and affinities for an antigen similar to a parent two-chain monoclonal antibody. Antibody binding agents often comprise engineered regions such as CDR-grafted or humanized portions. In certain embodiments an antibody binding agent is an intact two-chain immunoglobulin, and in other embodiments an antibody binding agent is a Fab monomer or a Fab dimer. Methods for generating antibodies, recombinant antibodies and/or antigen binding portions thereof are known. The genes, or portions thereof, that encode a polypeptide of an antibody binding agent may be cloned, subcloned, rearranged or modified for recombinant expression by a suitable cloning procedure and subsequently expressed using a suitable expression system by a method known to those skilled in the art (e.g., see Maniatis et al., Molecular Cloning: A Laboratory Manual, Cold Spring Harbor Laboratory, 1982; Antibody Engineering: Methods and Protocols, Vol. 248 of Methods in molecular biology, edited by Benny K. C. Lo, Springer Science & Business Media, 2004; Antibody Engineering, Vol. 1, Roland E. Kontermann, Stefan Dübel, Edition 2, Publisher Springer Science & Business Media, 2010; Antibody Phage Display: Methods and Protocols, Biomed Protocols, Vol. 178 of Methods in molecular biology, Editors Philippa M. O'Brien, Robert Aitken, Springer Science & Business Media, 2004; which are hereby incorporated by reference in their entirety).

In mammals, the heavy chain variable region and light chain variable region of an antibody binding agent each contribute three CDRs (complementary determining regions, CDR1, CDR2 and CDR3) that are separated and/or flanked by framework regions (e.g., FR1, FR2, FR3 and FR4). In certain embodiments, definitive delineation of a CDR and identification of residues comprising the binding site of an antibody is accomplished by solving the structure of the antibody and/or solving the structure of the antibody-ligand complex. In certain embodiments, this can be accomplished by any of a variety of techniques known to those skilled in the art, such as X-ray crystallography and/or computer modeling. In certain embodiments, various methods of analysis can be employed to identify or approximate the CDR regions or an antibody. For example, the amino sequence and/or location of CDRs of an antibody can be identified using a suitable method, non-limiting examples of which include the Kabat system (e.g., see Kabat, E. A., et al., 1991; Sequences of Proteins of Immunological Interest, Fifth Edition, NIH Publication No. 91-3242, as well as Johnson, G. and Wu, T. T. 2000, Nucleic Acids Research), and/or the Chothia Numbering Scheme (e.g., Chothia & Lesk, (1987) J. Mol. Biol, 196:901-917; Chothia et al, Nature, (1989) 342:878-883; and Al-Lazikani et al., (1997) JMB 273, 927-948), all of which references are hereby incorporated by reference in their entirety. In some embodiments the amino sequence and/or location of CDRs of an antibody can be identified using the AbM method and/or contact method. The "AbM" definition uses an integrated suite of computer programs produced by Oxford Molecular Group that model antibody structure (see e.g., Martin et al, Proc. Natl. Acad. Sci. (USA), 86:9268-9272 (1989); "AbM™, A Computer Program for Modeling Variable Regions of Antibodies," Oxford, UK; Oxford Molecular, Ltd, all of which are hereby incorporated by reference in their entirety). The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl, 3:194-198 (1999), which is hereby incorporated by reference. In certain embodiments, a contact definition is based on an analysis of the available complex crystal structures (see e.g., MacCallum et ah, J. Mol. Biol, 5:732-45 (1996) which is hereby incorporated by reference).

In some embodiments, the CDR regions in a heavy chain are referred to as H1 (or alternatively CDR1, CDR1-HC, CDR-H1), H2 (or alternatively CDR2, CDR2-HC, CDR-H2), and H3 (or alternatively CDR3, CDR3-HC, CDR-H3) and are numbered sequentially in the direction from the amino terminus to the carboxy terminus. In certain embodiments the CDR regions in the light chain are referred to as L1 (or alternatively CDR1, CDR1-LC, CDR-L1), L2 (or alternatively CDR2, CDR2-LC, CDR-L2) and L3 (or alternatively CDR3, CDR3-LC, CDR-L3) and are numbered sequentially in the direction from the amino terminus to the carboxy terminus.

In some embodiments an antibody binding agent comprises one or more light chain CDRs with at least 70%, 75%, 85%, 86%, 87%, 88%, 89%, 90%, 91%, 92%, 93%, 94%, 95%, 96%, 97%, 98%, or at least 99% identity to any one of the CDRs of Tables 1, 2 or 3. In some embodiments an antibody binding agent comprises a CDR-L1 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 1. In some embodiments an antibody binding agent comprises a CDR-L1 of any one of the sequences shown in Table 1.

TABLE 1

| CDR-L1 Sequences | |
|---|---|
| SEQ ID NO: 4 (C8-L1.4) | QSIVHNNGNTY |
| SEQ ID NO: 5 (C8-L1.5) | QSIVHNNGNTYLE |
| SEQ ID NO: 6 (C8-L1.6) | RSSQSIVHNNGNTY |
| SEQ ID NO: 7 (C8-L1.7) | RSSQSIVHNNGNTYLE |
| SEQ ID NO: 30 (R2D2-L1.30) | LLNSRNQK |
| SEQ ID NO: 31 (R2D2-L1.31) | SLLNSRNQKK |
| SEQ ID NO: 32 (R2D2-L1.32) | KSLLNSRNQKKY |
| SEQ ID NO: 33 (R2D2-L1.33) | RKSLLNSRNQKKYL |

In some embodiments an antibody binding agent comprises a CDR-L2 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 2. In some embodiments an antibody binding agent comprises a CDR-L2 of any one of the sequences shown in Table 2.

TABLE 2

| CDR-L2 Sequences | |
|---|---|
| SEQ ID NO: 8 (C8-L2.8) | KVS |
| SEQ ID NO: 9 (C8-L2.9) | KVSNRF |
| SEQ ID NO: 10 (C8-L2.10) | VSNRFS |
| SEQ ID NO: 11 (C8-L2.11) | KVSNRFS |
| SEQ ID NO: 34 (R2D2-L2.34) | FAS |

TABLE 2-continued

CDR-L2 Sequences

| | | |
|---|---|---|
| SEQ ID NO: 35 | (R2D2-L2.35) | DFASI |
| SEQ ID NO: 36 | (R2D2-L2.36) | GDFASIS |
| SEQ ID NO: 37 | (R2D2-L2.37) | LGDFASISE |

In some embodiments an antibody binding agent comprises a CDR-L3 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 3. In some embodiments an antibody binding agent comprises a CDR-L3 of any one of the sequences shown in Table 3.

TABLE 3

CDR-L3 Sequences

| | | |
|---|---|---|
| SEQ ID NO: 12 | (C8-L3.12) | VYYCFQGSHV |
| SEQ ID NO: 13 | (C8-L3.13) | VYYCFQGSHVPLT |
| SEQ ID NO: 14 | (C8-L3.14) | DLGVYYCFQGSHV |
| SEQ ID NO: 15 | (C8-L3.15) | DLGVYYCFQGSHVPLT |
| SEQ ID NO: 38 | (R2D2-L3.38) | QHYSTP |
| SEQ ID NO: 39 | (R2D2-L3.39) | QQHYSTP |
| SEQ ID NO: 40 | (R2D2-L3.40) | CQQHYSTP |
| SEQ ID NO: 41 | (R2D2-L3.41) | FCQQHYSTP |
| SEQ ID NO: 42 | (R2D2-L3.42) | LADYFCQQHYSTP |

In some embodiments an antibody binding agent comprises one or more heavy chain CDRs with at least 70%, 75%, 85%, 86%, 87%, 88%, 89%, 90%, 91%, 92%, 93%, 94%, 95%, 96%, 97%, 98%, or at least 99% identity to any one of the CDRs of Tables 4, 5 or 6. In some embodiments an antibody binding agent comprises a CDR-H1 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 4. In some embodiments an antibody binding agent comprises a CDR-H1 of any one of the sequences shown in Table 4.

TABLE 4

CDR-H1 Sequences

| | | |
|---|---|---|
| SEQ ID NO: 16 | (C8-H1.16) | SFTGYT |
| SEQ ID NO: 17 | (C8-H1.17) | GYSFTGYT |
| SEQ ID NO: 18 | (C8-H1.18) | SFTGYTMN |
| SEQ ID NO: 19 | (C8-H1.19) | GYSFTGYTMN |
| SEQ ID NO: 43 | (R2D2-H1.43) | GFSLTSY |
| SEQ ID NO: 44 | (R2D2-H1.44) | SGFSLTSYG |
| SEQ ID NO: 45 | (R2D2-H1.45) | VSGFSLTSYGV |
| SEQ ID NO: 46 | (R2D2-H1.46) | TVSGFSLTSYGVH |
| SEQ ID NO: 55 | (X1-H1.55) | SFTGYF |
| SEQ ID NO: 56 | (X1-H1.56) | GYSFTGYF |

TABLE 4-continued

CDR-H1 Sequences

| | | |
|---|---|---|
| SEQ ID NO: 57 | (X1-H1.57) | SFTGYFMN |
| SEQ ID NO: 58 | (X1-H1.58) | GYSFTGYFMN |

In some embodiments an antibody binding agent comprises a CDR-H2 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 5. In some embodiments an antibody binding agent comprises a CDR-H2 of any one of the sequences shown in Table 5.

TABLE 5

CDR-H2 Sequences

| | | |
|---|---|---|
| SEQ ID NO: 20 | (C8-H2.20) | INPYNGDS |
| SEQ ID NO: 21 | (C8-H2.21) | RINPYNGDSFY |
| SEQ ID NO: 22 | (C8-H2.22) | INPYNGDSFYNQKF |
| SEQ ID NO: 23 | (C8-H2.23) | RINPYNGDSFYNQKF |
| SEQ ID NO: 47 | (R2D2-H2.47) | WSGGS |
| SEQ ID NO: 48 | (R2D2-H2.48) | IWSGGST |
| SEQ ID NO: 49 | (R2D2-H2.49) | VIWSGGSTD |
| SEQ ID NO: 50 | (R2D2-H2.50) | GVIWSGGSTDY |
| SEQ ID NO: 59 | (X1-H2.59) | INPYNGDT |
| SEQ ID NO: 60 | (X1-H2.60) | RINPYNGDTFY |
| SEQ ID NO: 61 | (X1-H2.61) | INPYNGDTFYNQKF |
| SEQ ID NO: 62 | (X1-H2.62) | RINPYNGDTFYNQKF |

In some embodiments an antibody binding agent comprises a CDR-H3 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 6. In some embodiments an antibody binding agent comprises a CDR-H3 of any one of the sequences shown in Table 6.

TABLE 6

CDR-H3 Sequences

| | | |
|---|---|---|
| SEQ ID NO: 24 | (C8-H3.24) | SGDGPWF |
| SEQ ID NO: 25 | (C8-H3.25) | DGPWFAY |
| SEQ ID NO: 26 | (C8-H3.26) | GRSGDGPWF |
| SEQ ID NO: 27 | (C8-H3.27) | GRSGDGPWFAY |
| SEQ ID NO: 51 | (R2D2-H3.51) | ARRRRST |
| SEQ ID NO: 52 | (R2D2-H3.52) | CARRRRSTA |
| SEQ ID NO: 53 | (R2D2-H3.53) | YCARRRRSTAM |
| SEQ ID NO: 54 | (R2D2-H3.54) | YYCARRRRSTAMD |
| SEQ ID NO: 63 | (X1-H3.63) | LNYRG |
| SEQ ID NO: 64 | (X1-H3.64) | LNYRGAY |

TABLE 6-continued

CDR-H3 Sequences

| SEQ ID NO: 65 (X1-H3.65) | ARLNYRG |
|---|---|
| SEQ ID NO: 66 (X1-H3.66) | ARLNYRGAY |

In some embodiments an antibody binding agent herein comprises one or more CDRs of the light chain variable region of SEQ ID NO:2. In some embodiments an antibody binding agent comprises one or more CDRs that are at least 70%, 75%, 85%, 86%, 87%, 88%, 89%, 90%, 91%, 92%, 93%, 94%, 95%, 96%, 97%, 98%, or at least 99% identical to a CDR of SEQ ID NO:2. In some embodiments an antibody binding agent herein comprises one or more light chain CDRs of SEQ ID NO:2 that can be identified by a suitable method described herein or known in the art. In some embodiments an antibody binding agent comprises one or more light chains that are at least 70%, 75%, 85%, 86%, 87%, 88%, 89%, 90%, 91%, 92%, 93%, 94%, 95%, 96%, 97%, 98%, or at least 99% identical to the light chain of SEQ ID NO:2. In some embodiments an antibody binding agent herein comprises or consists of a light chain variable region of SEQ ID NO:2.

In some embodiments an antibody binding agent herein comprises one or more CDRs of the light chain variable region of SEQ ID NO:28. In some embodiments an antibody binding agent comprises one or more CDRs that are at least 70%, 75%, 85%, 86%, 87%, 88%, 89%, 90%, 91%, 92%, 93%, 94%, 95%, 96%, 97%, 98%, or at least 99% identical to a CDR of SEQ ID NO:28. In some embodiments an antibody binding agent herein comprises one or more light chain CDRs of SEQ ID NO:28 that can be identified by a suitable method described herein or known in the art. In some embodiments an antibody binding agent comprises one or more light chains that are at least 70%, 75%, 85%, 86%, 87%, 88%, 89%, 90%, 91%, 92%, 93%, 94%, 95%, 96%, 97%, 98%, or at least 99% identical to the light chain of SEQ ID NO:28. In some embodiments an antibody binding agent herein comprises or consists of a light chain variable region of SEQ ID NO:28.

In some embodiments an antibody binding agent herein comprises a one or more CDRs of the heavy chain variable region of SEQ ID NO:3. In some embodiments an antibody binding agent comprises one or more CDRs that are at least 70%, 75%, 85%, 86%, 87%, 88%, 89%, 90%, 91%, 92%, 93%, 94%, 95%, 96%, 97%, 98%, or at least 99% identical to a CDR of SEQ ID NO:3. In some embodiments an antibody binding agent herein comprises one or more heavy chain CDRs of SEQ ID NO:3 that can be identified by a suitable method described herein or known in the art. In some embodiments an antibody binding agent comprises one or more light chains that are at least 70%, 75%, 85%, 86%, 87%, 88%, 89%, 90%, 91%, 92%, 93%, 94%, 95%, 96%, 97%, 98%, or at least 99% identical to the light chain of SEQ ID NO:3. In some embodiments an antibody binding agent herein comprises or consists of a heavy chain variable region of SEQ ID NO:3.

In some embodiments an antibody binding agent herein comprises a one or more CDRs of the heavy chain variable region of SEQ ID NO:67. In some embodiments an antibody binding agent comprises one or more CDRs that are at least 70%, 75%, 85%, 86%, 87%, 88%, 89%, 90%, 91%, 92%, 93%, 94%, 95%, 96%, 97%, 98%, or at least 99% identical to a CDR of SEQ ID NO:67. In some embodiments an antibody binding agent herein comprises one or more heavy chain CDRs of SEQ ID NO:67 that can be identified by a suitable method described herein or known in the art. In some embodiments an antibody binding agent comprises one or more light chains that are at least 70%, 75%, 85%, 86%, 87%, 88%, 89%, 90%, 91%, 92%, 93%, 94%, 95%, 96%, 97%, 98%, or at least 99% identical to the light chain of SEQ ID NO:67. In some embodiments an antibody binding agent herein comprises or consists of a heavy chain variable region of SEQ ID NO:67.

In some embodiments an antibody binding agent herein comprises a one or more CDRs of the heavy chain variable region of SEQ ID NO:29. In some embodiments an antibody binding agent comprises one or more CDRs that are at least 70%, 75%, 85%, 86%, 87%, 88%, 89%, 90%, 91%, 92%, 93%, 94%, 95%, 96%, 97%, 98%, or at least 99% identical to a CDR of SEQ ID NO:29. In some embodiments an antibody binding agent herein comprises one or more heavy chain CDRs of SEQ ID NO:29 that can be identified by a suitable method described herein or known in the art. In some embodiments an antibody binding agent comprises one or more light chains that are at least 70%, 75%, 85%, 86%, 87%, 88%, 89%, 90%, 91%, 92%, 93%, 94%, 95%, 96%, 97%, 98%, or at least 99% identical to the light chain of SEQ ID NO:29. In some embodiments an antibody binding agent herein comprises or consists of a heavy chain variable region of SEQ ID NO:29.

In some embodiments an antibody binding agent comprises a light chain variable region that is at least 70%, 75%, 85%, 86%, 87%, 88%, 89%, 90%, 91%, 92%, 93%, 94%, 95%, 96%, 97%, 98%, or at least 99% identical to SEQ ID NO:2, and a heavy chain variable region that is at least 70%, 75%, 85%, 86%, 87%, 88%, 89%, 90%, 91%, 92%, 93%, 94%, 95%, 96%, 97%, 98%, or at least 99% identical to SEQ ID NO:3. In some embodiments an antibody binding agent herein comprises CDR-L1, CDR-L2, and CDR-L3 of SEQ ID NO:2 and CDR-H1, CDR-H2, and CDR-H3 of SEQ ID NO:3, where each of the CDRs are identified by a suitable method. In some embodiments an antibody binding agent herein comprises or consist of a light chain variable region of SEQ ID NO:2 and a heavy chain variable region of SEQ ID NO:3.

In some embodiments an antibody binding agent comprises a light chain variable region that is at least 70%, 75%, 85%, 86%, 87%, 88%, 89%, 90%, 91%, 92%, 93%, 94%, 95%, 96%, 97%, 98%, or at least 99% identical to SEQ ID NO:2, and a heavy chain variable region that is at least 70%, 75%, 85%, 86%, 87%, 88%, 89%, 90%, 91%, 92%, 93%, 94%, 95%, 96%, 97%, 98%, or at least 99% identical to SEQ ID NO:67. In some embodiments an antibody binding agent herein comprises CDR-L1, CDR-L2, and CDR-L3 of SEQ ID NO:2 and CDR-H1, CDR-H2, and CDR-H3 of SEQ ID NO:67, where each of the CDRs are identified by a suitable method. In some embodiments an antibody binding agent herein comprises or consist of a light chain variable region of SEQ ID NO:2 and a heavy chain variable region of SEQ ID NO:67.

In some embodiments an antibody binding agent comprises a light chain variable region that is at least 70%, 75%, 85%, 86%, 87%, 88%, 89%, 90%, 91%, 92%, 93%, 94%, 95%, 96%, 97%, 98%, or at least 99% identical to SEQ ID NO:28, and a heavy chain variable region that is at least 70%, 75%, 85%, 86%, 87%, 88%, 89%, 90%, 91%, 92%, 93%, 94%, 95%, 96%, 97%, 98%, or at least 99% identical to SEQ ID NO:29. In some embodiments an antibody binding agent herein comprises or consist of a light chain variable region of SEQ ID NO:28 and a heavy chain variable region of SEQ ID NO:29. In some embodiments an antibody binding agent herein comprises CDR-L1, CDR-L2, and CDR-L3 of SEQ ID NO:28 and CDR-H1, CDR-H2, and CDR-H3 of SEQ ID NO:29, where each of the CDRs are identified by a suitable method.

An antibody binding agent, whether natural or recombinant, can be a monoclonal (e.g., a monoclonal antibody, or portion thereof). In some embodiments an antibody, or fragment thereof is chimeric, humanized or bispecific. Chimeric antibodies often comprise a mixture of portions of binding agents or antibodies derived from different species. In some embodiments chimeric antibodies comprise fully synthetic portions or sequences of amino acids not found in native antibody molecules. In some embodiments chimeric antibodies comprise amino acid substitutions derived from antibodies of other species or, in some embodiments chimeric antibodies comprise amino acid substitutions added in an attempt to increase binding affinity (e.g., by an in vitro process of affinity maturation) or alter antibody function (e.g., to increase or decrease complement mediated or cell mediated cell lysis).

In certain embodiments, modification of an antibody by methods known in the art is typically designed to achieve increased binding affinity for a target and/or to reduce immunogenicity of the antibody in the recipient. In certain embodiments, humanized antibodies are modified to eliminate glycosylation sites in order to increase affinity of the antibody for its cognate antigen. See e.g., Co et al, Mol. Immunol, 30:1361-1367 (1993). In certain embodiments, techniques such as "reshaping," "hyperchimerization," or "veneering/resurfacing" can be used to produce humanized antibodies. See e.g., Vaswami et al, Annals of Allergy, Asthma, & Immunol. 81:105 (1998); Roguska et al, Prot. Engin., 9:895-904 (1996); and U.S. Pat. No. 6,072,035. In certain such embodiments, these techniques typically reduce antibody immunogenicity by reducing the number of foreign residues, but do not prevent anti-idiotypic and anti-allotypic responses following repeated administration of the antibodies. Certain other methods for reducing immunogenicity are described, e.g., in Gilliland et al, J. Immunol, 62(6):3663-71 (1999).

In some embodiments an antibody binding agent comprises a chimeric antibody, humanized antibody, human antibody, or a portion or fragment thereof. Methods for generating chimeric, grafted and/or humanized antibodies are known (see, e.g., U.S. Pat. Nos. 5,530,101, 5,707,622, 5,994,524 and 6,245,894), which generally involve exchanging an antibody variable region, or portion thereof, from one species (e.g., mouse) into an antibody constant domain of another species (e.g., human). In some embodiments, an antibody can be humanized by exchanging one or more framework regions, or portions thereof (e.g., one or more individual amino acids), with one or more framework regions, or portions thereof (e.g., one or more individual amino acids), from a human antibody. Methods of humanizing an antibody by transferring one or more CDRs (e.g., 1, 2, 3, 4, 5 or all 6 CDRs) from a donor antibody binding agent (e.g., an antibody binding agent comprising framework regions of a mouse monoclonal antibody) to an acceptor antibody binding agent (e.g., an antibody binding agent comprising human framework regions) while retaining antigen binding are known (e.g., see Queen et al., (1988) PNAS 86:10029-10033; Riechmann et al., Nature (1988) 332:323-327; Antibody Engineering: Methods and Protocols, Vol. 248 of Methods in molecular biology, edited by Benny K. C. Lo, Springer Science & Business Media, (2004); Antibody Engineering, Vol. 1, Roland E. Kontermann, Stefan Dübel, Edition 2, Publisher Springer Science & Business Media, (2010)).

In certain embodiments the complementarity determining regions (CDRs) of the light and heavy chain variable regions of an antibody to *A. baumannii* is grafted to framework regions from the same, or another, species. In certain embodiments, the CDRs of the light and heavy chain variable regions of an antibody to *A. baumannii* can be grafted to consensus human framework regions. To create consensus human framework regions, in certain embodiments, framework regions from several human heavy chain or light chain amino acid sequences can be aligned to identify a consensus amino acid sequence. In certain embodiments, the heavy chain or light chain framework regions of an antibody that displays specific binding to *A. baumannii* are replaced with the framework regions, or portions thereof, from a different heavy chain or light chain. In certain embodiments, grafted variable regions are part of a single chain Fv antibody. Additional examples of CDR grafting are described, e.g., in U.S. Pat. Nos. 6,180,370, 6,054,297, 5,693,762, 5,859,205, 5,693,761, 5,565,332, 5,585,089, and 5,530, 101, and in Jones et al, Nature, 321:522-525 (1986); Verhoeyen et al, Science, 239:1534-1536 (1988), and Winter, FEBS Letts., 430:92-94 (1998), which are hereby incorporated by reference.

In some embodiments an antibody binding agent is generated using a light chain, a light chain variable region, or a portion thereof, of known binding specificity and a library of heavy chain variable regions. Using such a method, the library of heavy chain variable regions can comprise a library of one or more heavy chain CDRs. For example, a library of heavy chain variable regions may comprise known framework regions, a known CDR1 and a known CDR2 and a library of different CDR3 regions. In some embodiments, the light chain, or portion thereof, of known binding specificity is co-expressed with a library of heavy chain variable regions, and the resulting light chain/heavy chain proteins are screened for binding to an antigen of interest (e.g., an *A. baumannii* antigen) and/or for a specific function (e.g., blocking of *A. baumannii* induced sepsis). Alternatively, in some embodiments an antibody binding agent is generated using a heavy chain, a heavy chain variable region, or a portion thereof, of known binding specificity and a library of light chain variable regions. Such methods of screening and optimizing antibody binding agents are known (e.g., see Portolano et al., (1993) Journal of Immunology 150:880-887; and Clarkson et al., (1991) Nature 352:624-628, which are hereby incorporated by reference in their entirety). Such references teach methods of producing antibodies that bind a specific antigen by using a specific known variable light chain, variable heavy chain, or a portion thereof (e.g., CDRs thereof) by screening a library of complementary variable domains.

In certain embodiments an antibody binding agent comprises one or more modifications. In some embodiments the number and/or type of glycosylation sites in an antibody binding agent is modified or altered compared to the amino acid sequence of a parent antibody binding agent. In certain embodiments, a modified antibody binding agent comprises a greater or a lesser number of N-linked glycosylation sites than the native protein. An N-linked glycosylation site is often characterized by the sequence Asn-X-Ser or Asn-X-Thr, where the amino acid residue designated as X can be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided in certain embodiments is a rearrangement of N-linked carbohydrate chains where one or more N-linked glycosylation sites (typically those that are naturally occurring) are eliminated and one or more new N-linked sites are created. In some embodiments an antibody binding agent is modified by deleting one or more cysteine residues or substituting one or more cysteine residues for another amino acid (e.g., serine) as compared to an unmodified antibody binding agent. In certain embodiments cysteine variants can be useful when antibodies must be refolded into a biologically active conformation such as after the isolation of insoluble inclusion bodies.

According to certain embodiments an antibody binding agent is modified to include certain amino acid additions, substitutions, or deletions designed to (1) reduce susceptibility of an antibody binding agent to proteolysis, (2) reduce susceptibility of an antibody binding agent to oxidation, (3) alter binding affinity to Fc receptors, (4) alter antigen binding affinity of an antibody binding agent, (4) increase serum half-life and/or (5) confer or modify other physicochemical, pharmacokinetic or functional properties of an antibody binding agent.

An antibody binding agent can be expressed, isolated from and/or purified from a suitable expression system non-limiting examples of which include a suitable bacteria, insect, plant or mammalian expression system. For example, a nucleic acid encoding an antibody binding agent can be introduced into a suitable mammalian cell line that expresses and secretes the antibody binding agent into the cell culture media.

The term "specifically binds" refers to an antibody binding agent binding to a target peptide in preference to binding other molecules or other peptides as determined by, for example, a suitable in vitro assay (e.g., an Elisa, Immunoblot, Flow cytometry, and the like). A specific binding interaction discriminates over non-specific binding interactions by about 2-fold or more, often about 10-fold or more, and sometimes about 100-fold or more, 1000-fold or more, 10,000-fold or more, 100,000-fold or more, or 1,000,000-fold or more.

In some embodiments an antibody binding agent comprises a label. As used herein, the terms "label" or "labeled" refers to incorporation of a detectable marker, e.g., by incorporation of a radiolabeled amino acid or attachment to a polypeptide of biotin moieties that can be detected by marked avidin (e.g., streptavidin containing a fluorescent marker or enzymatic activity that can be detected by optical or colorimetric methods). In certain embodiments, the label or marker can also be therapeutic. Various methods of labeling polypeptides and glycoproteins are known in the art and can be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce potential steric hindrance.

In some embodiments a carrier, anti-bacterial medication, radioisotope and/or a polypeptide can be indirectly or directly associated with, or bound to (e.g., covalently bound to, or conjugated to), an antibody binding agent. In certain embodiments agents or molecules are sometimes conjugated to or bound to antibodies to alter or extend the in vivo half-life of an antibody or fragment thereof. In some embodiments, an antibody binding agent is fused or associated with one or more polypeptides (e.g., a toxin, ligand, receptor, cytokine, antibody, the like or combinations thereof). In certain embodiments, an antibody binding agent is linked to a half-life extending vehicle known in the art. Such vehicles include, but are not limited to, polyethylene glycol, glycogen (e.g., glycosylation of the antigen binding protein), and dextran. Such vehicles are described, e.g., in U.S. application Ser. No. 09/428,082, now U.S. Pat. No. 6,660,843 and published PCT Application No. WO 99/25044, hereby incorporated by reference.

In some embodiments carriers or anti-bacterial medications are bound to an antibody binding agent by a linker. A linker can provide a mechanism for covalently attaching a carrier and/or an anti-bacterial medications to an antibody binding agent. Any suitable linker can be used in a composition or method described herein. Non-limiting examples of suitable linkers include silanes, thiols, phosphonic acid, and polyethylene glycol (PEG). Methods of attaching two or more molecules using a linker are well known in the art and are sometimes referred to as "crosslinking". Non-limiting examples of crosslinking include an amine reacting with a N-Hydroxysuccinimide (NHS) ester, an imidoester, a pentafluorophenyl (PFP) ester, a hydroxymethyl phosphine, an oxirane or any other carbonyl compound; a carboxyl reacting with a carbodiimide; a sulfhydryl reacting with a maleimide, a haloacetyl, a pyridyldisulfide, and/or a vinyl sulfone; an aldehyde reacting with a hydrazine; any non-selective group reacting with diazirine and/or aryl azide; a hydroxyl reacting with isocyanate; a hydroxylamine reacting with a carbonyl compound; the like and combinations thereof.

The term "percent identical" or "percent identity" refers to sequence identity between two amino acid sequences. Identity can be determined by comparing a position in each sequence which may be aligned for purposes of comparison. When an equivalent position in the compared sequences is occupied by the same amino acid, then the molecules are identical at that position. When the equivalent site is occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. In some embodiments an alignment program that permits gaps in the sequence is utilized to align the sequences. The Smith-Waterman is one type of algorithm that permits gaps in sequence alignments. See Meth. Mol. Biol. 70:173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

Anti-Bacteria Medications

Any suitable anti-bacteria medication, or combinations thereof, can be used for a composition or method described herein. In some embodiments an anti-bacteria medication is any suitable antibiotic used for the treatment or prevention of a bacteria infection. In some embodiments an anti-bacteria medication is any suitable antibiotic used for the treatment or prevention of an *A. baumannii* infection. Non-limiting examples of anti-bacteria medications include ampicillin, amoxicillin, amikacin, aminoglycosides (e.g., tobramycin and/or amikacin), aminocyclitols, cefotaxime, chloramphenicol, cephalosporins, ciprofloxacin, clindamycin, colistin, fluoroquinolones, gentamicin, β-lactams (e.g., carbapenems, ceftazidime, thienamycin, imipenem, meropenem, erythromycin, ertapenem, doripenem, panipenem/betamipron, razupenem, tebipenem, lenapenem, tomopenem and biapenem; cephalosporins; penicillin derivatives (penams); monobactams; and the like), meclocycline, netrilaicin, norfloxacin, polymyxins (e.g., polymyxin B, polymyxin E (colistin), and the like), penicillins, piperacillin, lactamase inhibitors (e.g., sulbactam, clavulanic acid, tazobactam, avibactam and the like), rifamycins, lipiarmycins, quinolones, sulfonamides, macrolides, lincosamides, tetracyclines, cyclic lipopeptides (e.g., daptomycin), oxazolidinones (e.g., linezolid), lipiarmycins (e.g., fidaxomicin) and/or glycylcycline agents (e.g., tigecycline)), combinations thereof, derivative thereof and the like.

Pharmaceutical Compositions

In some embodiments a pharmaceutical composition comprises an antibody binding agent that binds specifically to *A. baumannii* as described herein. In some embodiments a pharmaceutical composition comprises an antibody binding agent that binds specifically to *A. baumannii*, and an anti-bacterial medication.

In certain embodiments, acceptable pharmaceutical compositions are nontoxic to recipients at the dosages and concentrations employed. A pharmaceutical composition can be formulated for a suitable route of administration. In some embodiments a pharmaceutical composition is formulated for subcutaneous (s.c.), intradermal, intramuscular, intraperitoneal and/or intravenous (i.v.) administration. In certain embodiments, a pharmaceutical composition can contain formulation materials for modifying, maintaining, or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates (e.g., phosphate buffered saline) or suitable organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); solvents (such as glycerin, propylene glycol or polyethylene glycol); diluents; excipients and/or pharmaceutical adjuvants (Remington's Pharmaceutical Sciences, 18th Ed., A. R. Gennaro, ed., Mack Publishing Company (1995)).

In certain embodiments, a pharmaceutical composition comprises a suitable excipient, non-limiting example of which include anti-adherents (e.g., magnesium stearate), binders, fillers, monosaccharides, disaccharides, other carbohydrates (e.g., glucose, mannose or dextrins), sugar alcohols (e.g., mannitol or sorbitol), coatings (e.g., cellulose, hydroxypropyl methylcellulose (HPMC), microcrystalline cellulose, synthetic polymers, shellac, gelatin, corn protein zein, enterics or other polysaccharides), starch (e.g., potato, maize or wheat starch), silica, colors, disintegrants, flavors, lubricants, preservatives, sorbents, sweeteners, vehicles, suspending agents, surfactants and/or wetting agents (such as pluronics, PEG, sorbitan esters, polysorbates such as polysorbate 20, polysorbate 80, triton, tromethamine, lecithin, cholesterol, tyloxapal), stability enhancing agents (such as sucrose or sorbitol), and tonicity enhancing agents (such as alkali metal halides, sodium or potassium chloride, mannitol, sorbitol), and/or any excipient disclosed in Remington's Pharmaceutical Sciences, 18th Ed., A. R. Gennaro, ed., Mack Publishing Company (1995).

In some embodiments a pharmaceutical composition comprises a suitable pharmaceutically acceptable additive and/or carrier. Non-limiting examples of suitable additives include a suitable pH adjuster, a soothing agent, a buffer, a sulfur-containing reducing agent, an antioxidant and the like. Non-limiting examples of a sulfur-containing reducing agents include those having a sulfhydryl group such as N-acetylcysteine, N-acetylhomocysteine, thioctic acid, thiodiglycol, thioethanolamine, thioglycerol, thiosorbitol, thioglycolic acid and a salt thereof, sodium thiosulfate, glutathione, and a C1-C7 thioalkanoic acid. Non-limiting examples of an antioxidant include erythorbic acid, dibutyl-hydroxytoluene, butylhydroxyanisole, alpha-tocopherol, tocopherol acetate, L-ascorbic acid and a salt thereof, L-ascorbyl palmitate, L-ascorbyl stearate, sodium bisulfite, sodium sulfite, triamyl gallate and propyl gallate, as well as chelating agents such as disodium ethylenediaminetetraacetate (EDTA), sodium pyrophosphate and sodium metaphosphate. Furthermore, diluents, additives and excipients may comprise other commonly used ingredients, for example, inorganic salts such as sodium chloride, potassium chloride, calcium chloride, sodium phosphate, potassium phosphate and sodium bicarbonate, as well as organic salts such as sodium citrate, potassium citrate and sodium acetate.

The pharmaceutical compositions used herein can be stable over an extended period of time, for example on the order of months or years. In some embodiments a pharmaceutical composition comprises one or more suitable preservatives. Non limiting examples of preservatives include benzalkonium chloride, benzoic acid, salicylic acid, thimerosal, phenethyl alcohol, methylparaben, propylparaben, chlorhexidine, sorbic acid, hydrogen peroxide, the like and/or combinations thereof. A preservative can comprise a quaternary ammonium compound, such as benzalkonium chloride, benzoxonium chloride, benzethonium chloride, cetrimide, sepazonium chloride, cetylpyridinium chloride, or domiphen bromide (BRADOSOL®). A preservative can comprise an alkyl-mercury salt of thiosalicylic acid, such as thimerosal, phenylmercuric nitrate, phenylmercuric acetate or phenylmercuric borate. A preservative can comprise a paraben, such as methylparaben or propylparaben. A preservative can comprise an alcohol, such as chlorobutanol, benzyl alcohol or phenyl ethyl alcohol. A preservative can comprise a biguanide derivative, such as chlorohexidine or polyhexamethylene biguanide. A preservative can comprise sodium perborate, imidazolidinyl urea, and/or sorbic acid. A preservative can comprise stabilized oxychloro complexes, such as known and commercially available under the trade name PURITE®. A preservative can comprise polyglycol-polyamine condensation resins, such as known and commercially available under the trade name POLYQUART® from Henkel KGaA. A preservative can comprise stabilized hydrogen peroxide. A preservative can be benzalkonium chloride. In some embodiments a pharmaceutical composition is free of preservatives.

In some embodiments a pharmaceutical composition is substantially free of serum proteins. In some embodiments a pharmaceutical composition is sterile. In some embodiments a pharmaceutical composition is lyophilized to a dry powder form, which is suitable for reconstitution with a suitable pharmaceutical solvent (e.g., water, saline, an isotonic buffer solution (e.g., PBS), and the like), which reconstituted form is suitable for parental administration (e.g., intravenous administration) to a mammal.

The pharmaceutical compositions described herein may be configured for administration to a subject in any suitable form and/or amount according to the therapy in which they are employed. For example, a pharmaceutical composition configured for parenteral administration (e.g., by injection or infusion), may take the form of a suspension, solution or emulsion in an oily or aqueous vehicle and it may contain formulation agents, excipients, additives and/or diluents such as aqueous or non-aqueous solvents, co-solvents, suspending solutions, preservatives, stabilizing agents and or dispersing agents. In some embodiments a pharmaceutical composition suitable for parental administration may contain, in addition to an antibody binding agent and/or one or more anti-bacterial medications, one or more excipients.

In some embodiments a pharmaceutical compositions described herein may be configured for topical, rectal, or vaginal administration and may include one or more of a binding and/or lubricating agent, polymeric glycols, gelatins, cocoa-butter or other suitable waxes or fats. In some embodiments, a pharmaceutical composition described herein is incorporated into a topical formulation containing a topical carrier that is generally suited to topical drug administration and comprising any suitable material known in the art. A topical carrier may be selected so as to provide the composition in the desired form, e.g., as a solution or suspension, an ointment, a lotion, a cream, a salve, an emulsion or microemulsion, a gel, an oil, a powder, or the like. It may be comprised of naturally occurring or synthetic materials, or both. A carrier for the active ingredient may also be in a spray form. It is preferable that the selected carrier not adversely affect the active agent or other components of the topical formulation. Non-limiting examples of suitable topical carriers for use herein can be soluble, semi-solid or solid and include water, alcohols and other nontoxic organic solvents, glycerin, mineral oil, silicone, petroleum jelly, lanolin, fatty acids, vegetable oils, parabens, waxes, and the like. Semisolid carriers preferably have a dynamic viscosity greater than that of water. Other suitable vehicles include ointment bases, conventional creams such as HEB cream; gels; as well as petroleum jelly and the like. If desired, and depending on the carrier, the compositions may be sterilized or mixed with auxiliary agents, e.g., preservatives, stabilizers, wetting agents, buffers, or salts for influencing osmotic pressure and the like. Formulations may be colorless, odorless ointments, lotions, creams, microemulsions and gels.

Ointments can be semisolid preparations which are typically based on petrolatum or other petroleum derivatives. The specific ointment base to be used, as will be appreciated by those skilled in the art, is one that will provide for optimum delivery of the active agent, and, preferably, will provide for other desired characteristics as well, e.g., emolliency or the like. As with other carriers or vehicles, an ointment base should be inert, stable, nonirritating and nonsensitizing. Ointment bases can be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (OAV) emulsions, and include, for example, cetyl alcohol, glyceryl monostearate, lanolin and stearic acid. Exemplary water-soluble ointment bases are prepared from polyethylene glycols (PEGs) of varying molecular weight, e.g., polyethylene glycol-1000 (PEG-1000). Oils of animal or plant origin such as peanut oil, mineral oil, soybean oil, or sesame oil, corn oil, or synthetic oils may be added.

Antibody binding agents and/or peptides may be incorporated into lotions, which generally are preparations to be applied to the skin surface without friction, and are typically liquid or semiliquid preparations in which solid particles, including the active agent, are present in a water or alcohol base. Lotions can be suspensions of solids, and may comprise a liquid oily emulsion of the oil-in-water type. In certain embodiments, lotions are preferred formulations for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like. In some embodiments a lotion formulation for use in conjunction with the present method contains propylene glycol mixed with a hydrophilic petrolatum.

In some embodiments pharmaceutical compositions are formulated as creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation can be a nonionic, anionic, cationic or amphoteric surfactant.

Pharmaceutical compositions can be formulated as microemulsions, which generally are thermodynamically stable, isotropic clear dispersions of two immiscible liquids, such as oil and water, stabilized by an interfacial film of surfactant molecules (Encyclopedia of Pharmaceutical Technology (New York: Marcel Dekker, 1992), volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifier") is generally selected from the group of polyglycerol derivatives, glycerol derivatives and fatty alcohols. In some embodiments emulsifier/co-emulsifier combinations are selected from the group consisting of: glyceryl monostearate and polyoxyethylene stearate; polyethylene glycol and ethylene glycol palmitostearate; and caprylic and capric triglycerides and oleoyl macrogolglycerides. In certain embodiments a water phase includes not only water, but also, typically, buffers, glucose, propylene glycol, polyethylene glycols, for example lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG, etc.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In some embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising an antibody binding agent, with or without at least one additional therapeutic agents, can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising an antibody binding agent, with or without at least one additional therapeutic agents, can be formulated as a lyophilized form (e.g., a lyophilized powder or crystalline form, a freeze dried form) using appropriate excipients such as sucrose.

In some embodiments a carrier facilitates the incorporation of a compound into cells or tissues. For example dimethyl sulfoxide (DMSO) is a commonly utilized carrier as it facilitates the uptake of many organic compounds into the cells or tissues of an organism. In some embodiments, a pharmaceutical carrier for a composition described herein can be selected from castor oil, ethylene glycol, monobutyl ether, diethylene glycol monoethyl ether, corn oil, dimethyl sulfoxide, ethylene glycol, isopropanol, soybean oil, glycerin, zinc oxide, titanium dioxide, glycerin, butylene glycol, cetyl alcohol, and sodium hyaluronate.

The compounds and compositions used herein can include any suitable buffers, such as for example, sodium citrate buffer and/or sequestering agents, such as an EDTA sequestering agent. Ingredients, such as meglumine, may be added to adjust the pH of a composition or antibody binding agent described herein. Antibody binding agents and compositions described herein may comprise sodium and/or iodine, such as organically bound iodine. Compositions and compounds used herein may be provided in a container in which the air is replaced by another substance, such as nitrogen.

In certain embodiments, the optimal pharmaceutical composition will be determined by one skilled in the art depending upon, for example, the intended route of administration, delivery format and desired dosage (see e.g., Remington's Pharmaceutical Sciences, supra). In certain embodiments, such compositions may influence the physical state, stability, rate of in vivo release and rate of in vivo clearance of the antibodies of the invention.

Administration and Formulation

In some embodiments, compositions described herein (e.g., compositions comprising a mAb that binds to *A. baumannii*) are used to prevent and/or block an *A. baumannii* infection. In certain embodiments a composition is administered to a subject at risk of acquiring an *A. baumannii* infection. A composition that is used to prevent an *A. baumannii* infection is often administered to a subject at risk of acquiring an *A. baumannii* infection. In certain embodiments a method of preventing an *A. baumannii* infection comprises administering a composition described herein prior to detection or diagnosis of an *A. baumannii* infection. Any suitable method of administering a pharmaceutical composition to a subject can be used to administer an antibody binding agent described herein.

The exact formulation and route of administration for a composition for use according to the methods of the invention described herein can be chosen by the individual physician in view of the patient's condition. See, e.g., Fingl et al. 1975, in "The Pharmacological Basis of Therapeutics," Ch. 1, p. 1; which is incorporated herein by reference in its entirety. Any suitable route of administration can be used for administration of a pharmaceutical composition or antibody binding agent described herein. Non-limiting examples of routes of administration include topical or local (e.g., transdermally or cutaneously, (e.g., on the skin or epidermus), in or on the eye, intranasally, transmucosally, in the ear, inside the ear (e.g., behind the ear drum)), enteral (e.g., delivered through the gastrointestinal tract, e.g., orally (e.g., as a tablet, capsule, granule, liquid, emulsification, lozenge, or combination thereof), sublingual, by gastric feeding tube, rectally, and the like), by parenteral administration (e.g., parenterally, e.g., intravenously, intra-arterially, intramuscularly, intraperitoneally, intradermally, subcutaneously, intracavity, intracranially, intra-articular, into a joint space, intracardiac (into the heart), intracavernous injection, intralesional (into a skin lesion), intraosseous infusion (into the bone marrow), intrathecal (into the spinal canal), intrauterine, intravaginal, intravesical infusion, intravitreal), the like or combinations thereof.

In some embodiments a composition herein is provided to a subject. A composition that is provided to a subject is often provided to a subject for self-administration or for administration to a subject by another (e.g., a non-medical professional). For example a composition described herein can be provided as an instruction written by a medical practitioner that authorizes a patient to be provided a composition or treatment described herein (e.g., a prescription). In another example, a composition can be provided to a subject where the subject self-administers a composition orally, intravenously or by way of an inhaler, for example.

Pharmaceutical composition or antibody binding agents herein can be formulated to be compatible with a particular route of administration or use. Compositions for parenteral, intradermal, or subcutaneous administration can include a sterile diluent, such as water, saline solution, fixed oils, polyethylene glycols, glycerin, propylene glycol or other synthetic solvents. The preparation may contain one or more preservatives to prevent microorganism growth (e.g., antibacterial agents such as benzyl alcohol or methyl parabens; antioxidants such as ascorbic acid or sodium bisulfite; chelating agents such as EDTA; buffers such as acetates, citrates or phosphates and agents for the adjustment of tonicity such as sodium chloride or dextrose). In certain embodiments, a composition herein is substantially free of a chelator (e.g., a zinc chelator, e.g., EDTA or EGTA).

Compositions for injection include sterile aqueous solutions (where water soluble) or dispersions and sterile powders (e.g., sterile lyophilized preparations) for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (e.g., glycerol, propylene glycol, and polyethylene glycol), and suitable mixtures thereof. Fluidity can be maintained, for example, by the use of a coating such as lecithin, or by the use of surfactants. Antibacterial and anti-bacterial agents include, for example, parabens, chlorobutanol, phenol, ascorbic acid and thimerosal. Including an agent that delays absorption, for example, aluminum monostearate and gelatin can prolonged absorption of injectable compositions. Polysorbate 20 and polysorbate 80 can be added into the formulation mixture, for example, up to 1%. Other non-limiting additives include histidine HCl, α,α-trehalose dehydrate.

Alternately, one can administer compositions for use according to the methods of the invention in a local rather than systemic manner, for example, via direct application to the skin, mucous membrane or region of interest for treating, including using a depot or sustained release formulation.

In some embodiments, a pharmaceutical composition comprising an antibody binding agent can be administered alone. In other embodiments, a pharmaceutical composition comprising an antibody binding agent can be administered in combination with one or more additional materials, for example, as two separate compositions or as a single composition where the additional material(s) is (are) mixed or formulated together with the pharmaceutical composition. For example, without being limited thereto, the pharmaceutical composition can be formulated with additional excipients, additional active ingredients, other pharmaceutical compositions, anti-bacterial medications or other antibody binding agents.

The pharmaceutical compositions can be manufactured by any suitable manner, including, e.g., by means of conventional mixing, dissolving, granulating, dragee-making, levigating, emulsifying, encapsulating, entrapping or tableting processes.

Pharmaceutical compositions for use in accordance with the invention thus can be formulated in any suitable manner using one or more physiologically acceptable carriers comprising excipients and auxiliaries, which facilitate processing of the active compounds into preparations which can be used pharmaceutically. Proper formulation can depend upon the route of administration chosen. In particular, any suitable formulation, ingredient, excipient, the like or combinations thereof as listed in "Remington's Pharmaceutical Sciences," Mack Publishing Co., Easton, Pa., 18th edition, 1990. can be used with a composition described herein. The various antibody binding agents and compositions described herein, alone or in combination, can be incorporated into or used with the materials described in Remington's. Any suitable techniques, carriers, and excipients can be used, including those understood in the art; e.g., in Remington's Pharmaceutical Sciences, above, all pages of which are incorporated herein by reference in their entirety, including without limitation for all of the types of formulations, methods of making, etc.

In some embodiments, the composition may be formulated, for example, as a topical formulation. The topical formulation may include, for example, a formulation such as a gel, a cream, a lotion, a paste, an ointment, an oil, and a foam. The composition further may include, for example, an absorption emollient.

In some embodiments, at least part of the affected area of the mammal is contacted with the composition on a daily basis, on an as-needed basis, or on a regular interval such as twice daily, three times daily, every other day, etc. The composition can be administered for a period of time ranging from a single as needed administration to administration for 1 day to multiple years, or any value there between, (e.g., 1-90 days, 1-60 days, 1-30 days, etc.). The dosages described herein can be daily dosages or the dosage of an individual administration, for example, even if multiple administrations occur (e.g., 2 sprays into a nostril).

Some embodiments relate to methods of treating or preventing an *A. baumannii* infection through administration of compositions described herein to the upper respiratory track/bronchi in a mammal in need thereof, for example, by contacting at least part of the upper respiratory tract/bronchi of a mammal with a therapeutically effective amount of a composition as described above or elsewhere herein. The composition can be, for example, formulated as an aerosol formulation, including formulated for use in a nebulizer or an inhaler. The composition further may include other pharmaceutically acceptable components such as a preservative.

In certain embodiments, the amount of an antibody binding agent can be any sufficient amount to prevent, treat, reduce the severity of, delay the onset of or alleviate a symptom of an *A. baumannii* as contemplated herein or a specific indication as described herein.

Compositions for use according to the methods of the invention can be, in some embodiments, aerosolized compositions. The aerosolized composition can be formulated such that the composition has increased solubility and/or diffusivity. The composition can comprise a carrier. A carrier can improve the absorption of the composition, change the viscosity of a composition, improve the solubility of the composition, or improve the diffusivity of a composition compared to a pharmaceutical composition that does not comprise a carrier.

Liquid pharmaceutically administrable compositions can, for example, be prepared by dissolving, dispersing, etc. an antibody binding agent as defined above and optional pharmaceutical adjuvants in a carrier (e.g., water, saline, aqueous dextrose, glycerol, glycols, ethanol or the like) to form a solution or suspension. Solutions to be aerosolized can be prepared in any suitable form, for example, either as liquid solutions or suspensions, as emulsions, or in solid forms suitable for dissolution or suspension in liquid prior to aerosol production and inhalation.

For administration by inhalation, the compositions described herein can conveniently be delivered in the form of an aerosol (e.g., through liquid nebulization, dry powder dispersion or meter-dose administration). The aerosol can be delivered from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

For aqueous and other non-pressurized liquid systems, a variety of nebulizers (including small volume nebulizers) can be used to aerosolize the formulations. Compressor-driven nebulizers can utilize jet technology and can use compressed air to generate the liquid aerosol. Such devices are commercially available from, for example, Healthdyne Technologies, Inc.; Invacare, Inc.; Mountain Medical Equipment, Inc.; Pari Respiratory, Inc.; Mada Medical, Inc.; Puritan-Bennet; Schuco, Inc., DeVilbiss Health Care, Inc.; and Hospitak, Inc. Ultrasonic nebulizers generally rely on mechanical energy in the form of vibration of a piezoelectric crystal to generate respirable liquid droplets and are commercially available from, for example, Omron Healthcare, Inc. and DeVilbiss Health Care, Inc. Vibrating mesh nebulizers rely upon either piezoelectric or mechanical pulses to generate respirable liquid droplets. Commercial examples of nebulizers that could be used in certain embodiments include RESPIRGARD II®, AERONEB®, AERONEB® PRO, and AERONEB® GO produced by Aerogen; AERX® and AERX ESSENCE™ produced by Aradigm; PORTA-NEB®, FREEWAY FREEDOM™, Sidestream, Ventstream and I-neb produced by Respironics, Inc.; and PARI LC-PLUS®, PARI LC-STAR®, and e-Flow7m produced by PARI, GmbH. By further non-limiting example, U.S. Pat. No. 6,196,219, is hereby incorporated by reference in its entirety.

In some embodiments, the drug solution can be formed prior to use of the nebulizer by a patient. In other embodiments, the drug can be stored in the nebulizer in solid form. In this case, the solution can be mixed upon activation of the nebulizer, such as described in U.S. Pat. No. 6,427,682 and PCT Publication No. WO 03/035030, both of which are hereby incorporated by reference in their entirety. In these nebulizers, the drug, optionally combined with excipients to form a solid composition, can be stored in a separate compartment from a liquid solvent.

Dosages and Products

Certain embodiments provide pharmaceutical compositions suitable for use in the technology, which include compositions where the active ingredients are contained in an amount effective to achieve its intended purpose. A "therapeutically effective amount" means an amount sufficient to prevent, treat, reduce the severity of, delay the onset of or inhibit a symptom of an *A. baumannii* infection. The symptom can be a symptom already occurring or expected to occur. Determination of a therapeutically effective amount is well within the capability of those skilled in the art, especially in light of the detailed disclosure provided herein.

The term "an amount sufficient" as used herein refers to the amount or quantity of an active agent (e.g., an antibody binding agent, anti-bacterial medication, and/or a combination of these active agents) present in a pharmaceutical composition that is determined high enough to prevent, treat, reduce the severity of, delay the onset of, or inhibit a symptom of an *A. baumannii* infection and low enough to minimize unwanted adverse reactions. The exact amount of active agents or combination of active agents required will vary from subject to subject, depending on age, general condition of the subject, the severity of the condition being treated, and the particular combination of drugs administered. Thus, it is not always possible to specify an exact universal amount sufficient to prevent or treat an *A. baumannii* infection for a diverse group of subjects. As is well known, the specific dosage for a given patient under specific conditions and for a specific disease will routinely vary, but determination of the optimum amount in each case can readily be accomplished by simple routine procedures. Thus, an appropriate "an amount sufficient" to prevent or treat an *A. baumannii* infection in any individual case may be determined by one of ordinary skill in the art using routine experimentation.

In other embodiments, a therapeutically effective amount can describe the amount necessary for a significant quantity of the composition to contact the desired region or tissue where prevention or treatment of an *A. baumannii* infection is desired.

The antibody binding agents and compositions comprising antibody binding agents as described herein can be administered at a suitable dose, e.g., at a suitable volume and concentration depending on the route of administration. Within certain embodiments of the invention, dosages of administered antibody binding agents can be from 0.01 mg/kg (e.g., per kg body weight of a subject) to 500 mg/kg, 0.1 mg/kg to 500 mg/kg, 0.1 mg/kg to 400 mg/kg, 0.1 mg/kg to 300 mg/kg, 0.1 mg/kg to 200 mg/kg, 0.1 mg/kg to 150 mg/kg, 0.1 mg/kg to 100 mg/kg, 0.1 mg/kg to 75 mg/kg, 0.1 mg/kg to 50 mg/kg, 0.1 mg/kg to 25 mg/kg, 0.1 mg/kg to 10 mg/kg, 0.1 mg/kg to 5 mg/kg or 0.1 mg/kg to 1 mg/kg. In some aspects the amount of an antibody binding agent can be about 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.9 mg/kg, 0.8 mg/kg, 0.7 mg/kg, 0.6 mg/kg, 0.5 mg/kg, 0.4 mg/kg, 0.3 mg/kg, 0.2 mg/kg, or 0.1 mg/kg. In some embodiments a therapeutically effective amount of an antibody binding agent is between about 0.1 mg/kg to 500 mg/kg, or between about 1 mg/kg and about 300 mg/kg. Volumes suitable for intravenous administration are well known.

In some embodiments an antibody binding agent or a pharmaceutical composition comprising an antibody binding agent that is formulated for topical or external delivery can include higher amounts of an antibody binding agent. For example pharmaceutical composition comprising an antibody binding agent that is formulated for topical administration may comprise at least 0.1 mg/ml, at least 1 mg/ml, at least 10 mg/ml, at least 100 mg/ml or at least 500 mg/ml of an antibody binding agent.

The compositions can, if desired, be presented in a pack or dispenser device, which can contain one or more unit dosage forms containing the active ingredient. The pack can for example comprise metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions comprising a compound of the invention formulated in a compatible pharmaceutical carrier can also be prepared, placed in an appropriate container, and labeled for treatment of an indicated condition.

Distinguishable Identifiers

In some embodiments an antibody binding agent comprises one or more distinguishable identifiers. Any suitable distinguishable identifier and/or detectable identifier can be used for a composition or method described herein. In certain embodiments a distinguishable identifier can be directly or indirectly associated with (e.g., bound to) an antibody binding agent. For example a distinguishable identifier can be covalently or non-covalently bound to an antibody binding agent. In some embodiments a distinguishable identifier is bound to or associated with an antibody binding agent and/or a member of binding pair that is covalently or non-covalently bound to an antibody binding agent. In some embodiments a distinguishable identifier is reversibly associated with an antibody binding agent. In certain embodiments a distinguishable identifier that is reversibly associated with an antibody binding agent can be removed from an antibody binding agent using a suitable method (e.g., by increasing salt concentration, denaturing, washing, adding a suitable solvent and/or salt, adding a suitable competitor, and/or by heating).

In some embodiments a distinguishable identifier is a label. In some embodiments an antibody binding agent comprises a detectable label, non-limiting examples of which include a radiolabel (e.g., an isotope), a metallic label, a fluorescent label, a chromophore, a chemiluminescent label, an electrochemiluminescent label (e.g., Origen™), a phosphorescent label, a quencher (e.g., a fluorophore quencher), a fluorescence resonance energy transfer (FRET) pair (e.g., donor and acceptor), a dye, a protein (e.g., an enzyme (e.g., alkaline phosphatase and horseradish peroxidase), an antibody, an antigen or part thereof, a linker, a member of a binding pair), an enzyme substrate, a small molecule (e.g., biotin, avidin), a mass tag, quantum dots, nanoparticles, the like or combinations thereof. Any suitable fluorophore or light emitting material can be used as a label. A light emitting label can be detected and/or quantitated by a variety of suitable techniques such as, for example, flow cytometry, gel electrophoresis, protein-chip analysis (e.g., any chip methodology), microarray, mass spectrometry, cytofluorimetric analysis, fluorescence microscopy, confocal laser scanning microscopy, laser scanning cytometry, the like and combinations thereof.

Binding Pairs

In some embodiments a composition or method described herein comprises one or more binding pairs. In certain embodiments one or more members of binding pair comprises an antibody binding agent. In some embodiments a binding pair comprises at least two members (e.g., molecules) that bind non-covalently to (e.g., associate with) each other. Members of a binding pair often bind specifically to each other. Members of a binding pair often bind reversibly to each other, for example where the association of two members of a binding pair can be dissociated by a suitable method. Any suitable binding pair, or members thereof, can be utilized for a composition or method described herein. Non-limiting examples of a binding pair includes antibody/antigen, antibody/antibody, antibody/antibody fragment, antibody/antibody receptor, antibody/protein A or protein G, hapten/anti-hapten, sulfhydryl/maleimide, sulfhydryl/haloacetyl derivative, amine/isotriocyanate, amine/succinimidyl ester, amine/sulfonyl halides, biotin/avidin, biotin/streptavidin, folic acid/folate binding protein, receptor/ligand, vitamin B12/intrinsic factor, analogues thereof, derivatives thereof, binding portions thereof, the like or combinations thereof. Non-limiting examples of a binding pair member include an antibody, antibody fragment, reduced antibody, chemically modified antibody, antibody receptor, an antigen, hapten, anti-hapten, a peptide, protein, nucleic acid (e.g., double-stranded DNA (dsDNA), single-stranded DNA (ssDNA), or RNA), a nucleotide, a nucleotide analog or derivative (e.g., bromodeoxyuridine (BrdU)), an alkyl moiety (e.g., methyl moiety on methylated DNA or methylated histone), an alkanoyl moiety (e.g., an acetyl group of an acetylated protein (e.g., an acetylated histone)), an alkanoic acid or alkanoate moiety (e.g., a fatty acid), a glyceryl moiety (e.g., a lipid), a phosphoryl moiety, a glycosyl moiety, a ubiquitin moiety, lectin, aptamer, receptor, ligand, metal ion, avidin, neutravidin, biotin, B12, intrinsic factor, analogues thereof, derivatives thereof, binding portions thereof, the like or combinations thereof. In some embodiments, a member of a binding pair comprises a distinguishable identifier.

Detecting *A. baumannii*

In some embodiments, compositions described herein (e.g., compositions comprising a mAb that binds *A. baumannii*) are used detect and/or diagnose an *A. baumannii* infection. In some embodiments, provided herein, is a method of diagnosis of an *A. baumannii* infection in a subject. In some embodiments, presented herein, is a method of detecting *A. baumannii* in a sample or subject. A method of detecting *A. baumannii* in a subject or sample often comprises determined the presence, absence or an amount of *A. baumannii* in a sample obtained from a subject. In certain embodiments, detecting and/or determining the presence of *A. baumannii* in a sample obtained from a subject indicates the subject has an *A. baumannii* infection. In certain embodiments, determining the absence of *A. baumannii* in a sample obtained from a subject indicates a subject does not have an *A. baumannii* infection. In some embodiments, a method of detecting *A. baumannii* in a subject comprises monitoring an *A. baumannii* infection in a subject, often to determine if a patient having an *A. baumannii* infection is responding to, or not responding to, an anti-bacterial treatment (e.g., an antibody binding agent and/or an antibacterial medication or treatment). Thus in certain embodiments is a method of diagnosing an *A. baumannii* infection in a subject, which method comprises measuring the level of *A. baumannii* in a sample obtained from said subject.

In some aspects, a method of detecting *A. baumannii* in a sample comprises obtaining a sample from a subject suspected of having an *A. baumannii* infection. In some embodiments, a sample is suspected of comprising *A. baumannii*, or a portion thereof. Often a sample suspected of comprising *A. baumannii*, or a portion thereof, is obtained from a subject at risk of having, or suspected of having, an *A. baumannii* infection. In some aspects, a method of detecting *A. baumannii* in a sample comprises contacting a sample with a antibody binding agent described herein, for example, an antibody binding agent that specifically binds to *A. baumannii*. In certain embodiments, an antibody binding agent that specifically binds to *A. baumannii* can specifically bind the cell surface of *A. baumannii* or to a polypeptide, carbohydrate, lipid or complex thereof that is exposed on the cell surface of *A. baumannii*. An antibody binding agent that specifically binds to *A. baumannii* can often form a bound complex with *A. baumannii*, or with a portion thereof, which complex can be detected in vitro or ex vivo by a suitable method, non-limiting examples of which include ELISA, immunoblotting, flow cytometry, gel electrophoresis, protein-chip analysis (e.g., any suitable chip methodology), microarray, mass spectrometry, cytofluorimetric analysis, fluorescence microscopy, confocal laser scanning microscopy, laser scanning cytometry, the like and combinations thereof.

A method of detecting a bound complex comprising an antibody binding agent and *A. baumannii*, or a portion thereof, can be a direct and indirect detection method. Direct detection methods often comprise detection of a distinguishable identifier that is covalently bound directly to an antibody binding agent (e.g., a primary antibody binding agent that binds directly to *A. baumannii* or a portion thereof). In certain embodiments, indirect methods of detection comprise detecting a distinguishable identifier that is indirectly bound (e.g., non covalently bound) or indirectly associated with a primary antibody binding agent (e.g., a primary antibody binding agent that binds directly to *A. baumannii* or a portion thereof). Any suitable method can be used to detect and/or quantitate the presence, absence and/or amount of an antibody binding agent specifically bound to *A. baumannii*, or a portion thereof, non-limiting examples of which can be found in Immunology, Werner Luttmann; Academic Press, 2006 and/or Medical Detection and Quantification of Antibodies to Biopharmaceuticals: Practical and Applied Considerations, Michael G. Tovey; John Wiley & Sons, Jul. 12, 2011, which are incorporated by reference herein in their entirety. Additional non-limiting examples of methods that can be used to detect and/or quantitate the presence, absence and/or amount of an antibody binding agent specifically bound to *A. baumannii*, or a portion thereof include use of a competitive immunoassay, a non-competitive immuno assay, western blots, a radioimmunoassay, an ELISA (enzyme (inked immunosorbent assay), a competition or sandwich ELISA, a sandwich immunoassay, an immunoprecipitation assay, an immunoradiometric assay, a fluorescent immunoassay, a protein A immunoassay, a precipitin reaction, a gel diffusion precipitin reaction, an immunodiffusion assay, an agglutination assay, a complement fixation assay, an immunohistochemical assay, a Western blot assay, an immunohistological assay, an immunocytochemical assay, a dot blot assay, a fluorescence polarization assay, a scintillation proximity assay, a homogeneous time resolved fluorescence assay, a IAsys analysis, a BIAcore analysis, the like or a combination thereof.

In certain embodiments, a determination of the presence or absence of *A. baumannii*, or an *A. baumannii* infection in a subject or sample, can be determined by comparing the levels of *A. baumannii* present in a subject sample with control samples comprising a known amount of *A. baumannii*, or portions thereof. In certain embodiments, a control sample may not contain *A. baumannii*, or a portion thereof. In some embodiments, a median level of *A. baumannii* detected in a group of control samples (for example, samples from healthy individuals) is used to set a zero standard (e.g., a level of detection that indicated the absence of *A. baumannii*. In certain embodiments, sample containing known amounts of *A. baumannii*, or portions thereof, are used to generate a standard curve from which the presence, absence or amount of *A. baumannii* is a test sample is determined. In certain embodiments, a kit (e.g., a diagnostic kit) is provided herein that comprises one or more control samples or samples that can be used to generate a standard curve. In some embodiments the determination of the incidence of *A. baumannii* infection may comprise deriving a likelihood ratio using a multivariate analysis based on distribution parameters from a set of reference data derived from analysis of the levels of *A. baumannii* in subjects in which *A. baumannii* infection is absent, present or in remission.

Thus provided herein, in certain embodiments, is diagnostic methods capable of measuring levels of *A. baumannii* and/or comparing said levels to known levels that are indicative of the disease state in a subject.

Kits

In some embodiments the antibody binding agents, compositions, formulations, combination products and materials described herein can be included as part of kits, which kits can include one or more of pharmaceutical compositions, antibody binding agents, and formulations of the same, combination drugs and products and other materials described herein. In certain embodiments a kit is a diagnostic kit comprising one or more antibody binding agents described herein. In some embodiments the products, compositions, kits, formulations, etc. can come in an amount, package, product format with enough medication to treat a patient for 1 day to 1 year, 1 day to 180 days, 1 day to 120 days, 1 day to 90 days, 1 day to 60 days, 1 day to 30 days, or any day or number of days there between, 1-4 hours, 1-12 hours, or 1-24 hours.

The invention provides kits including pharmaceutical compositions of the invention, combination compositions and pharmaceutical formulations thereof, packaged into suitable packaging material. A kit optionally includes a label or packaging insert including a description of the components or instructions for use in vitro, in vivo, or ex vivo, of the components therein. Exemplary instructions include instructions for a diagnostic method, treatment protocol or therapeutic regimen.

A kit can contain a collection of such components, e.g., two or more conjugates alone, or in combination with another therapeutically useful composition (e.g., an antiproliferative or immune-enhancing drug). The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics (PK) and pharmacodynamics (PD). Labels or inserts can include information identifying manufacturer information, lot numbers, manufacturer location and date.

Labels or inserts can include information on a condition, disorder, disease or symptom for which a kit component may be used. Labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. Kits of the invention therefore can additionally include labels or instructions for practicing any of the methods and uses of the invention described herein.

Labels or inserts can include information on any benefit that a component may provide, such as a prophylactic or therapeutic benefit. Labels or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Kits can additionally include other components. Each component of the kit can be enclosed within an individual container and all of the various containers can be within a single package. Invention kits can be designed for cold storage. Invention kits can further be designed to contain host cells expressing antibody binding agents, or that contain nucleic acids encoding antibody binding agents. The cells in the kit can be maintained under appropriate storage conditions until the cells are ready to be used. For example, a kit including one or more cells can contain appropriate cell storage medium so that the cells can be thawed and grown.

Such diagnostic methods and kits can take any suitable form. For example, a kit can comprise or consist of a stick test, including necessary reagents to perform the method of the invention and to produce, for example, a colorimetric result which can be compared against a color chart or standard curve. Such kits can also comprise, e.g., a buffering agent, a preservative, or a protein stabilizing agent. The kit can also comprise components necessary for detecting an antibody binding agent (e.g., an antibody that specifically binds a primary antibody binding agent, a distinguishable identifier, enzyme and/or substrate). A kit can also contain a control sample and/or a series of control samples (e.g., controls containing known amounts of *A. baumannii*, e.g., a standard curve) which can be assayed and compared to the test sample contained. In some embodiments, each component of the kit is usually enclosed within an individual container, and all of the various containers are within a single package, along with instructions for determining whether the subject from which the sample is derived is suffering from or is at risk of developing an *A. baumannii* infection.

EXAMPLES

Example 1—Antibody Generation

To induce an antibody response against target *Acinetobacter* and/or *Acinetobacter* surface proteins, male Balb/c mice (The Jackson Laboratory) were immunized with whole, live bacteria (*A. baumannii*, strain HUMC1, a virulent isolate of *A. baumannii*) and/or a fusion protein DHFR-3Loop which comprises portions of the outer membrane protein A (OmpA) of *A. baumannii*. The DHFR-3Loop fusion protein consists of the amino acid sequence of SEQ ID NO:1 as shown below.

```
                                        SEQ ID NO: 1
MVRPLNSIVAVSQNMGIGKNGDLPWPPLRNEFKYFQRMTTTSSVEGK

QNLVIMGRKTWFSIPEKNRPLKDRINIVLSRELKEPPRGAHFLAKSL

DDALRLIEQPELASKVDMVWIVGGSSVYQEAMNQPGHLRLFVTRIMQ
```

-continued
```
EFESDTFFPEIDLGKYKLLPEYPGVLSEVQEEKGIKYKFEVYEKKGG

GGSDSQHNNGGKDGNLTNGPELQDDLGGGGSVKGDVDGASAGAEYKQ

KQINGNGGGSRATYNADEEFWNYTAGHHHHHH
```

The DHFR-3Loop fusion protein includes an N-terminal portion having the amino acid sequence of mouse DHFR (dihydrofolate reductase, aa. 1-186) followed by three loop portions of OmpA (underlined). The loop portions are separated by GGGGS linkers. The C-terminal end of the fusion protein contains a His-tag for protein purification. The DHFR protein is not immunogenic itself, and allowed the bacterial sequences (which form structural loops in the endogenous OmpA protein) to be stably expressed for immunization. Recombinant DHFR-3Loop protein was expressed in *E. coli* and purified via a 6× His-tag (using a Ni-NTA Purification System, Invitrogen).

For generation of the 9.1C8 and R2D2 monoclonal antibodies, mice were injected on day 1 subcutaneously on the dorsal neck with 163 μg recombinant DHFR-3 Loop protein in complete Freund's adjuvant (CFA); on day 35 intravenously (i.v.) with $2.5 \times 10^6$ colony forming units (CFU) of live HUMC1 bacteria; on day 37 subcutaneously on the dorsal neck with 63 μg of DHFR-3 Loop protein in incomplete Freund's adjuvant (IFA); and on days 49 and 62, i.v. with $2.5 \times 10^6$ CFU of live HUMC1 bacteria. Three to four days before harvesting of spleens for hybridoma fusion (day 66), mice were injected subcutaneously on the on the base of the tail with 56 μg anti-mouse CD40 monoclonal antibody (low-endotoxin, azide-free anti-mouse CD40, BioLegend, #102908) to increase the number of antigen-specific B cells available for fusion (Rycyzyn M. A., et al., Hybridoma (2008) 27:1, pages 25-30).

Hybridoma fusion was performed according to the method described in Current Protocols in Immunology (2006, Wiley & Sons press). Briefly, spleens of immunized animals were harvested 3-4 days following anti-CD40 injection. Vigorously growing SP2/0-Ag14 myeloma cells (ATCC) were combined with a single-cell suspension of splenocytes following red blood cell lysis at a 1:5 ratio in complete serum-free DMEM. Cell mixtures were pelleted, then gently mixed with 1 ml of sterile, pre-warmed 50% polyethylene glycol in DMEM. An additional 9 ml of complete serum-free DMEM was slowly added to avoid breaking up cell clusters, the tube was centrifuged at 500×g for 5 min, and the pellet resuspended in 10 ml of complete DMEM containing 20% FBS (DMEM-20). Two drops of cell mixture were added to each well of a 96-well flat-bottom plate until the entire suspension was plated. On day 1, two drops of complete DMEM-20 containing hypoxanthine-aminopterin-thymidine (HAT medium) was added to each well as selection medium. Cells were continuously fed with fresh HAT medium for two weeks, before switching to DMEM-20 containing HT only, for two days. Subsequently, cells were maintained in complete DMEM-20 (without HT), and wells were monitored for growth prior to screening.

Hybridoma pre-clones were selected for subcloning based on bacterial cell surface reactivity by flow cytometry. Briefly, *A. baumannii* was passaged to log phase, stained with the bacterial dye SYTO BC (LifeTech #B7277), then stained with pre-clone supernatant from 96-well plates at 4° C., rinsed, and counter-stained with CF 647-conjugated goat anti-mouse IgG (Sigma-Aldrich, #SAB4600182). Control samples were stained with mouse IgG1 isotype control mAb (R&D Systems, #MAB002). Percent positivity was determined by flow cytometry.

Example 2—Antibody Analysis

Monoclonal antibodies (mAb) were isolated and/or purified from clonal hybridoma cell lines showing specific binding reactivity to *A. baumannii* cell surface by flow cytometry. Despite the fact that mice were immunized with the recombinant DHFR-3Loop protein, the monoclonal antibodies described herein did not appear to specifically bind to any of the loops of OmpA, or to OmpA itself (from ELISA data, not shown, using DHFR-3Loop or whole OmpA as the targets).

9.1C8 mAb

A first monoclonal antibody that specifically binds to the cell surface of *A. baumannii* was generated and isolated as described above. The clonal hybridoma cell line was provided the name 9.1C8, which hybridoma produces the 9.1C8 monoclonal antibody (9.1C8, further abbreviated C8). The 9.1C8 hybridoma was deposited with the ATCC Patent Depository, located at 10801 University Blvd., Manassas, Va. 20110, U.S.A. on May 27, 2015 (ATTC accession number: PTA-122177). The C8 monoclonal antibody was determined to be an IgG1 isotype. The C8 monoclonal antibody, as well as polyclonal immune serum, specifically bound to the cell surface of *A. baumannii* as determined by flow cytometry (FIG. 1).

Figure 2:
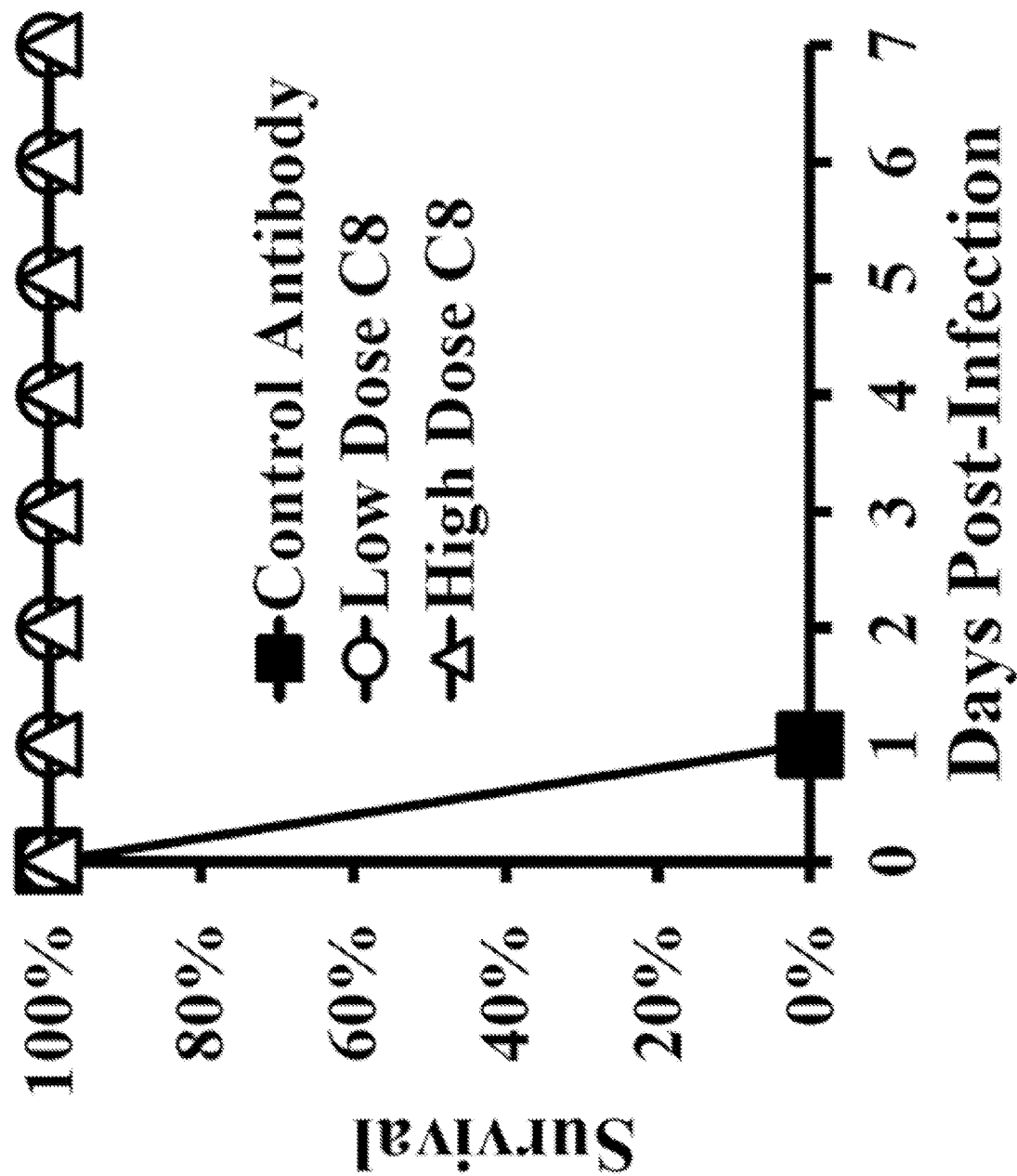
FIG. 2. shows a survival plot of mice infected with *A. baumannii* and treated with control antibody (20 µg, filled squares), low dose C8 monoclonal (10 µg, open circles) or high dose C8 monoclonal (20 µg, open triangle). N=10 mice per group.
Figure 3:
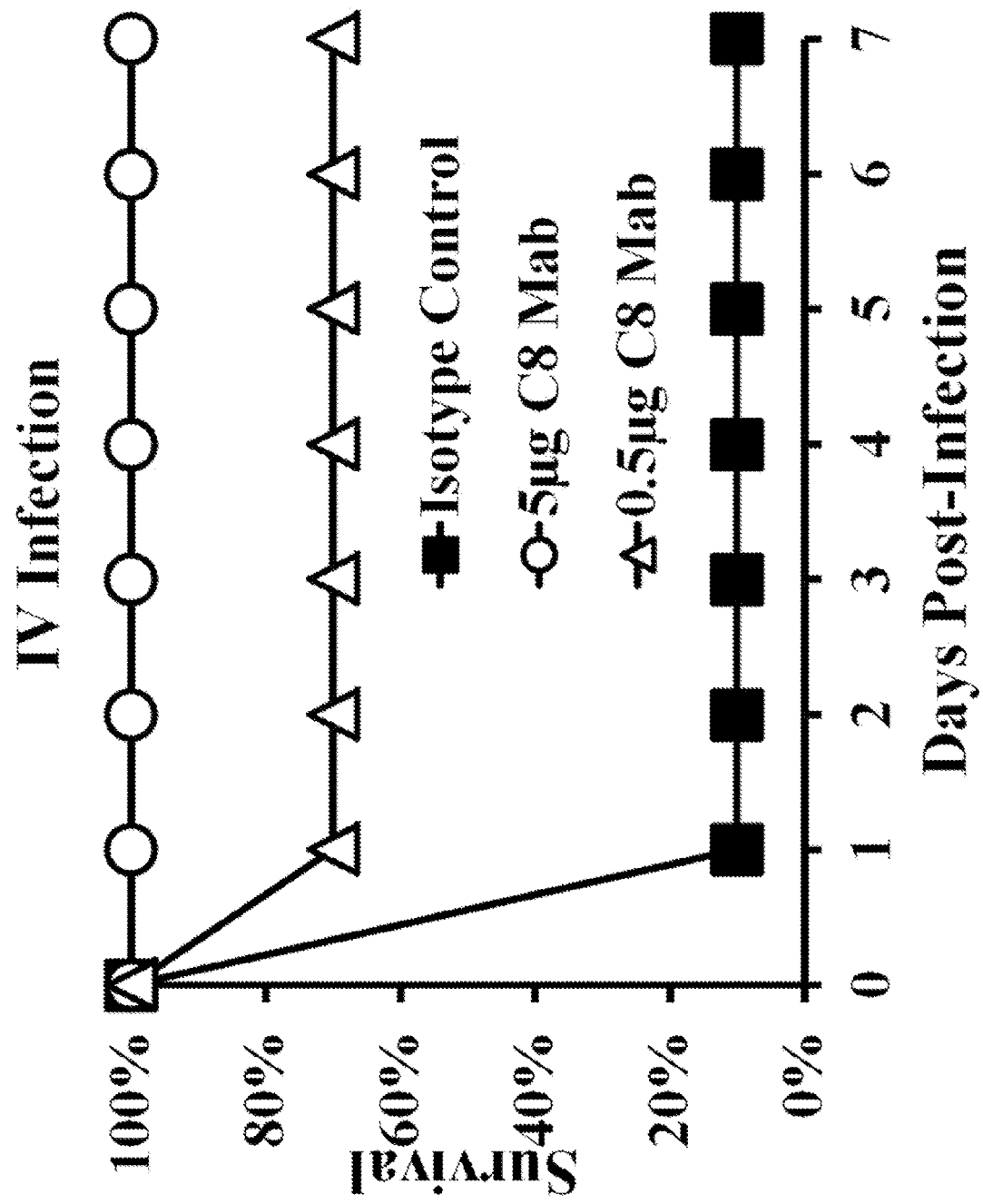
FIG. 3 shows a survival plot of mice infected by i.v. injection with *A. baumannii* and treated with control antibody (filled) squares, low dose (5 µg) C8 monoclonal (open circles) or very low dose (0.5 µg) C8 monoclonal antibody (open triangle). N=10 mice per group.
Figure 4:
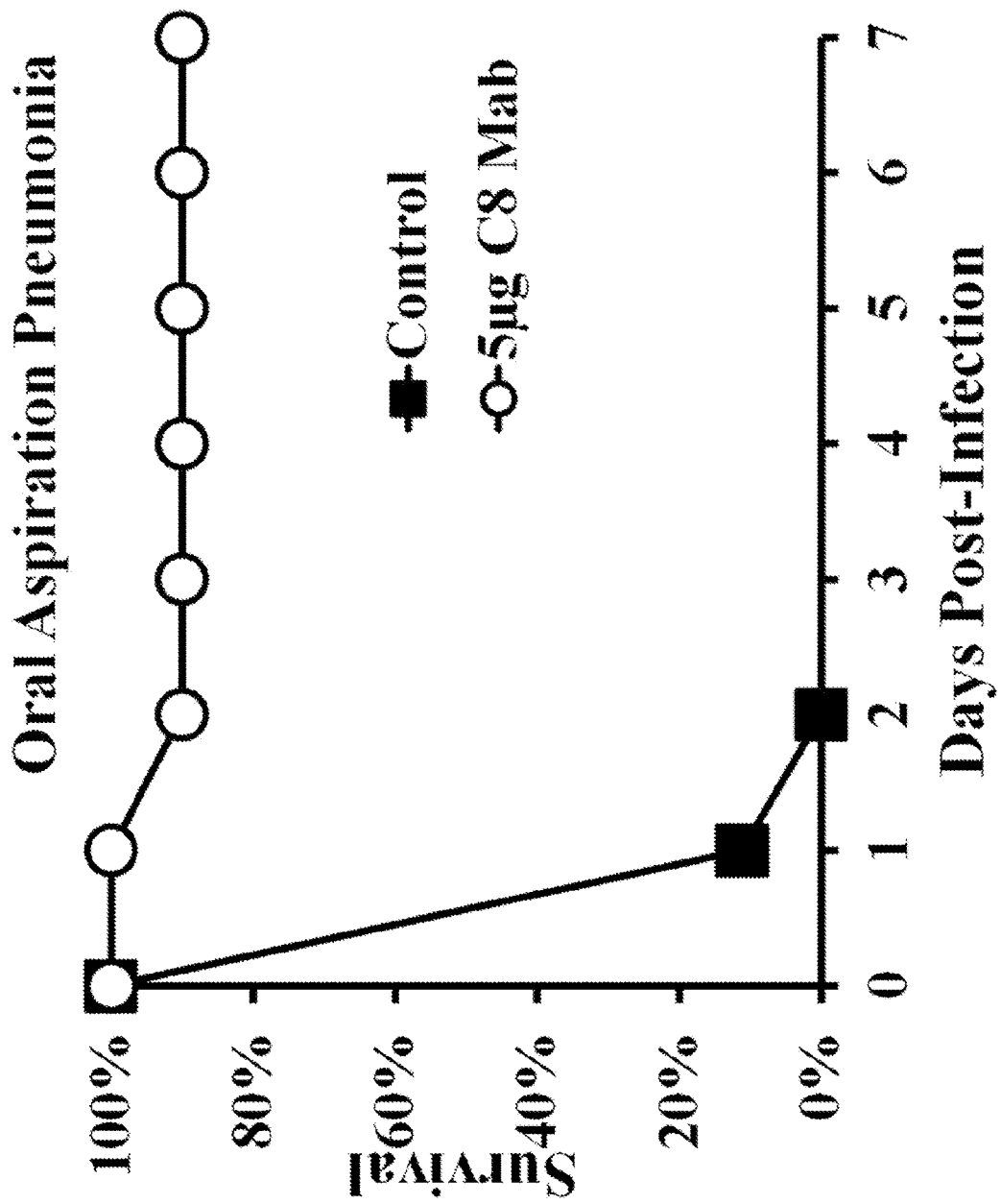
FIG. 4 shows survival plot of mice infected in the lung by oral aspiration with *A. baumannii* and treated with control antibody (filled squares) or 5 µg of C8 monoclonal antibody (open circles). N=9 control mice and 10 treated mice.

To determine if C8 could treat, inhibit and/or prevent *A. baumannii* induced sepsis, mice were infected i.v. via the tail-vein with $2\times10^7$ hyper-virulent *A. baumannii* HUMC1 and were treated once i.v. with either protein-G purified C8 mAb (approximately 10 or 20 µg doses) or an isotype-control antibody in a saline buffer. The C8 mAb was 100% protective against infection at both doses (10 µg & 20 µg) (FIG. 2). In a second experiment, mice were similarly infected and the C8 MAb was administered once i.v. in saline buffer at a low (5 µg) and very low (0.5 µg) dose. Again the C8 mAb markedly improved survival (FIG. 3). In a fourth experiment, mice were infected by oropharyngeal aspiration pneumonia with $10^8$ *A. baumannii* HUMC1 and treated i.v. with 5 µg of C8 mAb, and again survival was markedly improved (FIG. 4). Therefore, as demonstrated herein, C8 bound to the cell surface of *A. baumannii* and protected mice from death using lethal models of *A. baumannii* blood-stream and lung infection.

The amino acid sequence of the variable regions of the C8 monoclonal antibody were determined. The variable region of the light chain of the C8 monoclonal antibody comprises the amino acid sequence of SEQ ID NO:2 as shown below.

SEQ ID NO: 2
LPLSLPVSLGDQASISCRSSQSIVHNNGNTYLEWYLQKPGQSPKLLI

YKVSNRFSGVPDRFSGSGSGTDFTLKISRVEAEDLGVYYCFQGSHVP

LTFGAGTKLEIKGSRS

The variable region of the heavy chain of the C8 monoclonal antibody comprises the amino acid sequence of SEQ ID NO:3 as shown below. To determine if C8 could treat, inhibit and/or prevent *A. baumannii* induced sepsis, mice were infected i.v. via the tail-vein with $2\times10^7$ hyper-virulent *A. baumannii* HUMC1 and were treated once i.v. with either protein-G purified C8 mAb (approximately 10 or 20 µg doses) or an isotype-control antibody in a saline buffer. The C8 mAb was 100% protective against infection at both doses (10 µg & 20 µg) (FIG. 2).

SEQ ID NO: 3
EVQLQQSGPELVKPGASVKISCKASGYSFTGYTMNWVKQSHGKSLEW

IGRINPYNGDSFYNQKFKGKATLTVDKSSNIAHMEFLSLTSEDSAVY

YCGRSGDGPWFAYWGQGTLVTVSA

R2D2 mAb

A second monoclonal antibody that specifically binds to the cell surface of *A. baumannii* was generated and isolated as described above. The clonal hybridoma cell line was provided the name R2D2, which hybridoma produces the R2D2 monoclonal antibody. The R2D2 hybridoma was deposited with the ATCC Patent Depository, located at 10801 University Blvd., Manassas, Va. 20110, U.S.A. on May 27, 2015 (ATTC accession number: PTA-122178). The R2D2 monoclonal antibody was determined to be an IgM isotype. The R2D2 monoclonal antibody, as well as polyclonal immune serum, specifically bound to the cell surface of *A. baumannii* as determined by flow cytometry (data not shown).

The amino acid sequence of the variable regions of the R2D2 monoclonal antibody were determined. A variable region of the light chain of the R2D2 monoclonal antibody comprises the amino acid sequence of SEQ ID NO:28 as shown below.

SEQ ID NO: 28
DIGMTQSXSPQDMSVGPKVTMSSKCRKSLLNSRNQKKYLTSDQQKPG

QYTKSLGDFASISESRVTDRFIGSGSGTDLPLGWGILPPLPLADYFC

QQHYSTP

A variable region of the heavy chain of the R2D2 monoclonal antibody comprises the amino acid sequence of SEQ ID NO:29 as shown below.

SEQ ID NO: 29
QVQLKQSGPGLVQPSQSLSITCTVSGFSLTSYGVHWVRQSPGKGLEW

LGVIWSGGSTDYNAAFISRLSISKDNSKSQVFFKMNSLQANDTAIYY

CARRRRSTAMDYWGQGTSVTVSSESQSFPN

The R2D2 monoclonal antibody specifically bound to the cell surface of *A. baumannii* as determined by flow cytometry (data not shown). To determine if R2D2 could treat, inhibit and/or prevent *A. baumannii* induced sepsis, mice were infected i.v. via the tail-vein with $2\times10^7$ hyper-virulent *A. baumannii* HUMC1 and were treated once i.v. with either protein-G purified R2D2 mAb (approximately 20 µg) or an isotype-control antibody in a saline buffer. The R2D2 mAb was protective against infection.

X1 mAb

Also provided herein is a third monoclonal antibody X1 (X1 mAb). The X1 mAb was generated by the same method used to generate the 9.1C8 mAb. The X1 mAb is determined to have the same or similar functional and therapeutic properties as the 9.1C8 mAb. The clonal hybridoma cell line was provided the name X1, which hybridoma produces the X1 monoclonal antibody. The X1 monoclonal antibody was determined to be an IgG1 isotype.

The amino acid sequence of the variable regions of the X1 monoclonal antibody were determined. The variable region of the light chain of the X1 monoclonal antibody comprises the amino acid sequence of SEQ ID NO:2 as shown below.

SEQ ID NO: 2
LPLSLPVSLGDQASISCRSSQSIVHNNGNTYLEWYLQKPGQSPKLLI

YKVSNRFSGVPDRFSGSGSGTDFTLKISRVEAEDLGVYYCFQGSHVP

LTFGAGTKLEIKGSRS

The variable region of the heavy chain of the X1 monoclonal antibody comprises the amino acid sequence of SEQ ID NO:67 as shown below.

SEQ ID NO: 67
GVFSEVQLQQSGPELVKPGASVKISCKASGYSFTGYFMNWVKQSHGK

SLEWIGRINPYNGDTFYNQKFKGKATLTVDKSSTAHMELRSLTSED

SAVYYCARLNYRGAYWGQGTLVTVSA

Example 3

*A. baumannii* virulence is driven by evasion of innate immune clearance, allowing high bacterial burdens to trigger LPS-TLR4-induced sepsis syndrome. Thus, strategies to enhance innate immune clearance should improve survival by ameliorating sepsis syndrome.

Immunotherapy against *A. baumannii* is predicted to enhance innate immune clearance. As disclosed herein, a monoclonal antibody (MAb)-based therapy was highly protective for bloodstream and lung infection. In vitro and in vivo antibacterial effects of the MAb and its mechanism of protection against *A. baumannii* infection are described herein. Also efficacy of a humanized MAb is also demonstrated. These results support the rapid translation of the MAb as an adjunctive therapy for XDR or pan-drug-resistant (PDR) *A. baumannii* infections.

Materials and Methods

Generation of Hybridomas

To induce an antibody response against target *Acinetobacter* surface proteins, mice were immunized with a sublethal inoculum ($10^6$) of *A. baumannii* HUMC1, a hypervirulent, XDR clinical blood and lung isolate, which was administered i.v. via the tail-vein. Mice were boosted two weeks and five weeks later. Two weeks following the last boost, and 4 days before harvesting of spleens for hybridoma fusion, mice were subcutaneously injected with 50 µg anti-mouse CD40 MAb (clone 5C3, BioLegend). Spleens from immunized animals were harvested 3 days following anti-CD40 injection. Vigorously growing SP2/0-Ag14 myeloma cells (ATCC) were combined with a single-cell suspension of splenocytes, and successful fusion events were selected by growing cells in DMEM media containing 20% fetal bovine serum and hypoxanthine-aminopterin-thymidine (HAT medium).

Hybridoma Screening

Hybridoma cell lines were propagated in 96-well flat-bottom plates in DMEM-20%, and supernatants were harvested from wells for initial flow cytometry screening to identify antibodies that bound to intact bacteria. In brief, *A. baumannii* isolates were passaged to log phase, stained with the bacterial dye SYTO BC (LifeTech #B7277), and incubated for 1 hr with undiluted supernatants collected from 96-well plates at 4° C. Cells were washed and counter-stained with a secondary antibody, CF647-conjugated goat anti-mouse IgG (Sigma-Aldrich, #SAB4600182). Control samples were stained with a mouse IgG1 isotype control MAb (R&D Systems, #MAB002) as a negative control, and mouse polyclonal HUMC1-immune serum as a positive control for bacterial binding. Hybridomas that tested positive for bacterial binding were subcloned by limiting dilution into 96-well plates to ensure clonality, expanded, and retested to confirm bacterial binding.

MAb Purification and Isotype Confirmation

Antibodies were purified from clonal hybridoma supernatants using Pierce Protein G agarose resin spin columns (ThermoFisher Scientific) according to the manufacturer's instructions. Antibodies were assessed for purity by running on a PAGE gel, and quantitated using a Pierce BCA Protein Assay Kit (Thermo Fisher Scientific). Isotype was determined by ELISA BD Pharmingen Mouse Immunoglobulin Isotyping ELISA Kit (Thermo Fisher Scientific).

Bacterial Strains and Culture

*A. baumannii* strains (Table 7) were grown overnight at 37° C. with shaking in TSB broth. Bacteria were subcultured and passaged to mid-log-growth at 37° C. with shaking, then pelleted and washed twice in PBS before measuring the $OD_{600}$ to estimate density. Bacteria were resuspended at the appropriate concentration for infection in 250 µL of PBS per mouse. Actual concentrations of bacterial inocula were confirmed by quantitative plating of dilutions of the inocula on agar plates.

Effects of Antibody on Colistin MIC

The minimum inhibitory concentration (MIC) of colistin for *A. baumannii* HUMC1 was determined in congruence with standard CLSI methodologies. In brief, *A. baumannii* HUMC1 was passaged in Mueller Hinton II (MH-II) Broth for 3 hr at 37° C. with shaking then diluting to $5 \times 10^5$ CFUs/mL. Colistin was serially diluted across rows of a 96-well plate with 0.1, 1, or 10 µg/mL C8 MAb, which was incubated at 37° C. for 24 hr. The MIC value was read as the lowest concentration that prevented visible growth of bacteria.

Immunofluorescence

To detect surface binding of *A. baumannii* by purified C8 MAb, mid-log-growth *A. baumannii* strains were washed twice, resuspended in PBS, stained with NucBlue Reagent (Life Technologies) for 30 min at 37° C., pelleted, and washed again in PBS. Primary antibody, either C8 MAb or Isotype Control IgG1 (R&D Systems, Product #MAB002), was added to 100 µL of bacteria to a final concentration of 100 µg/mL and incubated for 30 min at 37° C. Bacteria were washed twice and resuspended in secondary antibody goat anti-mouse IgG AlexaFluor647 (Life Technologies, Product #A21235) at a final concentration of 2 µg/mL for 20 min at 37° C. After washing twice with PBS, bacteria was resuspended in 50 µL PBS, and 10 µL drops were placed on slides and mounted with cover slips and nail polish. Images were taken using a Spinning Disc Confocal Microscope (Zeiss Axiolmager).

Immunofluorescent labeling of *A. baumannii* in slide-mounted lung tissue sections Lung sections were paraffin embedded on slides then baked at 60° C. overnight. Slides were rehydrated and incubated in antigen retrieval solution (Dako Target Retrieval Solution) then blocking buffer (0.1% BSA, 0.01% Triton-X, in PBS). The slides were stained overnight at 4° C. with *A. baumannii* immune serum diluted 1:500 in PBS. On the following day, slides were rinsed with PBS and stained for 45 minutes at room temperature with the secondary antibody (American Qualex Goat anti-mouse IgG H+L Fluorescein A106FZYP) diluted 1:40 in PBS. From this step forward, samples were protected from light. Slides were rinsed with PBS and mounted with anti-fade mounting media (Vectashield mounting medium for fluorescence with Dapi) and nail polish. Images were captured with a Perkin Elmer Spinning ADisc Confocal microscope and an Olympus BX61 fluorescent microscope.

Transmission Electron Microscopy

Mid-log-growth *A. baumannii* cultures were washed twice incubated with primary antibody (200 µg/mL) at room temperature for 30 min, washed three times in PBS, and resuspended in 50 µL PBS. Goat anti-mouse IgG 20 nm Gold Conjugated (TedPella Inc.) was added to each tube at a final concentration of 0.8 µg/mL and incubated at room temperature for 30 min. Bacteria were washed, pelleted, and resuspended in 500 µL of half-strength Karnovsky's Fixative (2% paraformaldehyde and 2.5% gluteraldehyde in 0.1M phosphate buffer) for 2 hours at room temperature. Following incubation, the pellet was dislodged from the bottom of the tube using a bent stick and allowed to sit in fixative overnight. After overnight fixation, fixative was carefully aspirated off and 1 mL of PBS was carefully added to the tube in order to prevent agitation of the pellet. The pellet was then post-fixed in 1% Osmium Tetroxide for 1 hour and stained with 1% Uranyl Acetate overnight. The pellet was then put in 15% BSA for 2 hours and subsequently subjected to another treatment with the half-strength Karnovsky's Fixative to harden. Pellets were washed in water, dehydrated, embedded in Epon, sectioned, and placed on copper grids. Electron Micrographs were taken on a JEOL JEM-2100 Microscope operating at 80 kV.

In Vitro Complement Susceptibility and Opsonophagocytosis Assays

Overnight cultures of *A. baumannii* were subcultured to log-phase, washed in PBS, and resuspended at $1 \times 10^6$ CFUs/mL in 3 mL HBSS containing 50% CD-1 mouse serum that had been either heat-inactivated at 57° C. for 30 minutes or not. Tubes were shaken (200 rpm) for 2 hr at 37° C. and bacterial expansion was quantified by serially diluting cultures on TSA plates and counting CFUs.

RAW 264.7 macrophages ($1 \times 10^6$ per well) were grown on coverslips in 12-well plates and stimulated with 100 U/mL IFN-γ. Cells adhered to the cover glass overnight in a humidified incubator at 37° C. supplemented with 5% $CO_2$. Cells were washed three times with HBSS and bacteria were added to wells at a ratio of 10:1, bacteria to macrophages, in the presence (or absence) of 10% fetal bovine serum (FBS), either heat-inactivated or complement-active. Plates were briefly centrifuged at 250×g to cohere the bacterial cells to the bottom of the plate and incubated at 37° for 2 hr. Macrophages were washed three times with PBS, fixed with 100% methanol, and Hema 3-stained according to the manufacturer's protocol (Fisher Scientific). To quantitate bacteria counts per macrophage, coverslips were imaged on a Zeiss AxioImager microscope. Macrophages harboring visible adherent or internalized bacteria were counted and divided by total macrophages to determine the percentage of cells with associated bacteria. The number of bacteria associated with each macrophage was also quantitated and recorded. A minimum of 100 cells per coverslip were counted.

Mouse Models of Infection

Male C3HeB/Fe mice (Jackson Labs) between the ages of 7-10 wk were used for all experiments. All animal work was conducted following approval by the Institutional Animal Use and Care Committee at the University of Southern California, in compliance with the recommendations in the Guide for the Care and Use of Laboratory Animals of the National Institutes of Health.

For the bloodstream infection model, mice were infected intravenously via the tail-vein with designated inocula of *A. baumannii* isolates. An oropharyngeal model of aspiration pneumonia that recapitulates hospital- or ventilator-associated pneumonia (VAP) relevant to ICU populations was used. In brief, mice were sedated with isoflurane, hung by their maxillary incisors, tongues held to prevent swallowing, and 50 µL of bacterial inocula was placed in the trachea to allow inoculation of the organisms into the lungs by reflexive aspiration.

To determine blood and tissue bacterial burden and cytokine levels, mice were sedated with ketamine and xylazine and blood was obtained by cardiac puncture. Mice were then euthanized and the organs were harvested and homogenized in sterile PBS. Homogenized organs from each mouse were quantitatively cultured to determine tissue bacterial burden. Sections of lungs were also fixed in zinc-buffered formalin, mounted in paraffin, thinly sectioned, and stained by H&E and immunofluorescence for histopathology.

Statistics

Survival was compared by the non-parametric Log Rank test. Surface staining and bacterial killing were compared with the Wilcoxon Rank Sum test for unpaired comparisons. All statistics were run using KyPlot. Differences were considered significant if the p value was <0.05.

Results

Generation and Characterization of a Monoclonal Antibody Recognizing *A. baumannii*

Figure 5A:
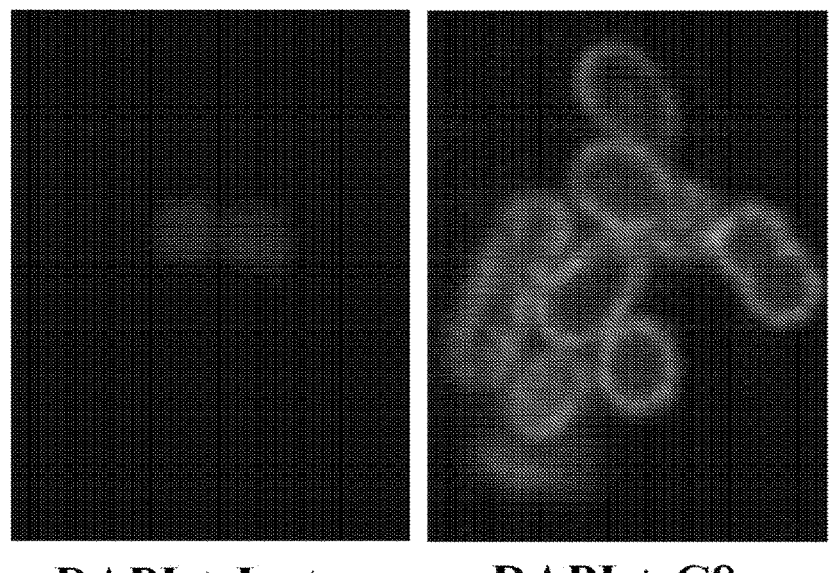
FIG. 5A shows confirmed diffuse surface binding of C8 MAb by confocal immunofluorescence microscopy (Alex488, green) to DAPI-(blue) stained *A. baumannii* HUMC1.
Figure 5B:
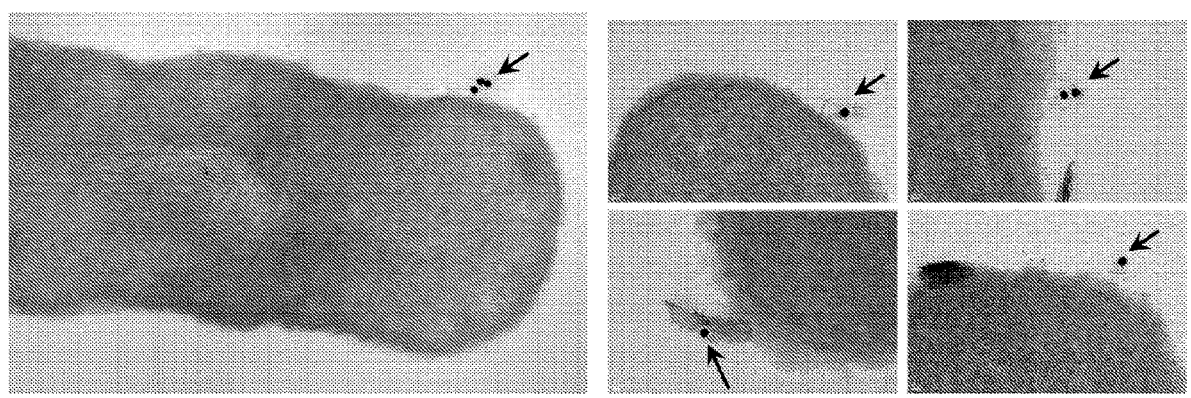
FIG. 5B shows immunogold electron microscopy (40,000× magnification) demonstrating C8 binding to the pili on *A. baumannii* HUMC1 (black arrows).
Figure 5C:
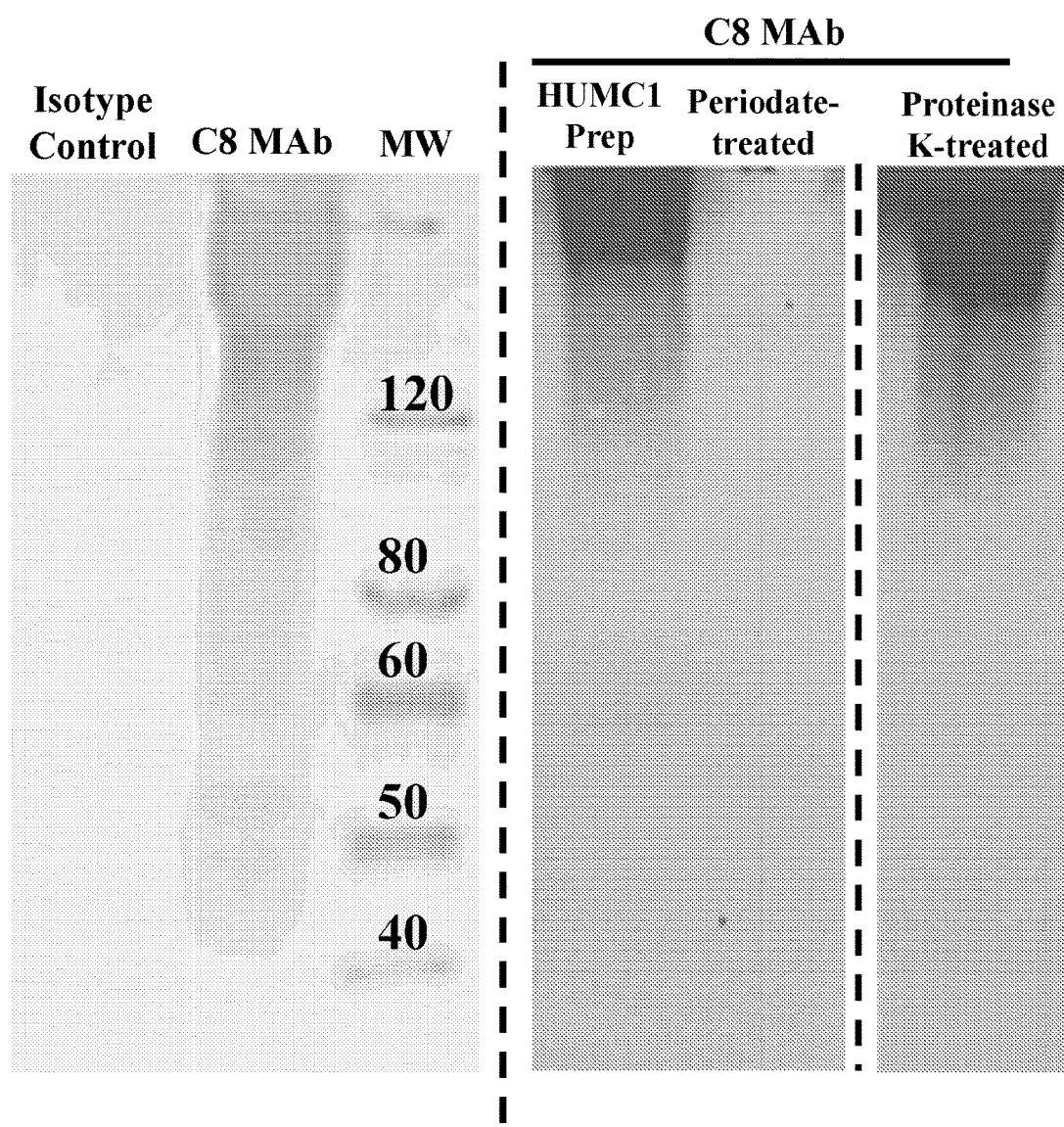
FIG. 5C shows Western blot of pili preparations from *A. baumannii*, including preparations treated with proteinase K or periodate to degrade protein or carbohydrates, respectively. The blots were stained with C8 MAb or isotype control.

Screening of hybridomas from immunized mice led to identification of a clone that secreted an IgG1-kappa monoclonal antibody (MAb), which was designated "C8". The C8 MAb bound to the surface of HUMC1, the hyper-virulent clinical blood and lung isolate of *A. baumannii* used to immunize the mouse, to the same extent as polyclonal immune serum (FIG. 1). Binding of C8 to the surface of HUMC1 was confirmed by immunofluorescent staining of the bacteria with the C8 MAb conjugated to AlexaFluor488 (FIG. 5B). Surface binding was confirmed to 4 other diverse clinical isolates as well by flow cytometry (Table 7). Finally, electron microscopy was used to determine the physical binding site of the MAb on the bacterial surface. The C8 MAb bound to the pili on the bacterial surface (FIG. 5C).

Since it appeared that C8 bound to the pili on the surface of the bacteria, an established protocol was to sheer pili off the bacteria in an attempt to more accurately determine the epitope targeted by C8. To distinguish protein from carbohydrate targets, the pili preparation was divided into three portions: one fraction was treated with proteinase K, one fraction was treated with periodate to degrade carbohydrates, and one fraction was untreated. The pili preparations were run in a western blot and stained with C8 or isotype control MAb. The western blot signal from the untreated fraction was a large conglomeration at the top of the gel (FIG. 5D). A western blot of the pili preparation after treatment with either proteinase K or periodate showed the signal was unchanged with proteinase K treatment but eliminated completely by periodate treatment, indicating a carbohydrate target (FIG. 5D). Western blots and flow binding to a capsule-mutant bacterial strain confirmed that C8 binds to capsular polysaccharide on *A. baumannii*.

MAb Opsonizes *A. baumannii* for Increased Macrophage Uptake In Vitro

The *A. baumannii* HUMC1 isolate is hyper-virulent due to its ability to evade innate-immune-effector-mediated clearance from the blood within the first hour of infection. We therefore sought to determine the in vitro impact of the C8 MAb on innate effector mechanisms that can target *A. baumannii*, including serum sensitivity and macrophage uptake of HUMC1. C8 alone had a minimal impact on bacterial growth in vitro, in the presence of either heat-inactivated (HI) or complement-active mouse serum (FIG.

Figure 6A:
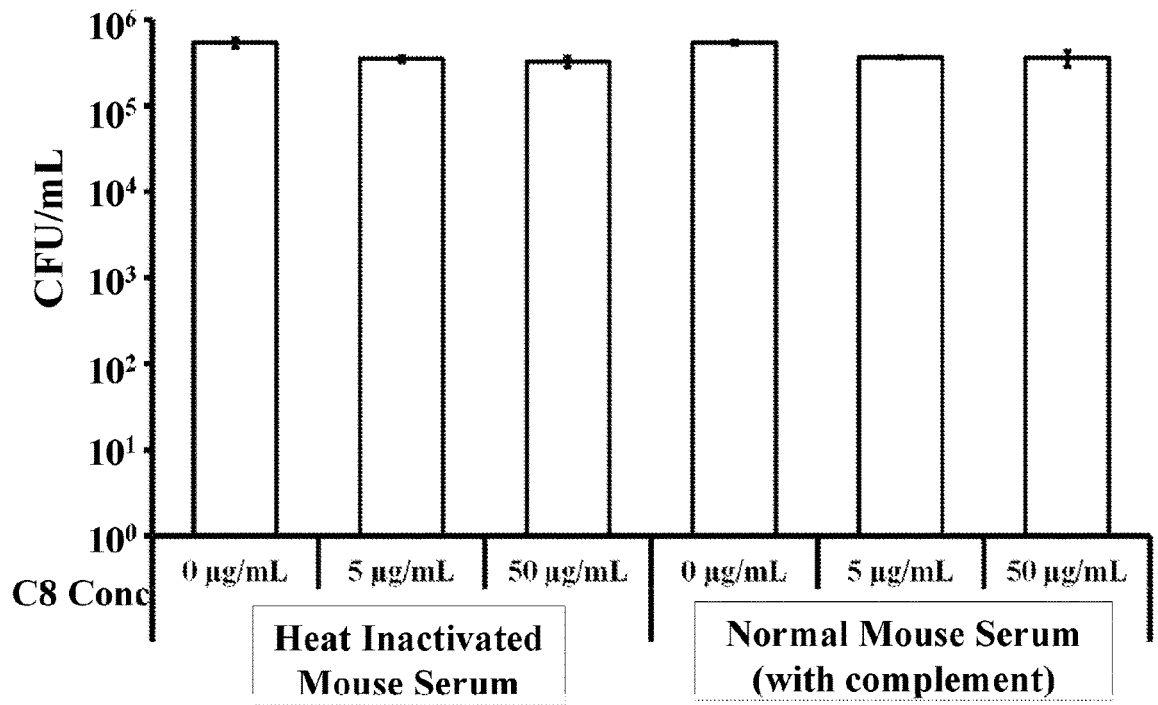
FIG. 6A demonstrates that the C8 MAb has minimal impact on in vitro growth of *A. baumannii* HUMC1 in the absence or presence of active complement (CD-1 mouse serum, heat inactivated or not).
Figure 6B:
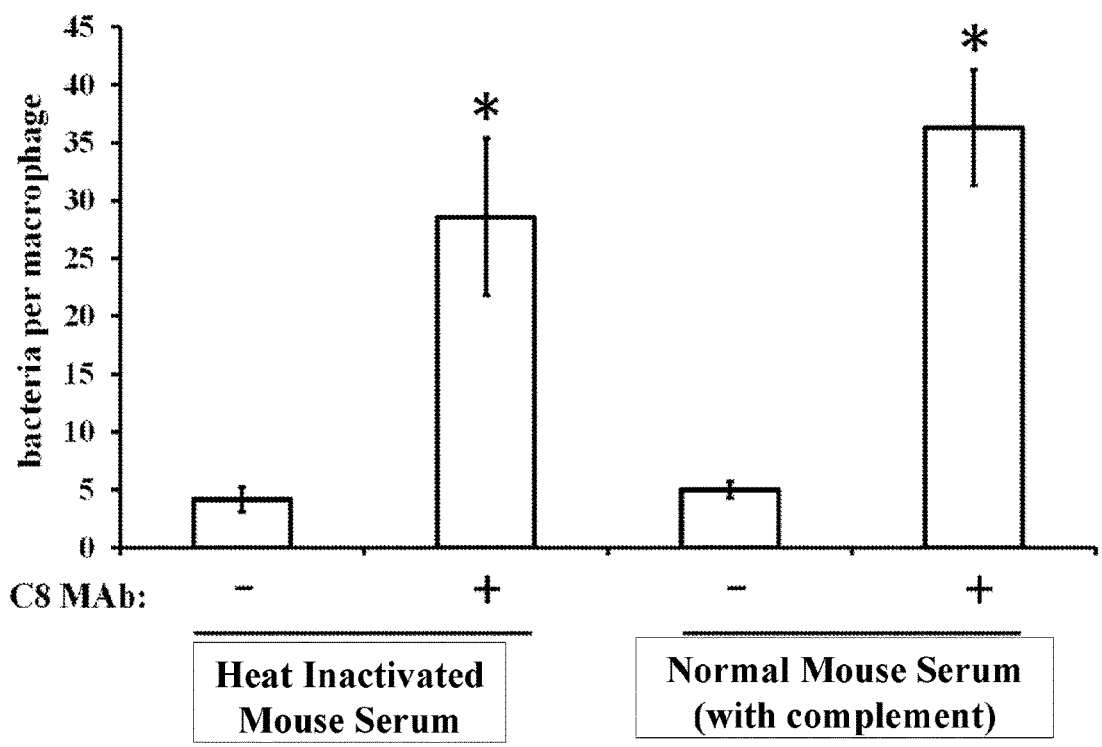
FIG. 6B shows, in contrast, that the C8 MAb markedly improved macrophage uptake of *A. baumannii*. *A. baumannii* HUMC1 log-phase bacteria were incubated for 1 hour in media with 10% FBS (fetal bovine serum, heat-inactivated or not) with RAW 264.7 macrophages that had been stimulated overnight with IFNγ. C8 MAb was added at a final concentration of 5 µg/mL. The C8 MAb enhances macrophage uptake of *A. baumannii* in the presence or absence of complement, but enhancement was greatest with complement. *p<0.05.

6A). Thus, the antibody alone did not inhibit bacterial growth. The ability of C8 to opsonize bacteria to enhance macrophage uptake was tested next. The addition of C8 MAb markedly increased macrophage uptake of *A. baumannii*, whether in the presence of HI or complement-active serum (FIG. 6B). However, the highest uptake was achieved with C8 MAb plus normal serum with active complement. These results indicated that the C8 MAb enhanced macrophage uptake of *A. baumannii* HUMC1 via both complement-dependent and -independent mechanisms.

Figure 7A:
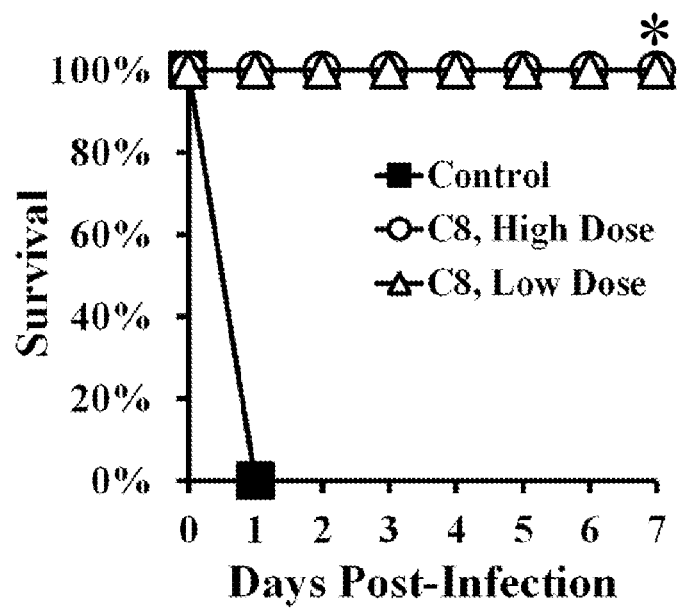
FIG. 7A shows a survival plot of C3HeB/FeJ mice (n=10 per group) infected i.v. via the tail-vein with *A. baumannii* HUMC1 (1.7×10$^7$ bacteria) and treated immediately i.v. with C8 MAb at approximately 50 µg (low dose) or 150 µg (high dose), or isotype control IgG MAb (Control).
Figure 7B:
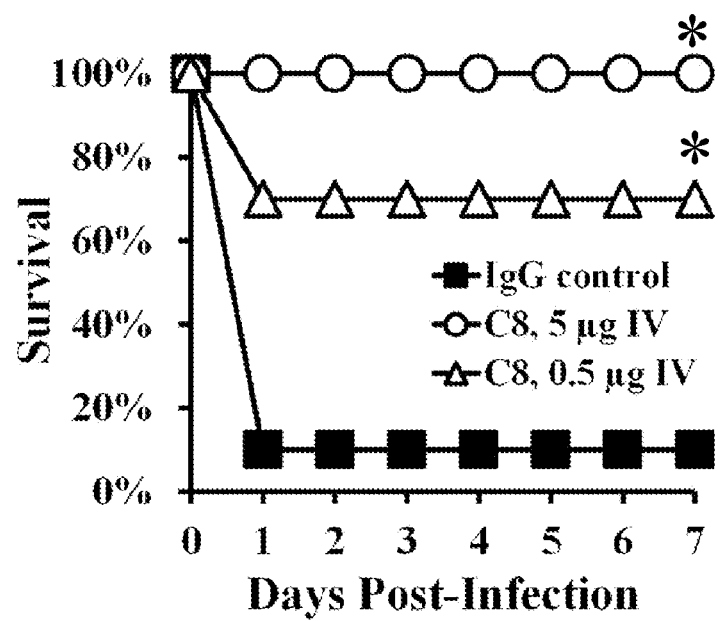
FIG. 7B shows a survival plot of C3HeB/FeJ mice (n=10 per group) infected i.v. via the tail-vein with *A. baumannii* HUMC1 (1.7×10$^7$ bacteria) and treated either immediately or after 4 hours with C8 MAb at 5 µg, or immediately with 0.5 µg.

In Vivo MAb Treatment of Mice Protects Against Lethal *A. baumannii* Bloodstream Infection We evaluated the efficacy of the C8 MAb as a treatment for lethal bloodstream infection caused by *A. baumannii* HUMC1. When mice were infected intravenously with a 100% lethal inoculum of hyper-virulent *A. baumannii* HUMC1 and immediately treated with different concentrations of either C8 MAb or control, the C8 MAb was 100% protective against infection at both a low and high dose (FIG. 7A). Defined doses of purified C8 MAb were tested in a repeat experiment and found that a dose as low as 5 µg was fully protective against iv infection, while a dose of 0.5 µg significantly improved survival although it was less effective than 5 µg (FIG. 7B).

Figure 7C:
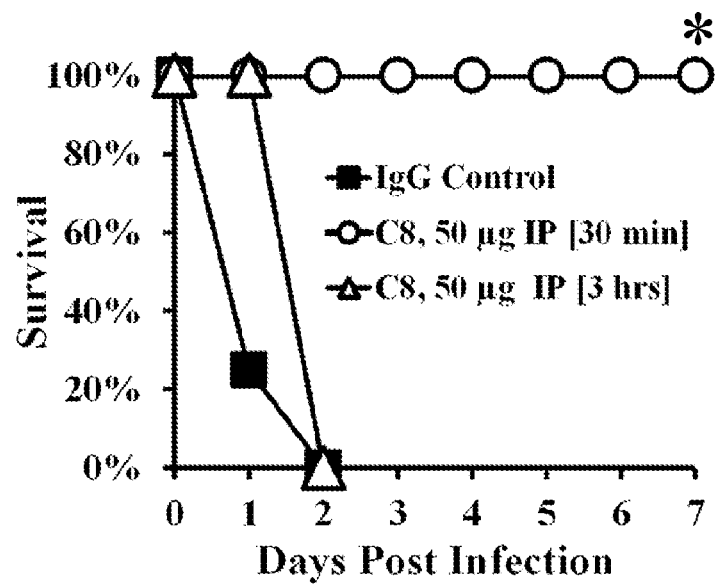
FIG. 7C shows a survival plot of C3HeB/FeJ mice infected i.v. with *A. baumannii* (n=8 per group) and treated i.p. with C8 (50 µg) or isotype control MAb at the time points post-infection shown.
Figure 7D:
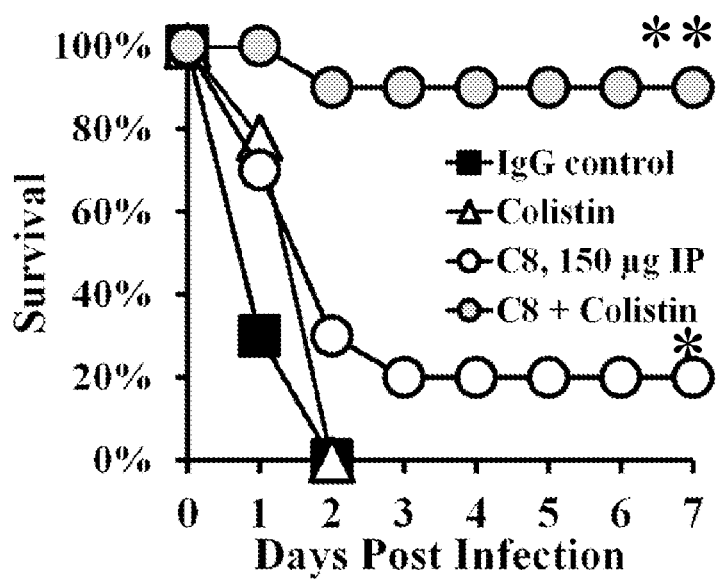
FIG. 7D shows a survival plot of C3HeB/FeJ mice infected i.v. with *A. baumannii* (n=10 per group, 2 experiments combined) and treated i.p. with C8 (150 µg) with or without colistin (0.0125 mg/kg) at 1 hr post-infection. *p<0.05 vs. control, **p<0.05 vs. control and monotherapy.

It has been shown that achievement of a high blood bacterial density ($\geq 10^7$/ml) within an hour of *A. baumannii* infection results in uniformly fatal infection, whereas lower bacterial densities at that time point enable mice to subsequently clear the infection. Larger doses of C8 were tested and delivered ip at various time points following iv infection, to determine the impact of delaying treatment. Mice could be rescued from lethal infection when treated at 30 min post-infection (FIG. 7C), but not all mice survived when treatment was delayed to 1 hr post-infection, even with higher doses of MAb (FIG. 7D).

Because clinical treatment of *A. baumannii* infection will likely occur in conjunction with antibiotic treatment, the efficacy of combined treatment of MAb with colistin was assessed at 1 hr post-infection. While monotherapy with the C8 MAb during delayed therapy once again minimally improved survival, delayed colistin monotherapy was completely ineffective (FIG. 7D). In contrast, delayed combination therapy was markedly synergistic, resulting in virtually complete protection (90% survival) against lethal bloodstream infection (FIG. 7D). Of note, the MIC of colistin against HUMC1 was tested alone or in the presence of C8 at 0.1, 1, or 10 µg/mL and the MIC was identical in all four conditions (2 µg/mL).

C8 Reduced CFUs and Ameliorated Sepsis Syndrome

Figure 8A:
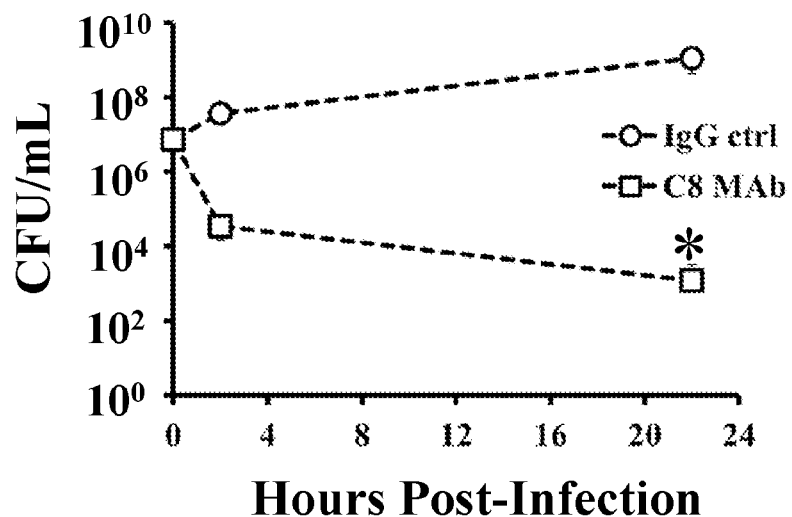
FIG. 8A shows bacterial density of *A. baumannii* in the blood of infected mice treated with C8 MAb or IgG isotype control after an i.v. injection of *A. baumannii*. Mice were euthanized and cardiac punctured to obtain blood at 2 and 22 hours after infection, and *A. baumannii* (colony forming units) CFUs were determined by diluting and plating on agar plates and counting.

To determine the mechanism of protection in vivo, the impact of C8 MAb therapy on bacterial density and sepsis syndrome in infected was studied in treated mice. Mice were infected iv via the tail-vein with HUMC1 and then treated with C8 MAb. At two hours after treatment, C8-treated mice had 1,000-fold lower bacterial density in the blood than mice treated with an isotype control antibody (FIG. 8A). Bacterial density in the blood of C8-treated mice continued to decrease over the next 20 h, while control mice displayed increasing bacterial burden before succumbing to infection.

Figure 8B:
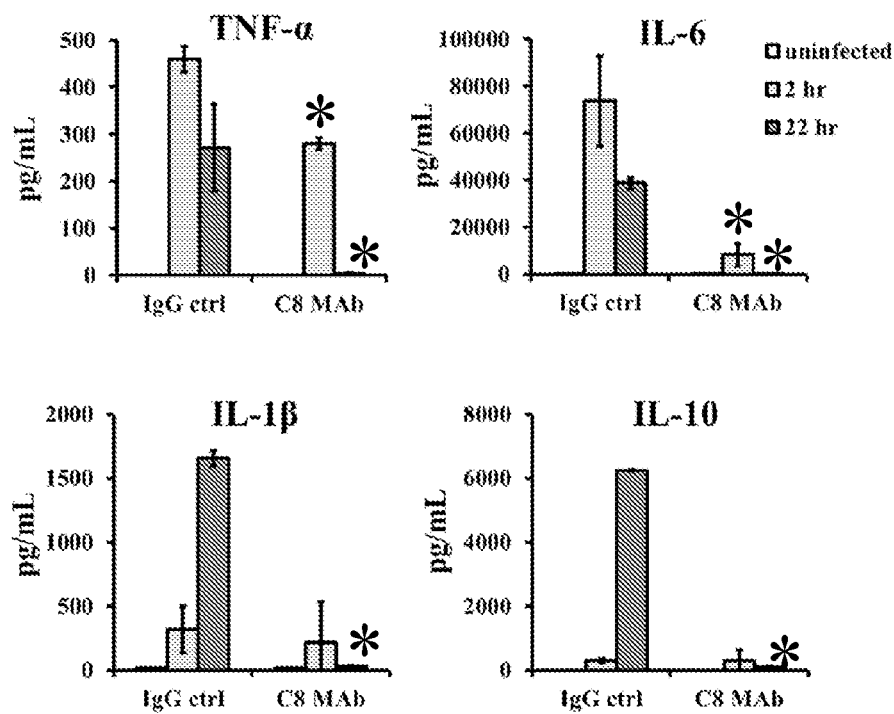
FIG. 8B shows blood plasma cytokine levels at the given time points in infected and treated mice, as assayed by Luminex assay.
Figure 8C:
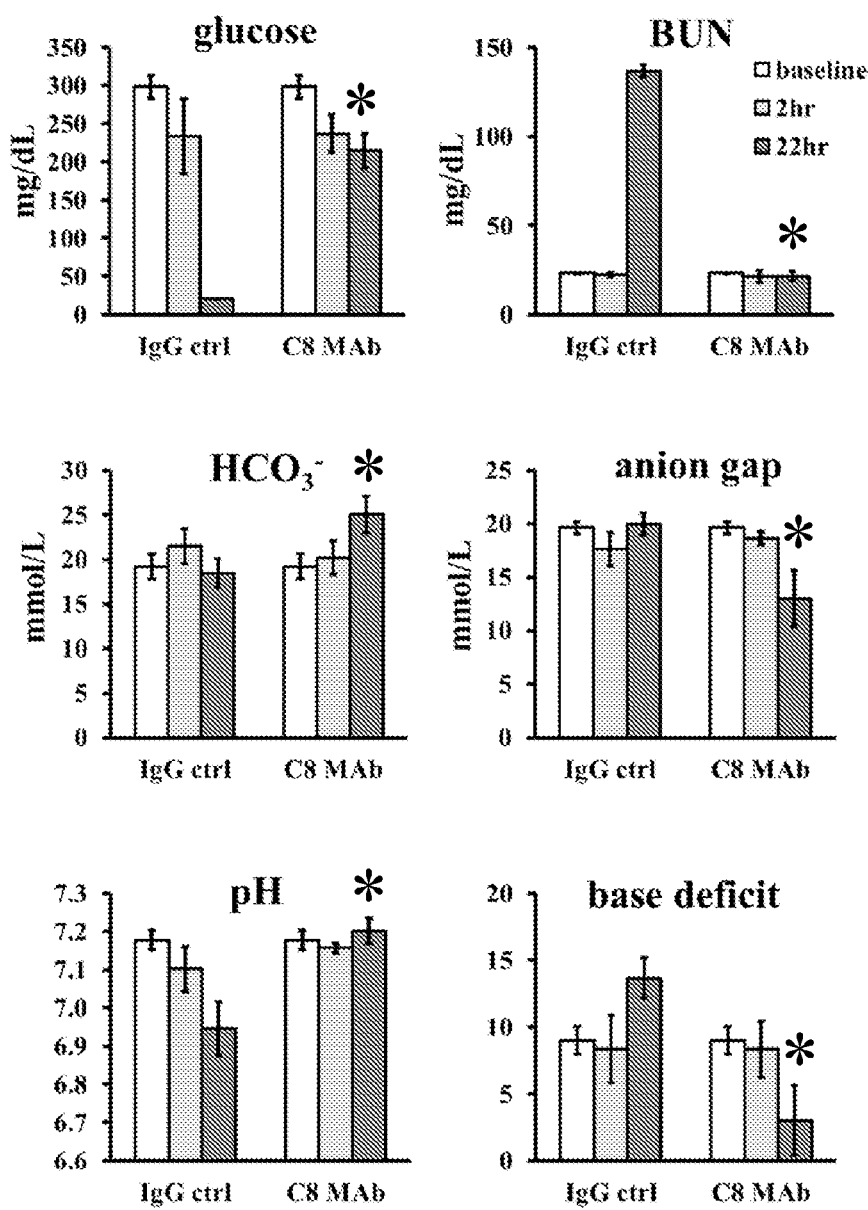
FIG. 8C shows biomarkers of sepsis in infected mice by analyzing blood samples to determine indicators of sepsis, renal failure, hypoglycemia, and metabolic acidosis that develop in infected control mice. Control mice developed progressive septic shock between 2 and 24 hours, while C8-treated mice maintained baseline physiology. *p<0.05 vs. control.

Cytokine responses were also dramatically reduced in C8-treated mice, correlating with their reduced bacterial load (FIG. 8B). TNF and IL-6, which were induced early (2 hr) after infection, were significantly reduced in C8-treated mice at this time point. IL-1β and IL-10, which were present at high levels by 22 hr post-infection, were virtually undetectable in C8-treated mice. Biomarkers for sepsis were also measured. Infected control mice developed severe renal failure (very high blood urea nitrogen [BUN]) and hypoglycemia, severe metabolic acidosis, with low bicarbonate, high anion gap, high base deficit, and low blood pH, all consistent with septic shock. C8-treated mice, in comparison, had baseline BUN levels at 22 hr post-infection, as well as normal blood glucose, serum bicarbonate, anion gap, base deficit, and blood pH, relative to controls.

Figure 9A:
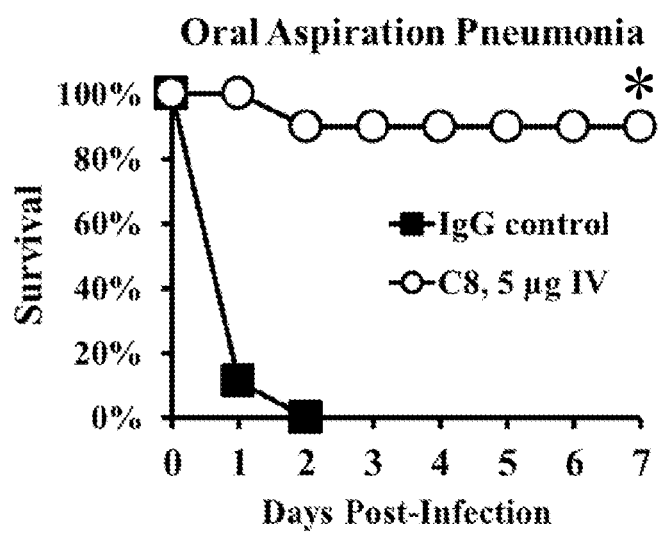
FIG. 9A shows a survival plot of C3HeB/FeJ mice (n=10 per group) infected with *A. baumannii* HUMC1 via oropharyngeal aspiration (1.5×10$^8$ CFUs) and treated i.v. with C8 MAb (5 µg) or IgG1 isotype control MAb.
Figure 9B:
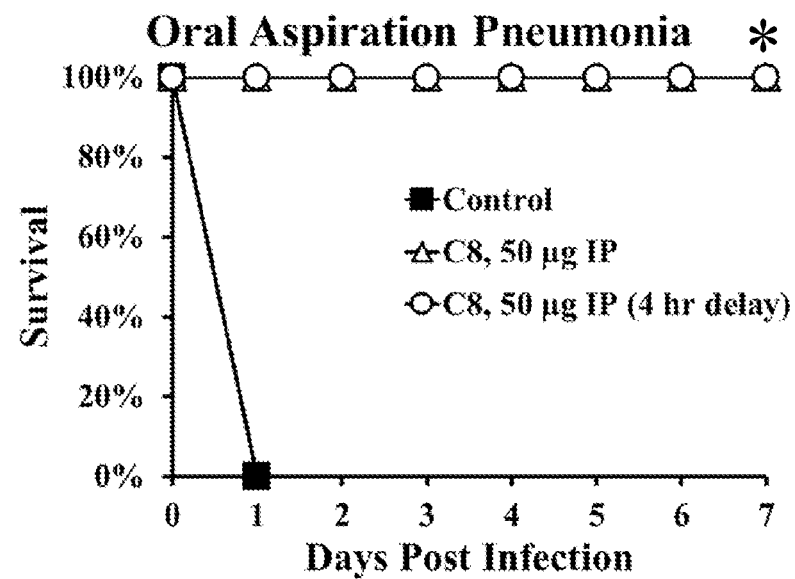
FIG. 9B shows a survival plot of C3HeB/FeJ mice infected OA with 1.5E8 CFUs *A. baumannii* (n=5 per group) and treated immediately or 4 hr post-infection i.p. with 50 µg C8 MAb. *p<0.05 vs. control.
Figure 9D:
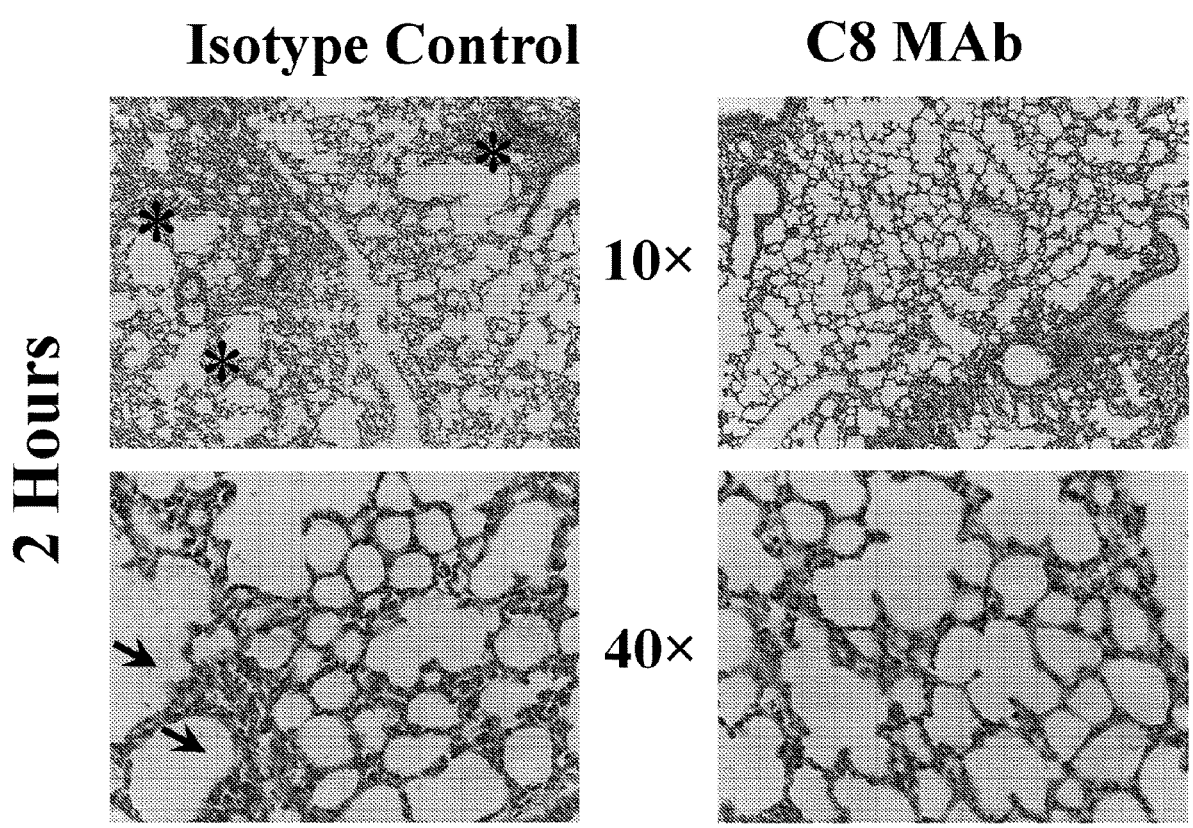
FIG. 9D and FIG. 9E shows H&E stained lungs from the same mice demonstrated onset of pulmonary consolidation (white asterisks, 5× power) and thickened intra-lobular septa (black arrows, 40× power) by 2 hours after infection (FIG. 9D), which transformed into severe alveolar hemorrhagic consolidation by 24 hours after infection (FIG. 9E) in the control mice. In contrast, C8-treated mice maintained normal lung architecture.
Figure 9E:
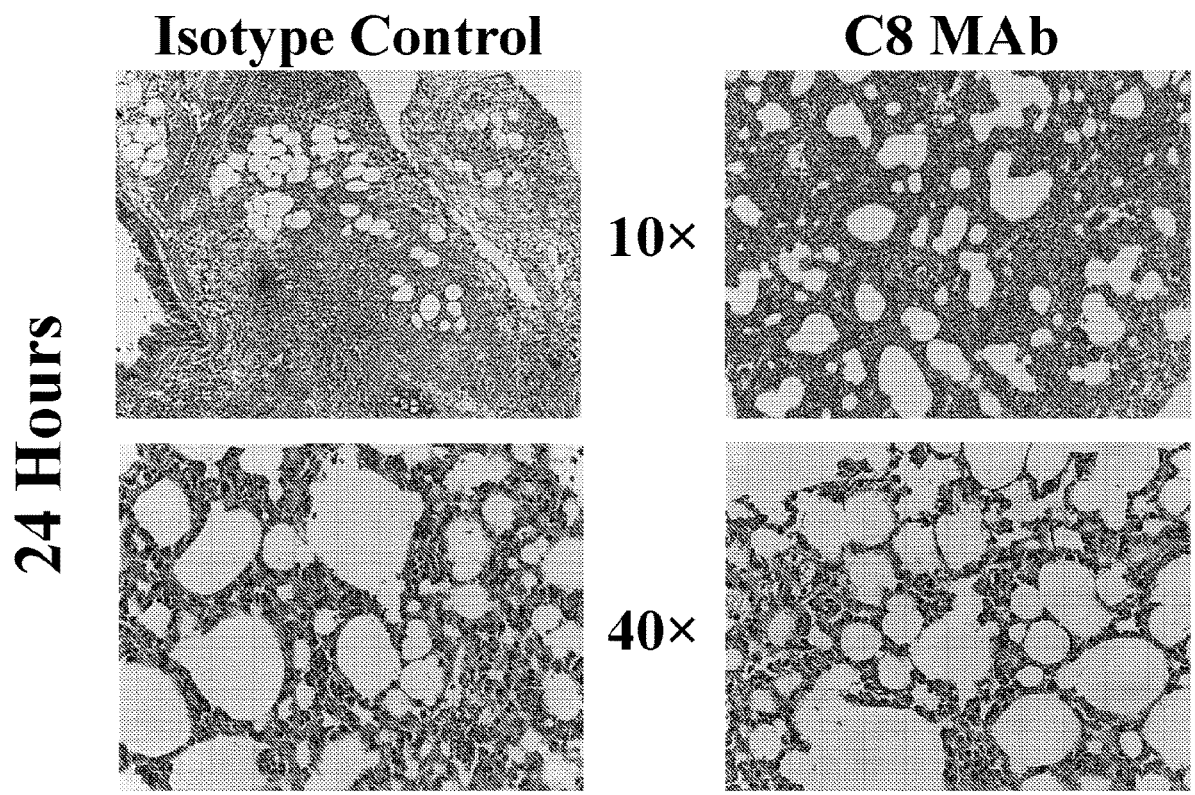
Figure 9F:
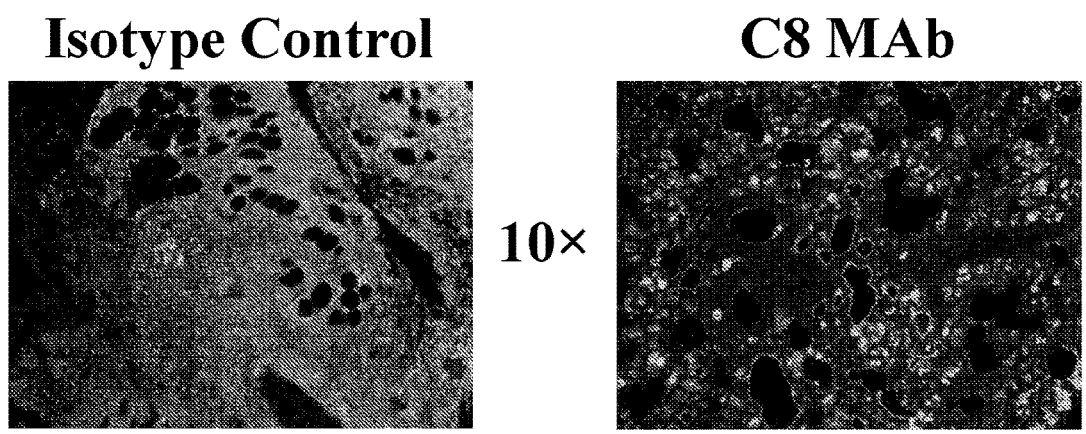
FIG. 9F shows fluorescence microscopy of lung tissue (DAPI, blue) from the same mice infected with *A. baumannii* (Alexa488, green) which confirmed C8-treated mice were better able to clear bacteria than the control mice. *p<0.05 vs. control.
Figure 10A:
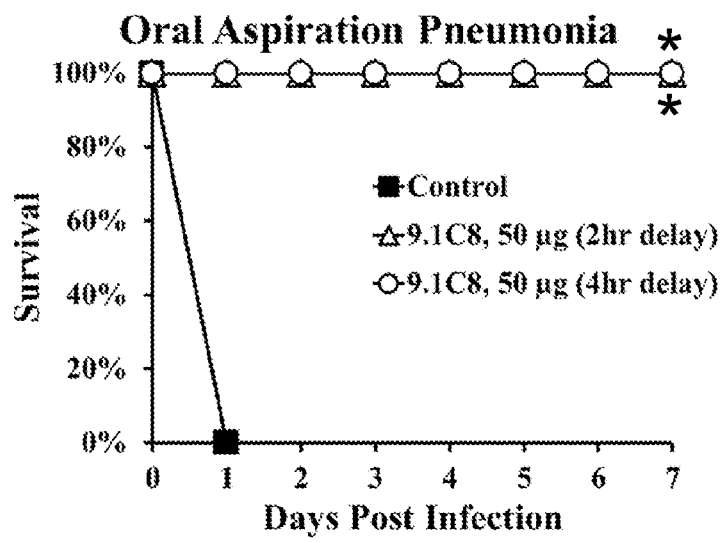
FIGS. 10A and 10B. The effect of dose and timing of administration of antibody 9.1.C8 on the survival of infected mice.
Figure 10B:
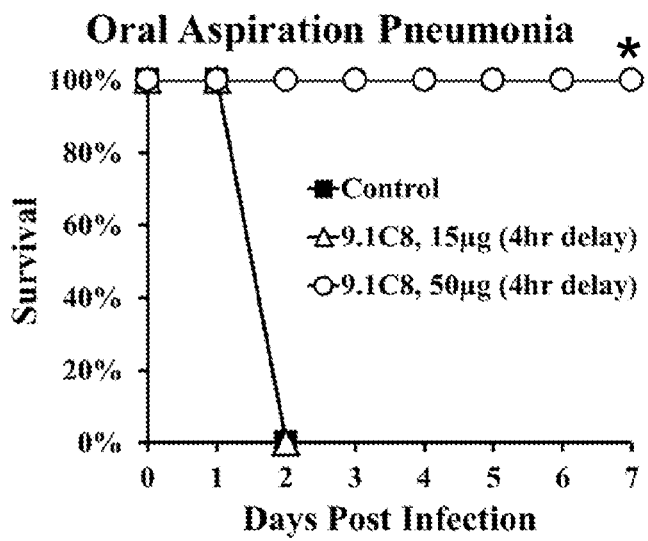

In Vivo MAb Treatment of Mice Protects Against Lethal *A. baumannii* Lung Infection The efficacy of C8 in another clinically relevant in vivo model of infection, an aspiration pneumonia model consistent with the most common form of clinical *A. baumannii* infection, was tested. As in the bloodstream model, C8 was nearly fully protective against aspiration pneumonia in mice at a treatment dose of 5 µg delivered iv and C8 was fully protective at a treatment dose of 50 µg delivered ip (FIG. 9A-B). At 24 hr post-infection, bacterial burden in both the lungs and the blood decreased significantly (2-log and 7-log reductions, respectively) in mice treated with 50 µg C8 compared to control mice (FIG. 9C). When examined by fluorescence microscopy, bacterial burden in the lungs is clearly greater in the control mice than the C8-treated mice (FIGS. 9D, 9E & 9F). By 2 hr post-infection, control-mouse lungs began to demonstrate thickened intra-lobular septa and early consolidation (FIG. 9D). At 24 hr post-infection, control-mouse lungs demonstrated severe hemorrhagic alveolar consolidation, while lungs from C8-treated mice appeared normal (FIG. 9E).

Discussion

Over the past decade *A. baumannii* has emerged as a critical, unmet need for development of novel treatments. These infections result in unacceptably high mortality rates, particularly for XDR/PDR strains that have limited/no effective antibiotics to treat. Identification of an effective MAb-based immunotherapy is of substantial importance, since few new antibacterial therapies for these lethal infections will likely be available in the coming decade. Anti-*A. baumannii* polyclonal antibodies were highly protective as therapy for iv infection. However, efforts to raise effective MAbs against a specific target were unsuccessful. Therefore MAbs against *A. baumannii* were made by whole-organism immunization. A MAb, C8, was identified that bound to the surface of *A. baumannii* and was highly effective at treating iv and lung infections caused by hyper-virulent, clinical isolates, including when therapy was delayed. Of great translational importance is the synergy observed when mice were given delayed combination therapy with MAb plus colistin, the latter of which is the standard antibiotic treatment for XDR *A. baumannii* infections.

Mice infected iv with hyper-virulent *A. baumannii* succumb to lethal, LPS-TLR4-driven septic shock. Achievement of a bacterial density of $\geq 10^7$ CFU/mL in the blood by 1 hr post-infection invariably led to subsequent onset of uniformly fatal septic shock, with severe metabolic acidosis. In contrast, mice that were able to clear bacteria and achieve lower bacterial density in the blood within the first hour, subsequently cleared the infection and survived. The results herein highlight the importance of an early, post-infection window. For example, the administration of the MAb within 1 hr post-infection enabled the mice to clear the bacteria, avoid onset of septic shock, and survive the infection. The window of post infection treatment may be much longer in human subjects and may depend largely on many factors, including the virulence of the bacterial, the degree of infection (i.e., overall bacterial count), the level of antibiotic resistance of the bacterial, growth rate of the bacteria, the anatomical location of an infection, the response of the bacterial infection to other treatments which may slow grow rates, and the overall health and the immune-competence of a subject. Administration of C8 intraperitoneally (with presumably additional delay in achieving peak plasma levels) 1 hr post-infection was too late, as the sepsis cascade had already been triggered, and mice progressed to septic shock and renal failure. These results are consistent with extensive clinical data in septic shock showing that mortality rapidly rises within an hour if effective therapy is not administered. However, in the lung model of infection, pneumonia did not appear histologically until two hours after infection, affording a greater window of opportunity to initiate delayed therapy. Indeed we found that C8 MAb therapy administered 4 hr post-infection was fully protective. MAbs will rarely be administered as a monotherapy in a clinical settings, and will usually be combined with antibacterial therapy. Thus, these data confirming that the C8 MAb is synergistic with antibiotic therapy suggests that antibody treatment combined with existing antibiotics represents a feasible therapeutic in patients presenting with *A. baumannii* infections.

In summary, MAb, C8, is highly protective against bloodstream and lung models of *A. baumannii* infection, including against a hyper-virulent, XDR clinical isolate. The MAb enhanced bacterial clearance, preventing progression to septic shock, and worked synergistically when combined with antibiotic therapy. These results support rapid translational development as an adjunctive therapy for *A. baumannii* infection, and particularly for therapy for XDR strains for which antibacterial regimens are currently inadequate.

TABLE 7

*A. baumannii* clinical strains used in the current study.

| Strain | Strain Type | Characteristics |
|---|---|---|
| HUMC1 | ST 2 | Carbapenem-resistant, hyper-virulent, clinical blood and lung isolate from a patient with bacteremic, ventilator-associated pneumonia (13, 14) |
| HUMC6 | ST 2 | Carbapenem-resistant, virulent clinical lung isolate (13, 14) |
| C14 | ST107 | Colistin-resistant, pmrB mutant virulent clinical wound isolate (25) |
| ATCC 17978 | ST 112 | Hypo-virulent clinical CSF isolate (26) |
| AB0071 | NA | Skin swab sample (26) |
| UH7007 | ST 2 | Clinical urine isolate (27) |

Example 4

The nucleic acid coding regions encoding the entire heavy and light chains of the mouse C8 monoclonal antibody are subcloned into an mammalian expression vector that directs the expression of both the heavy and light chains under the direction of a CMV promoter. The vector is named C8-mouseHL. Using standard sub-cloning techniques, the nucleic acids of C8-mouseHL that encode the mouse light chain framework regions and heavy chain framework regions are replaced with the corresponding framework regions from a human IgG1 antibody. In addition, the nucleic acids of C8-mouseHL that encode the remaining constant regions of the heavy and light chains were also replaced with nucleic acids encoding the heavy and light chain constant regions of human IgG1, respectively. The resulting vector is named C8-humanHL. The C8-humanHL is transfected into COS cells and stable cell lines were selected. The stably transfected cell line is used to express the humanized C8 IgG1 monoclonal into the culture media. Conditioned culture media is collected and the antibody is purified by protein A column chromatography. The purified humanized C8 IgG1 monoclonal is resuspended in a pharmaceutically acceptable buffer. The humanized C8 IgG1 monoclonal is tested and confirmed for specific binding to *A. baumannii*. Variants of the above humanized antibody are made and optimized by systematically exchanging one or more of the heavy or light chain variable region of the humanized C8 IgG1 monoclonal antibody with one or more, or all of the variable regions of the R2D2 mouse monoclonal antibody. Further optimization is performed by strategically introducing single amino acid substitutions within the heavy and light chain variable regions.

Determining Binding and Efficacy

The humanized C8 IgG1 monoclonal antibody, or a variant thereof, is administered i.v. to a first group of mice at a dose of 0.5, 1, 2, 4, 10 or 100 mg/kg, 24 hours prior to infection with $2\times10^6$ of *A. baumannii* introduced i.v. via the tail-vein. The humanized C8 $IgG_1$ monoclonal is administered i.v. to a second group of mice at a dose of 0.5, 1, 2, 4, 10 or 100, 24 hours after infection with $2\times10^6$ of *A. baumannii* introduced i.v. via the tail-vein. Control mice were administered humanized C8 IgG1 monoclonal without *A. baumannii*, or were administered an isotype control antibody with or without *A. baumannii*. The efficacy of antibody prophylaxis and treatment is determined by counting live mice for each treatment group at 1, 2, 3, 4, 5, 6 and 7 days after infection.

Example 5

A patient suffers from a systemic or local fungal infection where the presence or amount of *A. baumannii* is identified in a sample obtained from the patient. The presence or absence of *A. baumannii* is identified by obtaining a sample (e.g., serum sample) and performing an ELISA-based assay. Briefly, plastic wells are coated with a mouse antibody that specifically binds *A. baumannii* (e.g., C8) followed by addition of a serum sample suspected of containing *A. baumannii*. After washing, *A. baumannii* is detected by adding a humanized C8 IgG1 monoclonal antibody, or a variant thereof, (e.g., from Example 3) followed by addition of a suitable goat anti-human antibody conjugated with horse radish peroxidase (HRP). Bound humanized C8 IgG1 monoclonal, which is reflective of the amount and/or presence of *A. baumannii*, is assessed by a color change after addition of a suitable HPR substrate. If *A. baumannii* is detected in the patient sample, the patient is administered a pharmaceutical composition comprising the humanized C8 IgG1 monoclonal antibody, or a variant thereof, (e.g., from Example 3) by i.v. infusion at an optimal dose (e.g., 4 mg/kg of body weight) every 72 hours or as needed. The administration of humanized antibody is adjusted, continued, or discontinued according to assessing the patients status by a medical professional and/or by re-testing for the amount, presence or absence of *A. baumannii* in a second sample obtained from the patient after or during treatment.

Example 6—Embodiments

A0. An antibody binding agent that specifically binds to *A. baumannii,* wherein the antibody binding agent comprises three CDRs of a light chain variable domain of SEQ ID NO:2 or three CDRs of a light chain variable domain of SEQ ID NO:28.

A0.1. An antibody binding agent that specifically binds to *A. baumannii*, wherein the antibody binding agent comprises three CDRs of a heavy chain variable domain of SEQ ID NO:3, three CDRs of a heavy chain variable domain of SEQ ID NO:67, or three CDRs of a heavy chain variable domain of SEQ ID NO:29.

A0.2. An antibody binding agent that specifically binds to *A. baumannii*, wherein the antibody binding agent comprises three CDRs of a light chain variable domain selected from the CDRs of Tables 1, 2 and 3, and three CDRs of a heavy chain variable domain selected from the CDRs of Tables 4, 5 and 6.

A0.3. An antibody binding agent that specifically binds to *A. baumannii*, wherein the antibody binding agent comprises a CDR-L1 selected from Table 1, a CDR-L2 selected from Table 2, a CDR-L3 selected from Table 3, a CDR-H1 selected from Table 4, a CDR-H2 selected from Table 5 and a CDR-H3 selected from Table 6.

A0.4. An antibody binding agent that specifically binds to *A. baumannii*, wherein the antibody binding agent comprises a CDR-L1 that is at least 80% identical to a CDR selected from Table 1, a CDR-L2 that is at least 80% identical to a CDR selected from Table 2, a CDR-L3 that is at least 80% identical to a CDR selected from Table 3, a CDR-H1 that is at least 80% identical to a CDR selected from Table 4, a CDR-H2 that is at least 80% identical to a CDR selected from Table 5 and a CDR-H3 that is at least 80% identical to a CDR selected from Table 6.

A0.5. The binding agent of any one of embodiments A0 to A0.4, wherein the binding agent is a monoclonal binding agent.

A1. A pharmaceutical composition comprising:

an antibody binding agent that specifically binds to *A. baumannii*; and a pharmaceutical acceptable excipient, diluent, additive or carrier;

wherein the antibody binding agent comprises three CDRs of a light chain variable domain of SEQ ID NO:2 or SEQ ID NO:28.

A1.1. A pharmaceutical composition comprising:

an antibody binding agent that specifically binds to *A. baumannii*; and a pharmaceutical acceptable excipient, diluent, additive or carrier;

wherein the antibody binding agent comprises three CDRs of a heavy chain variable domain of SEQ ID NO:3, SEQ ID NO:29 or SEQ ID NO:67.

A1.2. A pharmaceutical composition comprising:

an antibody binding agent that specifically binds to *A. baumannii*; and a pharmaceutical acceptable excipient, diluent, additive or carrier;

wherein the antibody binding agent comprises three CDRs of a light chain variable domain selected from selected from the CDRs of Tables 1, 2 and 3, and three CDRs of a heavy chain variable domain selected from the CDRs of Tables 4, 5 and 6.

A2. The pharmaceutical composition of any one of embodiments A1 to A1.2, wherein the antibody binding agent comprises an antibody, or a binding fragment thereof.

A3. The pharmaceutical composition of embodiment A2, wherein the antibody is a monoclonal antibody, or binding fragment thereof.

A4. The pharmaceutical composition of embodiment A3, wherein the monoclonal antibody is a mouse monoclonal antibody.

A5. The pharmaceutical composition of any one of embodiments A1 to A4, wherein the antibody binding agent comprises a constant region of an $IgG_1$, $IgG_2$, IgG3, or IgG4.

A6. The pharmaceutical composition of any one of embodiments A1 to A4, wherein the antibody binding agent comprises a constant region of an IgD, IgE, IgA or IgM.

A7. The pharmaceutical composition of any one of embodiments A1 to A6, wherein the antibody binding agent is humanized.

A7.1. The pharmaceutical composition of any one of embodiments A1 to A7, wherein the antibody binding agent comprises at least 1 humanized or human framework region.

A7.2. The pharmaceutical composition of any one of embodiments A1 to A7.1, wherein the antibody binding agent comprises at least 3 humanized or human framework regions.

A8. The pharmaceutical composition of any one of embodiments A1 to A7.2, wherein the antibody binding agent comprises at least 1 mouse framework region.

A8.1. The pharmaceutical composition of any one of embodiments A1 to A8, wherein the antibody binding agent comprises at least 3 mouse framework regions.

A9. The pharmaceutical composition of any one of embodiments A1 to A8.1, wherein the antibody binding agent is a Fab, Fab', F(ab')$_2$, Fv or scFV fragment of an antibody.

A10. The pharmaceutical composition of any one of embodiments A1 to A9, wherein the antibody binding agent consist of a single chain polypeptide.

A11. The pharmaceutical composition of any one of embodiments A1 to A1.2, wherein the antibody binding agent comprises the amino acid sequence of SEQ ID NO:2.

A12. The pharmaceutical composition of any one of embodiments A1 to A11, wherein the antibody binding agent comprises the amino acid sequence of SEQ ID NO:3.

A12.1. The pharmaceutical composition of any one of embodiments A1 to A11, wherein the antibody binding agent comprises the amino acid sequence of SEQ ID NO:67.

A13. The pharmaceutical composition of any one of embodiments A1 to A12.1, wherein the antibody binding agent is a neutralizing binding agent.

A14. The pharmaceutical composition of any one of embodiments A1 to A13, wherein the antibody binding agent inhibits *A. baumannii* induced death in mice.

A15. The pharmaceutical composition of any one of embodiments A1 to A14, wherein the pharmaceutical composition is substantially free of endotoxin.

A16. The pharmaceutical composition of any one of embodiments A1 to A15, wherein the pharmaceutical composition is substantially free of serum or serum proteins.

A17. The pharmaceutical composition of any one of embodiments A1 to A16, wherein the pharmaceutical composition is substantially free of serum proteins.

A18. The pharmaceutical composition of any one of embodiments A1 to A17, wherein the additive comprises a preservative.

A19. The pharmaceutical composition of any one of embodiments A1 to A18, wherein the diluent comprises phosphate buffered saline.

A20. The pharmaceutical composition of any one of embodiments A1 to A19, wherein the excipient comprises sodium citrate dehydrate or polysorbate 80.

A21. The pharmaceutical composition of any one of embodiments A1 to A20, wherein the carrier comprises a recombinant protein.

A22. The pharmaceutical composition of any one of embodiments A1 to A21, further comprising an anti-bacterial medication.

A23. The pharmaceutical composition of any one of embodiments A1 to A22, wherein the pharmaceutical composition is sterile.

A24. The pharmaceutical composition of any one of embodiments A1 to A23, wherein the pharmaceutical composition is formulated as a sterile, lyophilized powder suitable for intravenous administration to a mammal.

A25. A pharmaceutical composition of any one of embodiments A1 to A24 comprising:
an antibody binding agent that specifically binds to *A. baumannii*; and
a pharmaceutical acceptable excipient, diluent, additive or carrier;
wherein the antibody binding agent comprises the three CDRs of the light chain variable domain of SEQ ID NO:2 and the three CDRs of the heavy chain variable domain of SEQ ID NO:3.

A26. A pharmaceutical composition of any one of embodiments A1 to A24 comprising:
an antibody binding agent that specifically binds to *A. baumannii*; and
a pharmaceutical acceptable excipient, diluent, additive or carrier;
wherein the antibody binding agent comprises the three CDRs of the light chain variable domain of SEQ ID NO:2 and the three CDRs of the heavy chain variable domain of SEQ ID NO:67.

A27. A pharmaceutical composition of any one of embodiments A1 to A24 comprising:
an antibody binding agent that specifically binds to *A. baumannii*; and
a pharmaceutical acceptable excipient, diluent, additive or carrier;
wherein the antibody binding agent comprises the three CDRs of the light chain variable domain of SEQ ID NO:28 and the three CDRs of the heavy chain variable domain of SEQ ID NO:29.

B1. A humanized antibody binding agent comprising:
a light chain variable domain comprising three CDRs of SEQ ID NO:2, wherein
the humanized antibody binding agent specifically binds to *A. baumannii*.

B1.1. A humanized antibody binding agent comprising:
a heavy chain variable domain comprising three CDRs of SEQ ID NO:3, wherein the humanized antibody binding agent specifically binds to *A. baumannii*.

B1.2. A humanized antibody binding agent comprising:
a light chain variable domain comprising three CDRs of SEQ ID NO:2 or SEQ ID NO:28; and
a heavy chain variable domain comprising three CDRs of SEQ ID NO:3 or SEQ ID NO:29; wherein
the humanized antibody binding agent specifically binds to *A. baumannii*.

B1.3. A humanized antibody binding agent comprising:
a light chain variable domain comprising three CDRs of SEQ ID NO:2; and
a heavy chain variable domain comprising three CDRs of SEQ ID NO:67; wherein
the humanized antibody binding agent specifically binds to *A. baumannii*.

B2. The humanized antibody binding agent of any one of embodiments B1 to B1.3, wherein the humanized antibody binding agent is a monoclonal antibody, or binding fragment thereof.

B3. The humanized antibody binding agent of any one of embodiments B1 to B2, wherein the humanized antibody binding agent comprises a constant region of an IgG1, IgG2, IgG3, or IgG4.

B4. The humanized antibody binding agent of any one of embodiments B1 to B2, wherein the humanized antibody binding agent comprises a constant region of an IgD, IgE, IgA or IgM.

B5. The humanized antibody binding agent of any one of embodiments B1 to B4, wherein the humanized antibody binding agent comprises at least 1 humanized or human framework region.

B6. The humanized antibody binding agent of any one of embodiments B1 to B5, wherein the humanized antibody binding agent comprises at least 3 humanized or human framework regions.

B7. The humanized antibody binding agent of any one of embodiments B1 to B6, wherein the humanized antibody binding agent comprises 6 humanized or human framework regions.

B8. The humanized antibody binding agent of any one of embodiments B1 to B7, wherein the humanized antibody binding agent is a Fab, Fab', F(ab')$_2$, Fv or scFV fragment of an antibody.

B9. The humanized antibody binding agent of any one of embodiments B1 to B8, wherein the humanized antibody binding agent consist of a single chain polypeptide.

B10. The humanized antibody binding agent of any one of embodiments B1 to B9, wherein the humanized antibody binding agent is a neutralizing antibody binding agent.

B11. The humanized antibody binding agent of any one of embodiments B1 to B10, wherein the humanized antibody binding agent inhibits *A. baumannii* induced death in mice.

B12. The humanized antibody binding agent of any one of embodiments B1 to B11, and a pharmaceutically acceptable excipient.

C1. A humanized antibody binding agent comprising:
a light chain variable domain comprising at least two CDRs chosen from a CDR-L1 of Table 1, a CDR-L2 of Table 2 and a CDR-L3 of Table 3, wherein
the humanized antibody binding agent specifically binds to *A. baumannii*.

C2. A humanized antibody binding agent comprising:
a heavy chain variable domain comprising at least two CDRs chosen from a CDR-H1 of Table 4, a CDR-H2 of Table 5 and a CDR-H3 of Table 6, wherein
the humanized antibody binding agent specifically binds to *A. baumannii*.

C3. A humanized antibody binding agent comprising:
a light chain variable domain comprising at least two CDRs chosen from a CDR-L1 of Table 1, a CDR-L2 of Table 2 and a CDR-L3 of Table 3; and
a heavy chain variable domain comprising at least two CDRs chosen from a CDR-H1 of Table 4, a CDR-H2 of Table 5 and a CDR-H3 of Table 6; wherein
the humanized antibody binding agent specifically binds to *A. baumannii*.

C4. The humanized antibody binding agent of any one of embodiments C1 to C3, comprising:
a light chain variable domain comprising three CDRs each chosen from a CDR-L1 of Table 1, a CDR-L2 of Table 2 and a CDR-L3 of Table 3, wherein
the humanized antibody binding agent specifically binds to *A. baumannii*.

C5. A humanized antibody binding agent comprising:
a heavy chain variable domain comprising three CDRs each chosen from a CDR-H1 of Table 4, a CDR-H2 of Table 5 and a CDR-H3 of Table 6, wherein
the humanized antibody binding agent specifically binds to *A. baumannii*.

C6. A humanized antibody binding agent comprising:
a light chain variable domain comprising three CDRs each chosen from a CDR-L1 of Table 1, a CDR-L2 of Table 2 and a CDR-L3 of Table 3; and
a heavy chain variable domain comprising three CDRs each chosen from a CDR-H1 of Table 4, a CDR-H2 of Table 5 and a CDR-H3 of Table 6; wherein
the humanized antibody binding agent specifically binds to *A. baumannii*.

C7. A humanized antibody binding agent comprising:
a light chain variable domain comprising CDR-L1 of SEQ ID NO:4, CDR-L2 of SEQ ID NO:8 and CDR-L3 of SEQ ID NO:12; and
a heavy chain variable domain comprising CDR-H1 of SEQ ID NO:16, CDR-H2 of SEQ ID NO:20 and CDR-H3 of SEQ ID NO:24; wherein
the humanized antibody binding agent specifically binds to *A. baumannii*.

C8. A humanized antibody binding agent comprising:
a light chain variable domain comprising CDR-L1 of SEQ ID NO:4, CDR-L2 of SEQ ID NO:8 and CDR-L3 of SEQ ID NO:12; and
a heavy chain variable domain comprising CDR-H1 of SEQ ID NO:16, CDR-H2 of SEQ ID NO:20 and CDR-H3 of SEQ ID NO:24; wherein
the humanized antibody binding agent specifically binds to *A. baumannii*.

D1. A method of preventing or treating an *A. baumannii* infection comprising:
a) providing a subject having or at risk of having an *A. baumannii* infection; and
b) administering to the subject a therapeutically effective amount of a pharmaceutical composition of any one of embodiments A1 to A27, wherein the antibody binding agent specifically binds to *A. baumannii*.

D1.1. A method of preventing or treating an *A. baumannii* infection comprising:
a) providing a subject having or at risk of having an *A. baumannii* infection; and
b) administering to the subject a therapeutically effective amount of a humanized antibody of any one of embodiments B1 to B12, or C1 to C8, wherein the antibody specifically binds to *A. baumannii*.

D1.2. A method of preventing or treating an *A. baumannii* infection comprising:
a) providing a subject having or at risk of having an *A. baumannii* infection; and
b) administering to the subject a therapeutically effective amount of a pharmaceutical composition comprises an antibody binding agent that specifically binds to *A. baumannii*, wherein the antibody binding agent comprises three or more CDRs each comprising at least 80% identity to any one of the CDRs selected from Table 1, Table 2, Table 3, Table 4, Table 5 and Table 6.

D2. The method of any one of embodiments D1 to D1.2, wherein the pharmaceutical composition is the pharmaceutical composition of any one of embodiments A1 to A27.

D3. The method of any one of embodiments C1 to C2, wherein the antibody binding agent is a humanized antibody binding agent of any one of embodiments B1 to B12 or C1 to C8.

E1. A pharmaceutical composition of any one of embodiments A1 to A27 for preventing or treating an *A. baumannii* infection.

E2. A humanized antibody binding agent of any one of embodiments B1 to B12 or C1 to C8 for preventing or treating an *A. baumannii* infection.

F1. An antibody binding agent that specifically binds to *A. baumannii*, wherein the antibody binding agent comprises three CDRs of a light chain variable domain of SEQ ID NO:2 and/or three CDRs of a heavy chain variable domain of SEQ ID NO:3.

F2. The antibody binding agent of embodiment F1, wherein the antibody binding agent comprises an antibody, or a binding fragment thereof.

F3. The antibody binding agent of embodiment F2, wherein the antibody is a monoclonal antibody, or binding fragment thereof.

F4. The antibody binding agent of embodiment F3, wherein the monoclonal antibody is a mouse monoclonal antibody.

F5. The antibody binding agent of any one of embodiments F1 to F4, wherein the antibody binding agent comprises a constant region of an IgG1, IgG2, IgG3, or IgG4.

F6. The antibody binding agent of any one of embodiments F1 to F4, wherein the antibody binding agent comprises a constant region of an IgD, IgE, IgF or IgM.

F7. The antibody binding agent of any one of embodiments F1 to F6, wherein the antibody binding agent is humanized.

F7.1. The antibody binding agent of any one of embodiments F1 to F7, wherein the antibody binding agent comprises at least 1 humanized or human framework region.

F7.2. The antibody binding agent of any one of embodiments F1 to F7.1, wherein the antibody binding agent comprises at least 3 humanized or human framework regions.

F8. The antibody binding agent of any one of embodiments F1 to F7.2, wherein the antibody binding agent comprises at least 1 mouse framework region.

F8.1. The antibody binding agent of any one of embodiments F1 to F8, wherein the antibody binding agent comprises at least 3 mouse framework regions.

F9. The antibody binding agent of any one of embodiments F1 to F8.1, wherein the antibody binding agent is a Fab, Fab', F(ab')2, Fv or scFV fragment of an antibody.

F10. The antibody binding agent of any one of embodiments F1 to F9, wherein the antibody binding agent consist of a single chain polypeptide.

F11. The antibody binding agent of any one of embodiments F1 to F10, wherein the antibody binding agent comprises the amino acid sequence of SEQ ID NO:2.

F12. The antibody binding agent of any one of embodiments F1 to F11, wherein the antibody binding agent comprises the amino acid sequence of SEQ ID NO:3.

F13. The antibody binding agent of any one of embodiments F1 to F12, wherein the antibody binding agent is a neutralizing binding agent.

F14. The antibody binding agent of any one of embodiments F1 to F13, wherein the antibody binding agent inhibits *A. baumannii* induced death in mice.

F15. The antibody binding agent of any one of embodiments F1 to F14, wherein the antibody binding agent is substantially free of endotoxin.

F16. The antibody binding agent of any one of embodiments F1 to F15, wherein the antibody binding agent is substantially free of serum or serum proteins.

F17. The antibody binding agent of any one of embodiments F1 to F16, wherein the antibody binding agent is substantially free of serum proteins.

F18. The antibody binding agent of any one of embodiments F1 to F17, wherein the antibody binding agent is sterile.

F19. The antibody binding agent of any one of embodiments F1 to F18, wherein the antibody binding agent is formulated as a sterile, lyophilized powder suitable for intravenous administration to a mammal.

G1. A kit comprising the a binding agent and/or a pharmaceutical composition of any one of embodiments A0 to A24.

G2. A kit comprising the humanized antibody binding agent of any one of embodiments B1 to B12, or C1 to C8.

G3. A kit comprising:
an antibody binding agent that specifically binds to *A. baumannii*; and
a pharmaceutical acceptable excipient, diluent, additive or carrier;
wherein the antibody binding agent comprises three or more CDRs each comprising at least 80% identity to any one of the CDRs selected from Table 1, Table 2, Table 3, Table 4, Table 5 and Table 6.

G4. A kit comprising the binding agent of any one of embodiments F1 to F19.

G5. The kit of anyone of embodiments G1 to G4, wherein the kit is configured for detection of *A. baumannii*.

G6. The kit of anyone of embodiments G1 to G5, wherein the kit is configured for diagnosis of an *A. baumannii* infection in a subject.

H1. A method of detecting *A. baumannii* in a sample comprising:
obtaining a sample from a subject suspected of having an *A. baumannii* infection, wherein the sample is suspected of comprising *A. baumannii*, or a portion thereof;
contacting the sample with an antibody binding agent that specifically binds to *A. baumannii*, wherein the antibody binding agent comprises three CDRs of a light chain variable domain of SEQ ID NO:2 or SEQ ID NO:28 and/or three CDRs of a heavy chain variable domain of SEQ ID NO:3, SEQ ID NO:67 or SEQ ID NO:29, and
detecting the presence or absence of a bound complex comprising the antibody binding agent, wherein the antibody binding agent is specifically bound to *A. baumannii*, or a portion thereof.

H2. The method of embodiment H1, wherein the antibody binding agent is the antibody binding agent of any one of embodiments F1 to F19.

H3. The method of embodiment H1 or H2, wherein the antibody binding agent comprises a detectable label.

I1. A pharmaceutical composition comprising:
a monoclonal antibody, or binding fragment thereof, that specifically binds to *A. baumannii*; and
a pharmaceutical acceptable excipient, diluent, additive or carrier;
wherein the monoclonal antibody, or binding fragment thereof inhibits and/or prevent *A. baumannii* induced sepsis in a mammal.

I2. A pharmaceutical composition comprising:
a monoclonal antibody, or binding fragment thereof, that specifically binds to *A. baumannii*; and
a pharmaceutical acceptable excipient, diluent, additive or carrier;
wherein the monoclonal antibody, or binding fragment thereof inhibits and/or prevent *A. baumannii* induced death in a mammal.

I3. The pharmaceutical composition of embodiment I1 or I2, wherein the monoclonal antibody blocks or inhibits *A. baumanni* enocytosis by a mammalian cell.

I4. The pharmaceutical composition of any one of embodiments I1 to I3, wherein the monoclonal antibody blocks or inhibits *A. baumanni* binding to a mammalian cell.

I5. The pharmaceutical composition of any one of embodiments I1 to I4, wherein the monoclonal antibody, or binding fragment thereof is the antibody binding agent of any one of embodiments A1 to A27, or a humanized antibody binding agent of any one of embodiments B2 to B12 or C1 to C8.

I6. A method of preventing or treating an *A. baumannii* infection in a subject having or at risk of having an *A. baumannii* infection comprising administering to the subject a therapeutically effective amount of the pharmaceutical of any one of embodiments I1 to I5.

I7. A method of detecting *A. baumannii* in a sample comprising:
obtaining a sample from a subject suspected of having an *A. baumannii* infection, wherein the sample is suspected of comprising *A. baumannii*, or a portion thereof;
contacting the sample with a monoclonal antibody, or binding fragment thereof, that specifically binds to *A. baumannii*, and
detecting the presence or absence of a bound complex comprising the monoclonal antibody and a fungus of the species *A. baumannii*.

The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It will be understood by those of skill in the art that numerous and various modifications can be made without departing from the spirit of the technology. Therefore, it should be clearly understood that the forms of the technology are illustrative only and are not intended to limit the scope of the technology.

All references cited herein are hereby incorporated by reference in their entirety.

What is claimed is:

1. A chimeric, CDR-grafted, humanized, or bispecific antibody or antigen binding portion thereof that specifically binds to *A. baumannii*, comprising:
   a CDR-L1 comprising the amino acid sequence of SEQ ID NO:4;
   a CDR-L2 comprising the amino acid sequence of SEQ ID NO:8;
   a CDR-L3 comprising the amino acid sequence of SEQ ID NO:12;
   a CDR-H1 comprising the amino acid sequence of SEQ ID NO:16;
   a CDR-H2 comprising the amino acid sequence of SEQ ID NO:20; and
   a CDR-H3 comprising the amino acid sequence of SEQ ID NO:24.

2. The chimeric, CDR-grafted, humanized, or bispecific antibody or antigen binding portion thereof of claim 1, wherein the antibody binding agent is a monoclonal antibody, or binding fragment thereof.

3. The chimeric, CDR-grafted, humanized, or bispecific antibody or antigen binding portion thereof of claim 2, wherein the monoclonal antibody comprises a constant region of an IgG1, IgG2, IgG3 or IgG4.

4. The chimeric, CDR-grafted, humanized, or bispecific antibody or antigen binding portion thereof of claim 2, wherein the monoclonal antibody comprises one or more human framework regions.

5. The chimeric, CDR-grafted, humanized, or bispecific antibody or antigen binding portion thereof of claim 2, wherein the monoclonal antibody is a humanized monoclonal antibody.

6. The chimeric, CDR-grafted, humanized, or bispecific antibody or antigen binding portion thereof of claim 1, wherein the antibody binding portion comprises a Fab, Fab', F(ab')2, or Fv fragment of the antibody, or a single chain Fv (scFV).

7. A pharmaceutical composition comprising the chimeric, CDR-grafted, humanized, or bispecific antibody or antigen binding portion thereof of claim 1, and one or more pharmaceutically acceptable excipients, diluents, additives or carriers.

8. A method of treating an *A. baumannii* infection in a subject comprising:
   a) providing a subject having an *A. baumannii* infection; and
   b) administering to the subject a therapeutically effective amount of a pharmaceutical composition comprising the chimeric, CDR-grafted, humanized, or bispecific antibody of claim 1.

9. A method of detecting *A. baumannii* in a sample comprising:
   (a) obtaining a sample from a subject suspected of having an *A. baumannii* infection;
   (b) contacting the sample with the chimeric, CDR-grafted, humanized, or bispecific antibody or antigen binding portion thereof of claim 1, and
   (c) detecting the presence or absence of a bound complex comprising (i) the chimeric, CDR-grafted, humanized, or bispecific antibody or antigen binding portion thereof and (ii) a bacteria of the species *A. baumannii*, or a portion thereof.

10. A chimeric, CDR-grafted, humanized, or bispecific antibody or antigen binding portion thereof that specifically binds to *A. baumannii*, comprising:
    a CDR-L1 comprising the amino acid sequence of SEQ ID NO:4;
    a CDR-L2 comprising the amino acid sequence of SEQ ID NO:8;
    a CDR-L3 comprising the amino acid sequence of SEQ ID NO:12;
    a CDR-H1 comprising the amino acid sequence of SEQ ID NO:55;
    a CDR-H2 comprising the amino acid sequence of SEQ ID NO:59; and
    a CDR-H3 comprising the amino acid sequence of SEQ ID NO:63.

11. A method of treating an *A. baumannii* infection in a subject comprising:
    a) providing a subject having an *A. baumannii* infection; and
    b) administering to the subject a therapeutically effective amount of the chimeric, CDR-grafted, humanized, or bispecific antibody of claim 10, or a pharmaceutical composition comprising the chimeric, CDR-grafted, humanized, or bispecific antibody of claim 10.

12. The chimeric, CDR-grafted, humanized, or bispecific antibody or antigen binding portion thereof of claim 10, wherein the antibody binding portion thereof is a monoclonal antibody, or binding fragment thereof.

13. The chimeric, CDR-grafted, humanized, or bispecific antibody or antigen binding portion thereof of claim 12, wherein the monoclonal antibody comprises a constant region of an IgG1, IgG2, IgG3 or IgG4.

14. The chimeric, CDR-grafted, humanized, or bispecific antibody or antigen binding portion thereof of claim 12, wherein the monoclonal antibody comprises one or more human framework regions.

15. The chimeric, CDR-grafted, humanized, or bispecific antibody or antigen binding portion thereof of claim 12, wherein the monoclonal antibody is a humanized monoclonal antibody.

16. The chimeric, CDR-grafted, humanized, or bispecific antibody or antigen binding portion thereof of claim 10, wherein the antibody binding portion comprises a Fab, Fab', F(ab')2, or Fv fragment of the antibody, or a single chain Fv (scFV).

17. A pharmaceutical composition comprising the chimeric, CDR-grafted, humanized, or bispecific antibody or antigen binding portion thereof of claim 10, and one or more pharmaceutically acceptable excipients, diluents, additives or carriers.

18. A method of detecting *A. baumannii* in a sample comprising:
    (a) obtaining a sample from a subject suspected of having an *A. baumannii* infection;
    (b) contacting the sample with the chimeric, CDR-grafted, humanized, or bispecific antibody or antigen binding portion thereof of claim 10, and
    (c) detecting the presence or absence of a bound complex comprising (i) the chimeric, CDR-grafted, humanized, or bispecific antibody or antibody binding portion thereof and (ii) a bacteria of the species *A. baumannii*, or a portion thereof.

\* \* \* \* \*

SEQUENCE LISTING

```
<160> NUMBER OF SEQ ID NOS: 67

<210> SEQ ID NO 1
<211> LENGTH: 268
<212> TYPE: PRT
<213> ORGANISM: Artificial Sequence
<220> FEATURE:
<223> OTHER INFORMATION: DHFR-3Loop fusion protein

<400> SEQUENCE: 1

Met Val Arg Pro Leu Asn Ser Ile Val Ala Val Ser Gln Asn Met Gly
1               5                   10                  15

Ile Gly Lys Asn Gly Asp Leu Pro Trp Pro Pro Leu Arg Asn Glu Phe
            20                  25                  30

Lys Tyr Phe Gln Arg Met Thr Thr Thr Ser Ser Val Glu Gly Lys Gln
        35                  40                  45

Asn Leu Val Ile Met Gly Arg Lys Thr Trp Phe Ser Ile Pro Glu Lys
    50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95

Ala Leu Arg Leu Ile Glu Gln Pro Glu Leu Ala Ser Lys Val Asp Met
            100                 105                 110

Val Trp Ile Val Gly Gly Ser Ser Val Tyr Gln Glu Ala Met Asn Gln
        115                 120                 125

Pro Gly His Leu Arg Leu Phe Val Thr Arg Ile Met Gln Glu Phe Glu
    130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Glu Lys Gly Ile
                165                 170                 175

Lys Tyr Lys Phe Glu Val Tyr Glu Lys Lys Gly Gly Gly Ser Asp
            180                 185                 190

Ser Gln His Asn Asn Gly Gly Lys Asp Gly Asn Leu Thr Asn Gly Pro
        195                 200                 205

Glu Leu Gln Asp Asp Leu Gly Gly Gly Ser Val Lys Gly Asp Val
    210                 215                 220

Asp Gly Ala Ser Ala Gly Ala Glu Tyr Lys Gln Lys Gln Ile Asn Gly
225                 230                 235                 240
```

```
Asn Gly Gly Gly Ser Arg Ala Thr Tyr Asn Ala Asp Glu Glu Phe
            245                 250                 255

Trp Asn Tyr Thr Ala Gly His His His His His
            260                 265

<210> SEQ ID NO 2
<211> LENGTH: 110
<212> TYPE: PRT
<213> ORGANISM: Mus musculus

<400> SEQUENCE: 2

Leu Pro Leu Ser Leu Pro Val Ser Leu Gly Asp Gln Ala Ser Ile Ser
1               5                   10                  15

Cys Arg Ser Ser Gln Ser Ile Val His Asn Asn Gly Asn Thr Tyr Leu
            20                  25                  30

Glu Trp Tyr Leu Gln Lys Pro Gly Gln Ser Pro Lys Leu Leu Ile Tyr
        35                  40                  45

Lys Val Ser Asn Arg Phe Ser Gly Val Pro Asp Arg Phe Ser Gly Ser
50                  55                  60

Gly Ser Gly Thr Asp Phe Thr Leu Lys Ile Ser Arg Val Glu Ala Glu
65                  70                  75                  80

Asp Leu Gly Val Tyr Tyr Cys Phe Gln Gly Ser His Val Pro Leu Thr
                85                  90                  95

Phe Gly Ala Gly Thr Lys Leu Glu Ile Lys Gly Ser Arg Ser
            100                 105                 110

<210> SEQ ID NO 3
<211> LENGTH: 118
<212> TYPE: PRT
<213> ORGANISM: Mus musculus

<400> SEQUENCE: 3

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Arg Ile Asn Pro Tyr Asn Gly Asp Ser Phe Tyr Asn Gln Lys Phe
50                  55                  60

Lys Gly Lys Ala Thr Leu Thr Val Asp Lys Ser Ser Asn Ile Ala His
65                  70                  75                  80

Met Glu Phe Leu Ser Leu Thr Ser Glu Asp Ser Ala Val Tyr Tyr Cys
                85                  90                  95

Gly Arg Ser Gly Asp Gly Pro Trp Phe Ala Tyr Trp Gly Gln Gly Thr
            100                 105                 110

Leu Val Thr Val Ser Ala
        115

<210> SEQ ID NO 4
<211> LENGTH: 11
<212> TYPE: PRT
<213> ORGANISM: Mus musculus

<400> SEQUENCE: 4

Gln Ser Ile Val His Asn Asn Gly Asn Thr Tyr
1               5                   10
```

```
<210> SEQ ID NO 5
<211> LENGTH: 13
<212> TYPE: PRT
<213> ORGANISM: Mus musculus

<400> SEQUENCE: 5

Gln Ser Ile Val His Asn Asn Gly Asn Thr Tyr Leu Glu
1               5                   10

<210> SEQ ID NO 6
<211> LENGTH: 14
<212> TYPE: PRT
<213> ORGANISM: Mus musculus

<400> SEQUENCE: 6

Arg Ser Ser Gln Ser Ile Val His Asn Asn Gly Asn Thr Tyr
1               5                   10

<210> SEQ ID NO 7
<211> LENGTH: 16
<212> TYPE: PRT
<213> ORGANISM: Mus musculus

<400> SEQUENCE: 7

Arg Ser Ser Gln Ser Ile Val His Asn Asn Gly Asn Thr Tyr Leu Glu
1               5                   10                  15

<210> SEQ ID NO 8
<211> LENGTH: 3
<212> TYPE: PRT
<213> ORGANISM: Mus musculus

<400> SEQUENCE: 8

Lys Val Ser
1

<210> SEQ ID NO 9
<211> LENGTH: 6
<212> TYPE: PRT
<213> ORGANISM: Mus musculus

<400> SEQUENCE: 9

Lys Val Ser Asn Arg Phe
1               5

<210> SEQ ID NO 10
<211> LENGTH: 6
<212> TYPE: PRT
<213> ORGANISM: Mus musculus

<400> SEQUENCE: 10

Val Ser Asn Arg Phe Ser
1               5

<210> SEQ ID NO 11
<211> LENGTH: 7
<212> TYPE: PRT
<213> ORGANISM: Mus musculus

<400> SEQUENCE: 11

Lys Val Ser Asn Arg Phe Ser
1               5
```

```
<210> SEQ ID NO 12
<211> LENGTH: 10
<212> TYPE: PRT
<213> ORGANISM: Mus musculus

<400> SEQUENCE: 12

Val Tyr Tyr Cys Phe Gln Gly Ser His Val
1               5                   10

<210> SEQ ID NO 13
<211> LENGTH: 13
<212> TYPE: PRT
<213> ORGANISM: Mus musculus

<400> SEQUENCE: 13

Val Tyr Tyr Cys Phe Gln Gly Ser His Val Pro Leu Thr
1               5                   10

<210> SEQ ID NO 14
<211> LENGTH: 13
<212> TYPE: PRT
<213> ORGANISM: Mus musculus

<400> SEQUENCE: 14

Asp Leu Gly Val Tyr Tyr Cys Phe Gln Gly Ser His Val
1               5                   10

<210> SEQ ID NO 15
<211> LENGTH: 16
<212> TYPE: PRT
<213> ORGANISM: Mus musculus

<400> SEQUENCE: 15

Asp Leu Gly Val Tyr Tyr Cys Phe Gln Gly Ser His Val Pro Leu Thr
1               5                   10                  15

<210> SEQ ID NO 16
<211> LENGTH: 6
<212> TYPE: PRT
<213> ORGANISM: Mus musculus

<400> SEQUENCE: 16

Ser Phe Thr Gly Tyr Thr
1               5

<210> SEQ ID NO 17
<211> LENGTH: 8
<212> TYPE: PRT
<213> ORGANISM: Mus musculus

<400> SEQUENCE: 17

Gly Tyr Ser Phe Thr Gly Tyr Thr
1               5

<210> SEQ ID NO 18
<211> LENGTH: 8
<212> TYPE: PRT
<213> ORGANISM: Mus musculus

<400> SEQUENCE: 18

Ser Phe Thr Gly Tyr Thr Met Asn
1               5
```

```
<210> SEQ ID NO 19
<211> LENGTH: 10
<212> TYPE: PRT
<213> ORGANISM: Mus musculus

<400> SEQUENCE: 19

Gly Tyr Ser Phe Thr Gly Tyr Thr Met Asn
1               5                   10

<210> SEQ ID NO 20
<211> LENGTH: 8
<212> TYPE: PRT
<213> ORGANISM: Mus musculus

<400> SEQUENCE: 20

Ile Asn Pro Tyr Asn Gly Asp Ser
1               5

<210> SEQ ID NO 21
<211> LENGTH: 11
<212> TYPE: PRT
<213> ORGANISM: Mus musculus

<400> SEQUENCE: 21

Arg Ile Asn Pro Tyr Asn Gly Asp Ser Phe Tyr
1               5                   10

<210> SEQ ID NO 22
<211> LENGTH: 14
<212> TYPE: PRT
<213> ORGANISM: Mus musculus

<400> SEQUENCE: 22

Ile Asn Pro Tyr Asn Gly Asp Ser Phe Tyr Asn Gln Lys Phe
1               5                   10

<210> SEQ ID NO 23
<211> LENGTH: 15
<212> TYPE: PRT
<213> ORGANISM: Mus musculus

<400> SEQUENCE: 23

Arg Ile Asn Pro Tyr Asn Gly Asp Ser Phe Tyr Asn Gln Lys Phe
1               5                   10                  15

<210> SEQ ID NO 24
<211> LENGTH: 7
<212> TYPE: PRT
<213> ORGANISM: Mus musculus

<400> SEQUENCE: 24

Ser Gly Asp Gly Pro Trp Phe
1               5

<210> SEQ ID NO 25
<211> LENGTH: 7
<212> TYPE: PRT
<213> ORGANISM: Mus musculus

<400> SEQUENCE: 25

Asp Gly Pro Trp Phe Ala Tyr
1               5
```

```
<210> SEQ ID NO 26
<211> LENGTH: 9
<212> TYPE: PRT
<213> ORGANISM: Mus musculus

<400> SEQUENCE: 26

Gly Arg Ser Gly Asp Gly Pro Trp Phe
1               5

<210> SEQ ID NO 27
<211> LENGTH: 11
<212> TYPE: PRT
<213> ORGANISM: Mus musculus

<400> SEQUENCE: 27

Gly Arg Ser Gly Asp Gly Pro Trp Phe Ala Tyr
1               5                   10

<210> SEQ ID NO 28
<211> LENGTH: 101
<212> TYPE: PRT
<213> ORGANISM: Mus musculus
<220> FEATURE:
<221> NAME/KEY: misc_feature
<222> LOCATION: (8)..(8)
<223> OTHER INFORMATION: Xaa can be any naturally occurring amino acid

<400> SEQUENCE: 28

Asp Ile Gly Met Thr Gln Ser Xaa Ser Pro Gln Asp Met Ser Val Gly
1               5                   10                  15

Pro Lys Val Thr Met Ser Ser Lys Cys Arg Lys Ser Leu Leu Asn Ser
            20                  25                  30

Arg Asn Gln Lys Lys Tyr Leu Thr Ser Asp Gln Gln Lys Pro Gly Gln
        35                  40                  45

Tyr Thr Lys Ser Leu Gly Asp Phe Ala Ser Ile Ser Glu Ser Arg Val
    50                  55                  60

Thr Asp Arg Phe Ile Gly Ser Gly Ser Gly Thr Asp Leu Pro Leu Gly
65                  70                  75                  80

Trp Gly Ile Leu Pro Pro Leu Pro Leu Ala Asp Tyr Phe Cys Gln Gln
                85                  90                  95

His Tyr Ser Thr Pro
            100

<210> SEQ ID NO 29
<211> LENGTH: 124
<212> TYPE: PRT
<213> ORGANISM: Mus musculus

<400> SEQUENCE: 29

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95
```

Arg Arg Arg Arg Ser Thr Ala Met Asp Tyr Trp Gly Gln Gly Thr Ser
            100                 105                 110

Val Thr Val Ser Ser Glu Ser Gln Ser Phe Pro Asn
            115                 120

<210> SEQ ID NO 30
<211> LENGTH: 8
<212> TYPE: PRT
<213> ORGANISM: Mus musculus

<400> SEQUENCE: 30

Leu Leu Asn Ser Arg Asn Gln Lys
1               5

<210> SEQ ID NO 31
<211> LENGTH: 10
<212> TYPE: PRT
<213> ORGANISM: Mus musculus

<400> SEQUENCE: 31

Ser Leu Leu Asn Ser Arg Asn Gln Lys Lys
1               5                   10

<210> SEQ ID NO 32
<211> LENGTH: 12
<212> TYPE: PRT
<213> ORGANISM: Mus musculus

<400> SEQUENCE: 32

Lys Ser Leu Leu Asn Ser Arg Asn Gln Lys Lys Tyr
1               5                   10

<210> SEQ ID NO 33
<211> LENGTH: 14
<212> TYPE: PRT
<213> ORGANISM: Mus musculus

<400> SEQUENCE: 33

Arg Lys Ser Leu Leu Asn Ser Arg Asn Gln Lys Lys Tyr Leu
1               5                   10

<210> SEQ ID NO 34
<211> LENGTH: 3
<212> TYPE: PRT
<213> ORGANISM: Mus musculus

<400> SEQUENCE: 34

Phe Ala Ser
1

<210> SEQ ID NO 35
<211> LENGTH: 5
<212> TYPE: PRT
<213> ORGANISM: Mus musculus

<400> SEQUENCE: 35

Asp Phe Ala Ser Ile
1               5

<210> SEQ ID NO 36
<211> LENGTH: 7
<212> TYPE: PRT
<213> ORGANISM: Mus musculus

```
<400> SEQUENCE: 36

Gly Asp Phe Ala Ser Ile Ser
1               5

<210> SEQ ID NO 37
<211> LENGTH: 9
<212> TYPE: PRT
<213> ORGANISM: Mus musculus

<400> SEQUENCE: 37

Leu Gly Asp Phe Ala Ser Ile Ser Glu
1               5

<210> SEQ ID NO 38
<211> LENGTH: 6
<212> TYPE: PRT
<213> ORGANISM: Mus musculus

<400> SEQUENCE: 38

Gln His Tyr Ser Thr Pro
1               5

<210> SEQ ID NO 39
<211> LENGTH: 7
<212> TYPE: PRT
<213> ORGANISM: Mus musculus

<400> SEQUENCE: 39

Gln Gln His Tyr Ser Thr Pro
1               5

<210> SEQ ID NO 40
<211> LENGTH: 8
<212> TYPE: PRT
<213> ORGANISM: Mus musculus

<400> SEQUENCE: 40

Cys Gln Gln His Tyr Ser Thr Pro
1               5

<210> SEQ ID NO 41
<211> LENGTH: 9
<212> TYPE: PRT
<213> ORGANISM: Mus musculus

<400> SEQUENCE: 41

Phe Cys Gln Gln His Tyr Ser Thr Pro
1               5

<210> SEQ ID NO 42
<211> LENGTH: 13
<212> TYPE: PRT
<213> ORGANISM: Mus musculus

<400> SEQUENCE: 42

Leu Ala Asp Tyr Phe Cys Gln Gln His Tyr Ser Thr Pro
1               5                   10

<210> SEQ ID NO 43
<211> LENGTH: 7
<212> TYPE: PRT
<213> ORGANISM: Mus musculus
```

```
<400> SEQUENCE: 43

Gly Phe Ser Leu Thr Ser Tyr
1               5

<210> SEQ ID NO 44
<211> LENGTH: 9
<212> TYPE: PRT
<213> ORGANISM: Mus musculus

<400> SEQUENCE: 44

Ser Gly Phe Ser Leu Thr Ser Tyr Gly
1               5

<210> SEQ ID NO 45
<211> LENGTH: 11
<212> TYPE: PRT
<213> ORGANISM: Mus musculus

<400> SEQUENCE: 45

Val Ser Gly Phe Ser Leu Thr Ser Tyr Gly Val
1               5                   10

<210> SEQ ID NO 46
<211> LENGTH: 13
<212> TYPE: PRT
<213> ORGANISM: Mus musculus

<400> SEQUENCE: 46

Thr Val Ser Gly Phe Ser Leu Thr Ser Tyr Gly Val His
1               5                   10

<210> SEQ ID NO 47
<211> LENGTH: 5
<212> TYPE: PRT
<213> ORGANISM: Mus musculus

<400> SEQUENCE: 47

Trp Ser Gly Gly Ser
1               5

<210> SEQ ID NO 48
<211> LENGTH: 7
<212> TYPE: PRT
<213> ORGANISM: Mus musculus

<400> SEQUENCE: 48

Ile Trp Ser Gly Gly Ser Thr
1               5

<210> SEQ ID NO 49
<211> LENGTH: 9
<212> TYPE: PRT
<213> ORGANISM: Mus musculus

<400> SEQUENCE: 49

Val Ile Trp Ser Gly Gly Ser Thr Asp
1               5

<210> SEQ ID NO 50
<211> LENGTH: 11
<212> TYPE: PRT
<213> ORGANISM: Mus musculus
```

<400> SEQUENCE: 50

Gly Val Ile Trp Ser Gly Gly Ser Thr Asp Tyr
1               5                   10

<210> SEQ ID NO 51
<211> LENGTH: 7
<212> TYPE: PRT
<213> ORGANISM: Mus musculus

<400> SEQUENCE: 51

Ala Arg Arg Arg Arg Ser Thr
1               5

<210> SEQ ID NO 52
<211> LENGTH: 9
<212> TYPE: PRT
<213> ORGANISM: Mus musculus

<400> SEQUENCE: 52

Cys Ala Arg Arg Arg Arg Ser Thr Ala
1               5

<210> SEQ ID NO 53
<211> LENGTH: 11
<212> TYPE: PRT
<213> ORGANISM: Mus musculus

<400> SEQUENCE: 53

Tyr Cys Ala Arg Arg Arg Arg Ser Thr Ala Met
1               5                   10

<210> SEQ ID NO 54
<211> LENGTH: 13
<212> TYPE: PRT
<213> ORGANISM: Mus musculus

<400> SEQUENCE: 54

Tyr Tyr Cys Ala Arg Arg Arg Arg Ser Thr Ala Met Asp
1               5                   10

<210> SEQ ID NO 55
<211> LENGTH: 6
<212> TYPE: PRT
<213> ORGANISM: Mus musculus

<400> SEQUENCE: 55

Ser Phe Thr Gly Tyr Phe
1               5

<210> SEQ ID NO 56
<211> LENGTH: 8
<212> TYPE: PRT
<213> ORGANISM: Mus musculus

<400> SEQUENCE: 56

Gly Tyr Ser Phe Thr Gly Tyr Phe
1               5

<210> SEQ ID NO 57
<211> LENGTH: 8
<212> TYPE: PRT
<213> ORGANISM: Mus musculus

```
<400> SEQUENCE: 57

Ser Phe Thr Gly Tyr Phe Met Asn
1               5

<210> SEQ ID NO 58
<211> LENGTH: 10
<212> TYPE: PRT
<213> ORGANISM: Mus musculus

<400> SEQUENCE: 58

Gly Tyr Ser Phe Thr Gly Tyr Phe Met Asn
1               5                   10

<210> SEQ ID NO 59
<211> LENGTH: 8
<212> TYPE: PRT
<213> ORGANISM: Mus musculus

<400> SEQUENCE: 59

Ile Asn Pro Tyr Asn Gly Asp Thr
1               5

<210> SEQ ID NO 60
<211> LENGTH: 11
<212> TYPE: PRT
<213> ORGANISM: Mus musculus

<400> SEQUENCE: 60

Arg Ile Asn Pro Tyr Asn Gly Asp Thr Phe Tyr
1               5                   10

<210> SEQ ID NO 61
<211> LENGTH: 14
<212> TYPE: PRT
<213> ORGANISM: Mus musculus

<400> SEQUENCE: 61

Ile Asn Pro Tyr Asn Gly Asp Thr Phe Tyr Asn Gln Lys Phe
1               5                   10

<210> SEQ ID NO 62
<211> LENGTH: 15
<212> TYPE: PRT
<213> ORGANISM: Mus musculus

<400> SEQUENCE: 62

Arg Ile Asn Pro Tyr Asn Gly Asp Thr Phe Tyr Asn Gln Lys Phe
1               5                   10                  15

<210> SEQ ID NO 63
<211> LENGTH: 5
<212> TYPE: PRT
<213> ORGANISM: Mus musculus

<400> SEQUENCE: 63

Leu Asn Tyr Arg Gly
1               5

<210> SEQ ID NO 64
<211> LENGTH: 7
<212> TYPE: PRT
<213> ORGANISM: Mus musculus
```

```
<400> SEQUENCE: 64

Leu Asn Tyr Arg Gly Ala Tyr
1               5

<210> SEQ ID NO 65
<211> LENGTH: 7
<212> TYPE: PRT
<213> ORGANISM: Mus musculus

<400> SEQUENCE: 65

Ala Arg Leu Asn Tyr Arg Gly
1               5

<210> SEQ ID NO 66
<211> LENGTH: 9
<212> TYPE: PRT
<213> ORGANISM: Mus musculus

<400> SEQUENCE: 66

Ala Arg Leu Asn Tyr Arg Gly Ala Tyr
1               5

<210> SEQ ID NO 67
<211> LENGTH: 120
<212> TYPE: PRT
<213> ORGANISM: Mus musculus

<400> SEQUENCE: 67

Gly Val Phe Ser Glu Val Gln Leu Gln Gln Ser Gly Pro Glu Leu Val
1               5                   10                  15

Lys Pro Gly Ala Ser Val Lys Ile Ser Cys Lys Ala Ser Gly Tyr Ser
            20                  25                  30

Phe Thr Gly Tyr Phe Met Asn Trp Val Lys Gln Ser His Gly Lys Ser
        35                  40                  45

Leu Glu Trp Ile Gly Arg Ile Asn Pro Tyr Asn Gly Asp Thr Phe Tyr
    50                  55                  60

Asn Gln Lys Phe Lys Gly Lys Ala Thr Leu Thr Val Asp Lys Ser Ser
65                  70                  75                  80

Ser Thr Ala His Met Glu Leu Arg Ser Leu Thr Ser Glu Asp Ser Ala
                85                  90                  95

Val Tyr Tyr Cys Ala Arg Leu Asn Tyr Arg Gly Ala Tyr Trp Gly Gln
            100                 105                 110

Gly Thr Leu Val Thr Val Ser Ala
        115                 120
```